United States Patent
Armstrong et al.

(10) Patent No.: US 12,331,069 B2
(45) Date of Patent: Jun. 17, 2025

(54) DOT1L DEGRADERS AND USES THEREOF

(71) Applicant: DANA-FARBER CANCER INSTITUTE, INC., Boston, MA (US)

(72) Inventors: Scott Armstrong, Wayland, MA (US); Jun Qi, Sharon, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 871 days.

(21) Appl. No.: 17/421,285

(22) PCT Filed: Jan. 9, 2020

(86) PCT No.: PCT/US2020/012825
§ 371 (c)(1),
(2) Date: Jul. 7, 2021

(87) PCT Pub. No.: WO2020/146561
PCT Pub. Date: Jul. 16, 2020

(65) Prior Publication Data
US 2022/0048942 A1      Feb. 17, 2022

Related U.S. Application Data

(60) Provisional application No. 62/790,314, filed on Jan. 9, 2019.

(51) Int. Cl.
*C07H 19/16* (2006.01)
*A61P 35/02* (2006.01)

(52) U.S. Cl.
CPC .............. *C07H 19/16* (2013.01); *A61P 35/02* (2018.01)

(58) Field of Classification Search
CPC .......... A61P 35/00; A61P 35/02; C07H 19/16; C07H 19/167
See application file for complete search history.

(56) References Cited

U.S. PATENT DOCUMENTS

| | | | | |
|---|---|---|---|---|
| 11,634,450 B2 * | 4/2023 | Qi | ................... | C07H 19/16 514/46 |
| 2016/0106725 A1 * | 4/2016 | Roden | ................... | A61K 31/454 514/19.5 |
| 2017/0232030 A1 | 8/2017 | Klaus et al. | | |

FOREIGN PATENT DOCUMENTS

| | | |
|---|---|---|
| JP | 2013544846 B2 | 12/2013 |
| JP | 2016517434 A5 | 6/2016 |
| WO | 2012075381 A1 | 6/2012 |
| WO | 2014/153001 A1 | 9/2014 |
| WO | 2014182744 A1 | 11/2014 |
| WO | 2017046036 A1 | 3/2017 |
| WO | 2018119441 A1 | 6/2018 |
| WO | 2018140809 A1 | 8/2018 |
| WO | 2020/006157 A1 | 1/2020 |

OTHER PUBLICATIONS

Naito et al., "Chemical Protein Knockdown: Development of Sniper Compounds that Induce Degradation of Target Proteins", Medchem News, 2018, vol. 28, No. 1, pp. 29-35.
Ohoka, "Development of Protein Knockdown Technology as Emerging Drug Discovery Strategy", Yakugaku Zasshi, 2018, vol. 138, pp. 1135-1143.
Klaus, et al., "DOT1 L Inhibitor EPZ-5676 Displays Synergistic Antiproliferative Activity in Combination with Standard of Care Drugs and Hypomethylating Agents in MLL-Rearranged Leukemia Cells," 2014, J Pharmacol Exp Ther, 350:646-656.
PubChem-CID-57345410, Create Date: 2012 (Sep. 7, 2012), p. 2.
Lai, A. C., et al., "Modular PROTAC Design for the Degradation of Oncogenic BCR-ABL", Angew. Chem. Int. Ed., 2016, vol. 55, pp. 807-810.
Li, X., et al., "Proteolysis-targeting chimera (PROTAC) for targeted protein degradation and cancer therapy", Journal of Hematology & Oncology, 2020, vol. 13, No. 50, 14 pages.
Tan, L, et al., "When Kinases Meet PROTACS", Chin. J. Chen., 2018 vol. 36, pp. 971-977.

* cited by examiner

*Primary Examiner* — Pancham Bakshi
(74) *Attorney, Agent, or Firm* — ArentFox Schiff LLP; Daniel W. J. Clarke D.; Shawn P. Foley

(57) ABSTRACT

Provided herein are bifunctional compounds with a moiety or domain that is a binder of the ubiquitin receptor RPN13 and another moiety or domain that is a binder of a target protein DOT1L to induce degradation of DOT1L. Also provided are pharmaceutical compositions comprising the bifunctional compounds, and methods of treating and/or preventing diseases (e.g., proliferative diseases, such as cancers). Provided also are methods of inducing the degradation of DOT1L by administering a bifunctional compound or composition described herein, wherein one domain of the bifunctional compound is a binder of the ubiquitin receptor RPN13 and another domain of the compound is a binder of the target protein DOT1L in a subject.

(I)

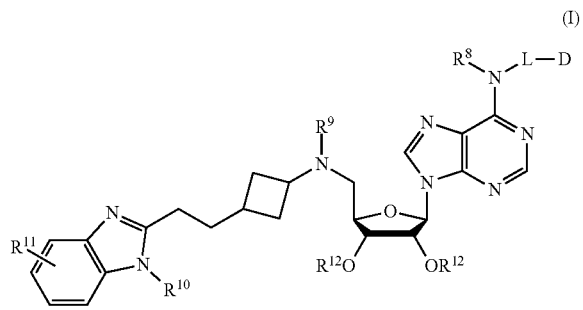

17 Claims, 22 Drawing Sheets
Specification includes a Sequence Listing.

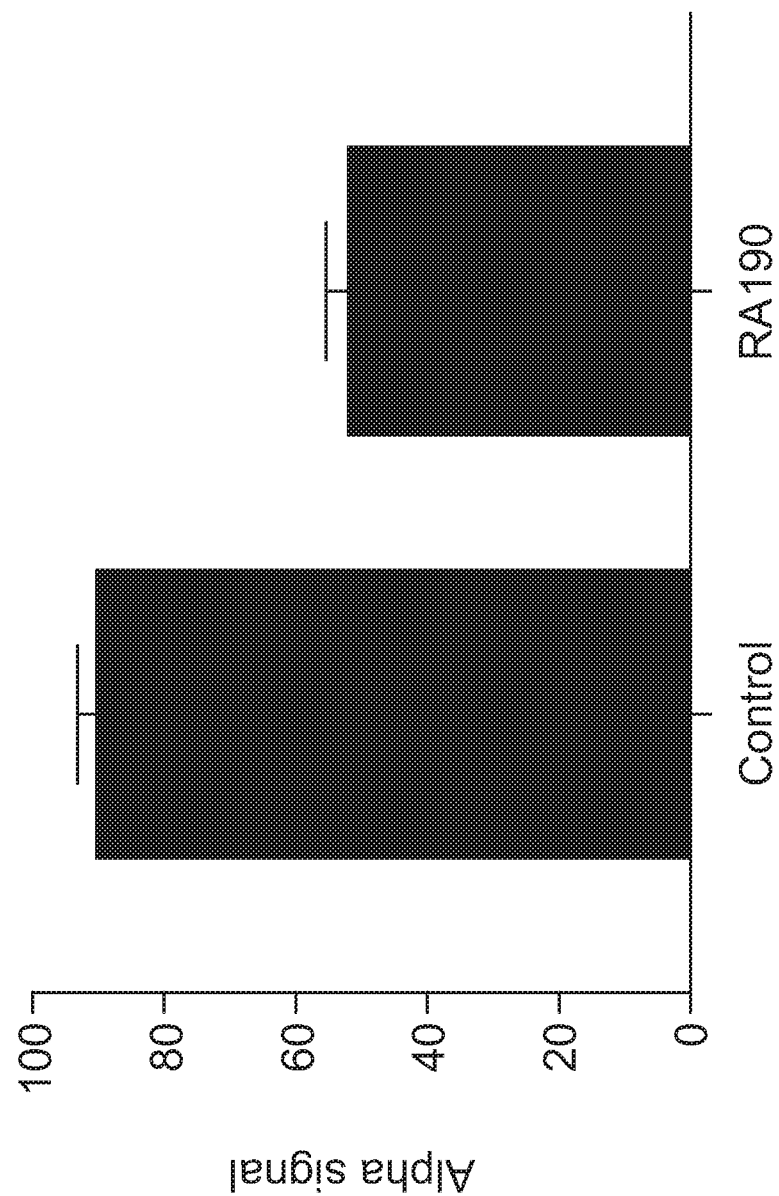

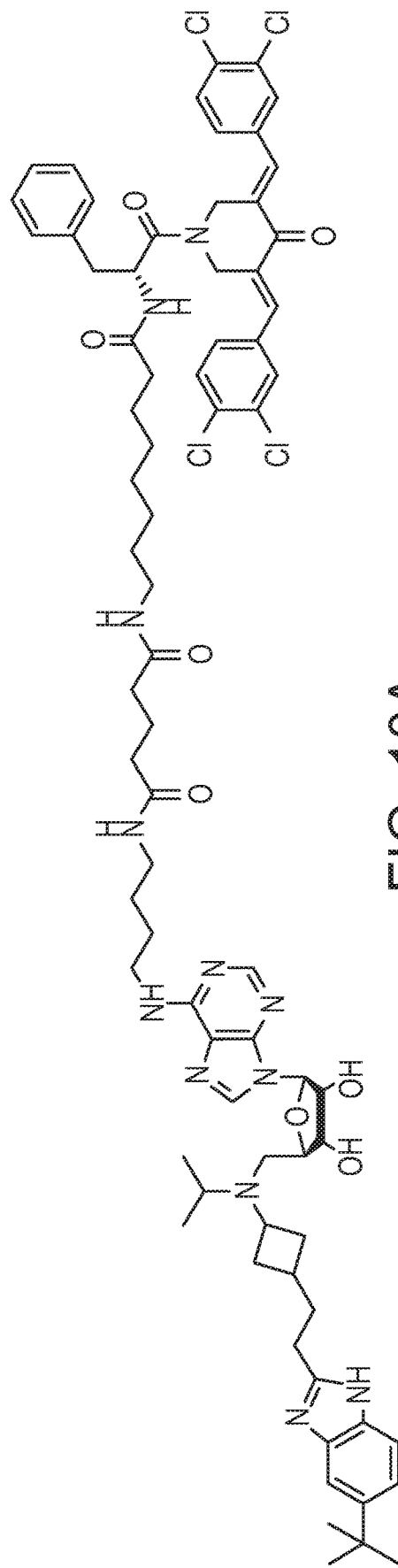
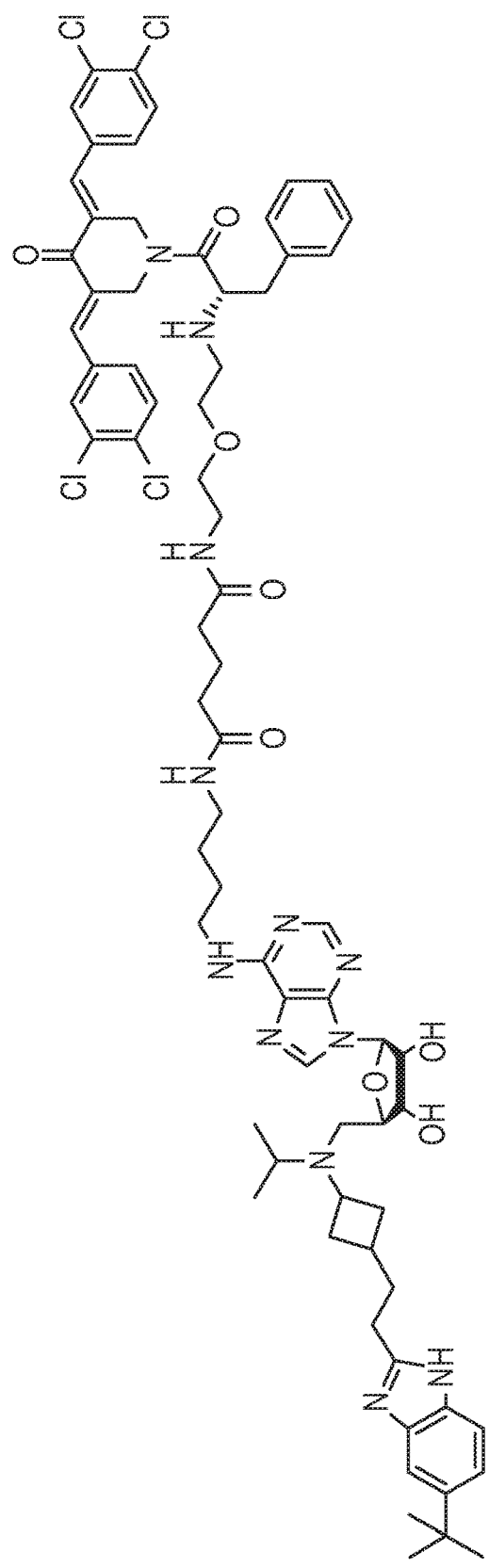
FIG. 10A
FIG. 10B

*Sample volume were less than the other samples.

SEQUENCE LISTING

<160> NUMBER OF SEQ ID NOS: 3

<210> SEQ ID NO 1
<211> LENGTH: 352
<212> TYPE: PRT
<213> ORGANISM: Homo sapiens

<400> SEQUENCE: 1

```
Met Glu Ser Gly Gly Arg Pro Ser Leu Cys Gln Phe Ile Leu Leu Gly
1               5                   10                  15

Thr Thr Ser Val Val Thr Ala Ala Leu Tyr Ser Val Tyr Arg Gln Lys
            20                  25                  30

Ala Arg Val Ser Gln Glu Leu Lys Gly Ala Lys Lys Val His Leu Gly
        35                  40                  45

Glu Asp Leu Lys Ser Ile Leu Ser Glu Ala Pro Gly Lys Cys Val Pro
    50                  55                  60

Tyr Ala Val Ile Glu Gly Ala Val Arg Ser Val Lys Glu Thr Leu Asn
65                  70                  75                  80

Ser Gln Phe Val Glu Asn Cys Lys Gly Val Ile Gln Arg Leu Thr Leu
            85                  90                  95

Gln Glu His Lys Met Val Trp Asn Arg Thr Thr His Leu Trp Asn Asp
            100                 105                 110

Cys Ser Lys Ile Ile His Gln Arg Thr Asn Thr Val Pro Phe Asp Leu
        115                 120                 125

Val Pro His Glu Asp Gly Val Asp Val Ala Val Arg Val Leu Lys Pro
    130                 135                 140

Leu Asp Ser Val Asp Leu Gly Leu Glu Thr Val Tyr Glu Lys Phe His
145                 150                 155                 160

Pro Ser Ile Gln Ser Phe Thr Asp Val Ile Gly His Tyr Ile Ser Gly
                165                 170                 175

Glu Arg Pro Lys Gly Ile Gln Glu Thr Glu Glu Met Leu Lys Val Gly
            180                 185                 190

Ala Thr Leu Thr Gly Val Gly Glu Leu Val Leu Asp Asn Asn Ser Val
```

```
            195                 200                 205
Arg Leu Gln Pro Pro Lys Gln Gly Met Gln Tyr Tyr Leu Ser Ser Gln
210                 215                 220

Asp Phe Asp Ser Leu Leu Gln Arg Gln Glu Ser Ser Val Arg Leu Trp
225                 230                 235                 240

Lys Val Leu Ala Leu Val Phe Gly Phe Ala Thr Cys Ala Thr Leu Phe
                245                 250                 255

Phe Ile Leu Arg Lys Gln Tyr Leu Gln Arg Gln Glu Arg Leu Arg Leu
                260                 265                 270

Lys Gln Met Gln Glu Glu Phe Gln Glu His Glu Ala Gln Leu Leu Ser
            275                 280                 285

Arg Ala Lys Pro Glu Asp Arg Glu Ser Leu Lys Ser Ala Cys Val Val
        290                 295                 300

Cys Leu Ser Ser Phe Lys Ser Cys Val Phe Leu Glu Cys Gly His Val
305                 310                 315                 320

Cys Ser Cys Thr Glu Cys Tyr Arg Ala Leu Pro Glu Pro Lys Lys Cys
                325                 330                 335

Pro Ile Cys Arg Gln Ala Ile Thr Arg Val Ile Pro Pro Tyr Asn Ser
                340                 345                 350

<210> SEQ ID NO 2
<211> LENGTH: 923
<212> TYPE: PRT
<213> ORGANISM: Homo sapiens

<400> SEQUENCE: 2

Met Glu Glu Gly Asn Asn Asn Glu Glu Val Ile His Leu Asn Asn Phe
1               5                   10                  15

His Cys His Arg Gly Gln Glu Trp Ile Asn Leu Arg Asp Gly Pro Ile
                20                  25                  30

Thr Ile Ser Asp Ser Ser Asp Glu Glu Arg Ile Pro Met Leu Val Thr
            35                  40                  45

Pro Ala Pro Gln Gln His Glu Glu Glu Asp Leu Asp Asp Val Ile
50                  55                  60

Leu Thr Glu Thr Asn Lys Pro Gln Arg Ser Arg Pro Asn Leu Ile Lys
65                  70                  75                  80

Pro Ala Ala Gln Trp Gln Asp Leu Lys Arg Leu Gly Glu Glu Arg Pro
                85                  90                  95

Lys Lys Ser Arg Ala Ala Phe Glu Ser Asp Lys Ser Ser Tyr Phe Ser
                100                 105                 110

Val Cys Asn Asn Pro Leu Phe Asp Ser Gly Ala Gln Asp Ser Glu
            115                 120                 125

Asp Asp Tyr Gly Glu Phe Leu Asp Leu Gly Pro Pro Gly Ile Ser Glu
130                 135                 140

Phe Thr Lys Pro Ser Gly Gln Thr Glu Arg Glu Pro Lys Pro Gly Pro
145                 150                 155                 160

Ser His Asn Gln Ala Ala Asn Asp Ile Val Asn Pro Arg Ser Glu Gln
                165                 170                 175

Lys Val Ile Ile Leu Glu Glu Gly Ser Leu Leu Tyr Thr Glu Ser Asp
                180                 185                 190

Pro Leu Glu Thr Gln Asn Gln Ser Glu Asp Ser Glu Thr Glu Leu
                195                 200                 205

Leu Ser Asn Leu Gly Glu Ser Ala Ala Leu Ala Asp Asp Gln Ala Ile
210                 215                 220
```

```
Glu Glu Asp Cys Trp Leu Asp His Pro Tyr Phe Gln Ser Leu Asn Gln
225                 230                 235                 240

Gln Pro Arg Glu Ile Thr Asn Gln Val Val Pro Gln Glu Arg Gln Pro
            245                 250                 255

Glu Ala Glu Leu Gly Arg Leu Leu Phe Gln His Glu Phe Pro Gly Pro
            260                 265                 270

Ala Phe Pro Arg Pro Glu Pro Gln Gln Gly Gly Ile Ser Gly Pro Ser
            275                 280                 285

Ser Pro Gln Pro Ala His Pro Leu Gly Glu Phe Glu Asp Gln Gln Leu
            290                 295                 300

Ala Ser Asp Asp Glu Glu Pro Gly Pro Ala Phe Pro Met Gln Glu Ser
305                 310                 315                 320

Gln Glu Pro Asn Leu Glu Asn Ile Trp Gly Gln Glu Ala Ala Glu Val
                325                 330                 335

Asp Gln Glu Leu Val Glu Leu Val Lys Glu Thr Glu Ala Arg Phe
                340                 345                 350

Pro Asp Val Ala Asn Gly Phe Ile Glu Ile Ile His Phe Lys Asn
                355                 360                 365

Tyr Tyr Asp Leu Asn Val Leu Cys Asn Phe Leu Leu Glu Asn Pro Asp
370                 375                 380

Tyr Pro Lys Arg Glu Asp Arg Ile Ile Ile Asn Pro Ser Ser Ser Leu
385                 390                 395                 400

Leu Ala Ser Gln Asp Glu Thr Lys Leu Pro Lys Ile Asp Phe Phe Asp
                405                 410                 415

Tyr Ser Lys Leu Thr Pro Leu Asp Gln Arg Cys Phe Ile Gln Ala Ala
                420                 425                 430

Asp Leu Leu Met Ala Asp Phe Lys Val Leu Ser Ser Gln Asp Ile Lys
                435                 440                 445

Trp Ala Leu His Glu Leu Lys Gly His Tyr Ala Ile Thr Arg Lys Ala
            450                 455                 460

Leu Ser Asp Ala Ile Lys Lys Trp Gln Glu Leu Ser Pro Glu Thr Ser
465                 470                 475                 480

Gly Lys Arg Lys Arg Lys Gln Met Asn Gln Tyr Ser Tyr Ile Asp
                485                 490                 495

Phe Lys Phe Glu Gln Gly Asp Ile Lys Ile Glu Lys Arg Met Phe Phe
            500                 505                 510

Leu Glu Asn Lys Arg Arg His Cys Arg Ser Tyr Asp Arg Arg Ala Leu
                515                 520                 525

Leu Pro Ala Val Gln Gln Glu Gln Glu Phe Tyr Glu Gln Lys Ile Lys
            530                 535                 540

Glu Met Ala Glu His Glu Asp Phe Leu Leu Ala Leu Gln Met Asn Glu
545                 550                 555                 560

Glu Gln Tyr Gln Lys Asp Gly Gln Leu Ile Glu Cys Arg Cys Cys Tyr
                565                 570                 575

Gly Glu Phe Pro Phe Glu Glu Leu Thr Gln Cys Ala Asp Ala His Leu
            580                 585                 590

Phe Cys Lys Glu Cys Leu Ile Arg Tyr Ala Gln Glu Ala Val Phe Gly
            595                 600                 605

Ser Gly Lys Leu Glu Leu Ser Cys Met Glu Gly Ser Cys Thr Cys Ser
            610                 615                 620

Phe Pro Thr Ser Glu Leu Glu Lys Val Leu Pro Gln Thr Ile Leu Tyr
625                 630                 635                 640

Lys Tyr Tyr Glu Arg Lys Ala Glu Glu Glu Val Ala Ala Ala Tyr Ala
```

-continued

```
                 645                 650                 655
Asp Glu Leu Val Arg Cys Pro Ser Cys Ser Phe Pro Ala Leu Leu Asp
                 660                 665                 670

Ser Asp Val Lys Arg Phe Ser Cys Pro Asn Pro His Cys Arg Lys Glu
                 675                 680                 685

Thr Cys Arg Lys Cys Gln Gly Leu Trp Lys Glu His Asn Gly Leu Thr
                 690                 695                 700

Cys Glu Glu Leu Ala Glu Lys Asp Asp Ile Lys Tyr Arg Thr Ser Ile
705                 710                 715                 720

Glu Glu Lys Met Thr Ala Ala Arg Ile Arg Lys Cys His Lys Cys Gly
                 725                 730                 735

Thr Gly Leu Ile Lys Ser Glu Gly Cys Asn Arg Met Ser Cys Arg Cys
                 740                 745                 750

Gly Ala Gln Met Cys Tyr Leu Cys Arg Val Ser Ile Asn Gly Tyr Asp
                 755                 760                 765

His Phe Cys Gln His Pro Arg Ser Pro Gly Ala Pro Cys Gln Glu Cys
                 770                 775                 780

Ser Arg Cys Ser Leu Trp Thr Asp Pro Thr Glu Asp Asp Glu Lys Leu
785                 790                 795                 800

Ile Glu Glu Ile Gln Lys Glu Ala Glu Glu Gln Lys Arg Lys Asn
                 805                 810                 815

Gly Glu Asn Thr Phe Lys Arg Ile Gly Pro Pro Leu Glu Lys Pro Val
                 820                 825                 830

Glu Lys Val Gln Arg Val Glu Ala Leu Pro Arg Pro Val Pro Gln Asn
                 835                 840                 845

Leu Pro Gln Pro Gln Met Pro Pro Tyr Ala Phe Ala His Pro Pro Phe
                 850                 855                 860

Pro Leu Pro Pro Val Arg Pro Val Phe Asn Asn Phe Pro Leu Asn Met
865                 870                 875                 880

Gly Pro Ile Pro Ala Pro Tyr Val Pro Leu Pro Asn Val Arg Val
                 885                 890                 895

Asn Tyr Asp Phe Gly Pro Ile His Met Pro Leu Glu His Asn Leu Pro
                 900                 905                 910

Met His Phe Gly Pro Gln Pro Arg His Arg Phe
                 915                 920
```

<210> SEQ ID NO 3
<211> LENGTH: 866
<212> TYPE: PRT
<213> ORGANISM: Homo sapiens

<400> SEQUENCE: 3

```
Met Glu Glu Gly Asn Asn Asn Glu Glu Val Ile His Leu Asn Asn Phe
1                 5                  10                  15

His Cys His Arg Gly Gln Glu Trp Ile Asn Leu Arg Asp Gly Pro Ile
                 20                  25                  30

Thr Ile Ser Asp Ser Ser Asp Glu Arg Ile Pro Met Leu Val Thr
                 35                  40                  45

Pro Ala Pro Gln Gln His Glu Glu Glu Asp Leu Asp Asp Asp Val Ile
                 50                  55                  60

Leu Thr Glu Asp Asp Ser Glu Asp Asp Tyr Gly Glu Phe Leu Asp Leu
65                  70                  75                  80

Gly Pro Pro Gly Ile Ser Glu Phe Thr Lys Pro Ser Gly Gln Thr Glu
                 85                  90                  95
```

```
Arg Glu Pro Lys Pro Gly Pro Ser His Asn Gln Ala Ala Asn Asp Ile
                100                 105                 110
Val Asn Pro Arg Ser Glu Gln Lys Val Ile Ile Leu Glu Glu Gly Ser
            115                 120                 125
Leu Leu Tyr Thr Glu Ser Asp Pro Leu Glu Thr Gln Asn Gln Ser Ser
        130                 135                 140
Glu Asp Ser Glu Thr Glu Leu Leu Ser Asn Leu Gly Glu Ser Ala Ala
145                 150                 155                 160
Leu Ala Asp Asp Gln Ala Ile Glu Glu Asp Cys Trp Leu Asp His Pro
                165                 170                 175
Tyr Phe Gln Ser Leu Asn Gln Gln Pro Arg Glu Ile Thr Asn Gln Val
            180                 185                 190
Val Pro Gln Glu Arg Gln Pro Glu Ala Glu Leu Gly Arg Leu Leu Phe
        195                 200                 205
Gln His Glu Phe Pro Gly Pro Ala Phe Pro Arg Pro Glu Pro Gln Gln
    210                 215                 220
Gly Gly Ile Ser Gly Pro Ser Pro Gln Pro Ala His Pro Leu Gly
225                 230                 235                 240
Glu Phe Glu Asp Gln Gln Leu Ala Ser Asp Asp Glu Glu Pro Gly Pro
                245                 250                 255
Ala Phe Pro Met Gln Glu Ser Gln Glu Pro Asn Leu Glu Asn Ile Trp
            260                 265                 270
Gly Gln Glu Ala Ala Glu Val Asp Gln Glu Leu Val Glu Leu Leu Val
        275                 280                 285
Lys Glu Thr Glu Ala Arg Phe Pro Asp Val Ala Asn Gly Phe Ile Glu
    290                 295                 300
Glu Ile Ile His Phe Lys Asn Tyr Tyr Asp Leu Asn Val Leu Cys Asn
305                 310                 315                 320
Phe Leu Leu Glu Asn Pro Asp Tyr Pro Lys Arg Glu Asp Arg Ile Ile
                325                 330                 335
Ile Asn Pro Ser Ser Ser Leu Leu Ala Ser Gln Asp Glu Thr Lys Leu
            340                 345                 350
Pro Lys Ile Asp Phe Phe Asp Tyr Ser Lys Leu Thr Pro Leu Asp Gln
        355                 360                 365
Arg Cys Phe Ile Gln Ala Ala Asp Leu Leu Met Ala Asp Phe Lys Val
    370                 375                 380
Leu Ser Ser Gln Asp Ile Lys Trp Ala Leu His Glu Leu Lys Gly His
385                 390                 395                 400
Tyr Ala Ile Thr Arg Lys Ala Leu Ser Asp Ala Ile Lys Lys Trp Gln
                405                 410                 415
Glu Leu Ser Pro Glu Thr Ser Gly Lys Arg Lys Lys Arg Lys Gln Met
            420                 425                 430
Asn Gln Tyr Ser Tyr Ile Asp Phe Lys Phe Glu Gln Gly Asp Ile Lys
        435                 440                 445
Ile Glu Lys Arg Met Phe Phe Leu Glu Asn Lys Arg Arg His Cys Arg
    450                 455                 460
Ser Tyr Asp Arg Arg Ala Leu Leu Pro Ala Val Gln Glu Gln Glu
465                 470                 475                 480
Phe Tyr Glu Gln Lys Ile Lys Glu Met Ala Glu His Glu Asp Phe Leu
                485                 490                 495
Leu Ala Leu Gln Met Asn Glu Glu Gln Tyr Gln Lys Asp Gly Gln Leu
            500                 505                 510
Ile Glu Cys Arg Cys Cys Tyr Gly Glu Phe Pro Phe Glu Glu Leu Thr
```

```
            515                 520                 525
    Gln Cys Ala Asp Ala His Leu Phe Cys Lys Glu Cys Leu Ile Arg Tyr
            530                 535                 540

Ala Gln Glu Ala Val Phe Gly Ser Gly Lys Leu Glu Leu Ser Cys Met
    545                 550                 555                 560

Glu Gly Ser Cys Thr Cys Ser Phe Pro Thr Ser Glu Leu Glu Lys Val
                        565                 570                 575

Leu Pro Gln Thr Ile Leu Tyr Lys Tyr Tyr Glu Arg Lys Ala Glu Glu
                    580                 585                 590

Glu Val Ala Ala Ala Tyr Ala Asp Glu Leu Val Arg Cys Pro Ser Cys
                595                 600                 605

Ser Phe Pro Ala Leu Leu Asp Ser Asp Val Lys Arg Phe Ser Cys Pro
            610                 615                 620

Asn Pro His Cys Arg Lys Glu Thr Cys Arg Lys Cys Gln Gly Leu Trp
    625                 630                 635                 640

Lys Glu His Asn Gly Leu Thr Cys Glu Glu Leu Ala Glu Lys Asp Asp
                        645                 650                 655

Ile Lys Tyr Arg Thr Ser Ile Glu Glu Lys Met Thr Ala Ala Arg Ile
                    660                 665                 670

Arg Lys Cys His Lys Cys Gly Thr Gly Leu Ile Lys Ser Glu Gly Cys
                675                 680                 685

Asn Arg Met Ser Cys Arg Cys Gly Ala Gln Met Cys Tyr Leu Cys Arg
            690                 695                 700

Val Ser Ile Asn Gly Tyr Asp His Phe Cys Gln His Pro Arg Ser Pro
    705                 710                 715                 720

Gly Ala Pro Cys Gln Cys Ser Arg Cys Ser Leu Trp Thr Asp Pro
                        725                 730                 735

Thr Glu Asp Asp Glu Lys Leu Ile Glu Glu Ile Gln Lys Glu Ala Glu
                    740                 745                 750

Glu Glu Gln Lys Arg Lys Asn Gly Glu Asn Thr Phe Lys Arg Ile Gly
                755                 760                 765

Pro Pro Leu Glu Lys Pro Val Glu Lys Val Gln Arg Val Glu Ala Leu
            770                 775                 780

Pro Arg Pro Val Pro Gln Asn Leu Pro Gln Pro Gln Met Pro Pro Tyr
    785                 790                 795                 800

Ala Phe Ala His Pro Pro Phe Pro Leu Pro Pro Val Arg Pro Val Phe
                        805                 810                 815

Asn Asn Phe Pro Leu Asn Met Gly Pro Ile Pro Ala Pro Tyr Val Pro
                    820                 825                 830

Pro Leu Pro Asn Val Arg Val Asn Tyr Asp Phe Gly Pro Ile His Met
                835                 840                 845

Pro Leu Glu His Asn Leu Pro Met His Phe Gly Pro Gln Pro Arg His
            850                 855                 860

Arg Phe
    865
```

DOT1L DEGRADERS AND USES THEREOF

RELATED APPLICATIONS

This application is a national stage application, filed under 35 U.S.C. § 371, of International Application No. PCT/US2020/012825, filed Jan. 9, 2020, which claims priority under 35 U.S.C. § 119 (e) to U.S. Provisional Application Ser. No. 62/790,314, filed Jan. 9, 2019, the contents of each of which are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 9, 2020, is named "D050470150WO00-SEQ-JC" and is 18.2 KB in size.

GOVERNMENT SUPPORT

This invention was made with government support under grant number R01 CA176745 awarded by the National Institutes of Health. The government has certain rights in the invention.

BACKGROUND OF THE INVENTION

Recently, a new therapeutic strategy to reduce and/or eliminate proteins associated with certain pathological states, PROTAC (proteolysis targeting chimeras; see, e.g., U.S. patent application U.S. Ser. No. 14/792,414, filed Jul. 6, 2015, published as US 2016-0058872 on Mar. 3, 2016; and U.S. Ser. No. 14/707,930, filed May 8, 2015, issued as U.S. Pat. No. 9,694,084 on Jul. 4, 2017, each of which is incorporated herein by reference), was developed by creating bifunctional compounds that recruit E3 ubiquitin ligase to a target protein and subsequently induce ubiquitination and proteasome-mediated degradation of the target protein. E3 ubiquitin ligases are proteins that, in combination with an E2 ubiquitin-conjugating enzyme, promote the attachment of ubiquitin to a lysine of a target protein via an isopeptide bond (e.g., an amide bond that is not present on the main chain of a protein). The ubiquitination of the protein results in degradation of the target protein by the proteasome.

RA190 covalently binds to the ubiquitin receptor RPN13 (ADRM1), changing the function of RPN13 to interact with polyubiquitinated proteins that cannot enter the particle 19S proteasome, which in turn inhibits proteasome function. See US Appl. Pub. No. 2016/0106725 published Apr. 21, 2016, which is incorporated herein by reference. The subsequent accumulation of polyubiquitinated proteins induces apoptosis in cells (e.g., cancer cells). In certain embodiments, RA190-based compounds may directly bring targeted proteins to the proteasome. There is therefore a need for compounds that both bind the ubiquitin receptor RPN13 as well as target the DOT1L protein, which brings the selected DOT1L protein to the proteasome, thereby inducing proteasome degradation of the target protein DOT1L.

SUMMARY OF THE INVENTION

The present disclosure stems from the recognition that certain proteins (e.g., DOT1L) are associated with the pathogenesis of particular diseases (e.g., proliferative diseases, cancers, benign neoplasms, pathological angiogenesis, inflammatory diseases, autoimmune diseases, and musculoskeletal diseases), and that by targeting a selected protein (e.g., DOT1L) for degradation using a binder of the ubiquitin receptor RPN13 to bring the target protein to the proteasome, the target protein (e.g., DOT1L) is degraded by the proteasome. In particular, compounds that can take advantage of cellular machinery involved in protein homeostasis (e.g., ubiquitination and proteasome degradation) to target the degradation of certain proteins (e.g., DOT1L) may find use as therapeutic agents. The disclosure therefore provides new compounds, compositions, and methods for the treatment of various diseases associated with DOT1L (e.g., cancers, benign neoplasms, pathological angiogenesis, inflammatory diseases, and autoimmune diseases) based on this discovery. Described herein are compounds of Formulae (I) and (IA). The compounds described herein include a domain that binds to the ubiquitin receptor RPN13, and another domain that binds a target (e.g., DOT1L protein) and therefore may be useful in promoting the degradation of the target (e.g., DOT1L protein). The compounds may be useful in treating and/or preventing a disease or condition associated with a target protein DOT1L, e.g., in treating and/or preventing a proliferative disease (e.g., cancers, benign neoplasms, pathological angiogenesis, inflammatory diseases, and autoimmune diseases) in a subject in need thereof. Also provided are pharmaceutical compositions and kits including a compound described herein.

In one aspect, the present disclosure provides compounds of Formula (I):

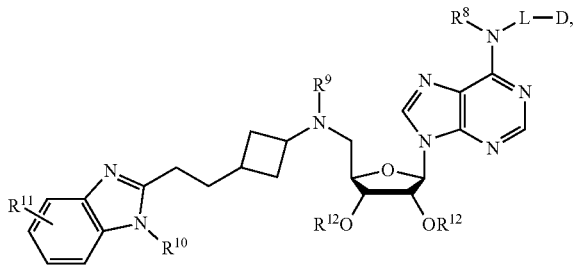

and pharmaceutically acceptable salts, solvates, hydrates, polymorphs, co-crystals, tautomers, stereoisomers, isotopically labeled derivatives, and prodrugs thereof, wherein $R^8$, $R^9$, $R^{10}$, $R^{11}$, $R^{12}$, L, and D are as defined herein.

In Formula (I), D is a binder of the ubiquitin receptor RPN13, where D is of the formula:

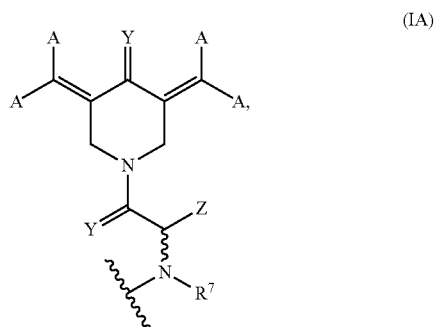

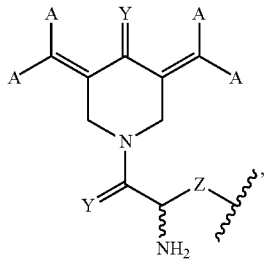

(IB)

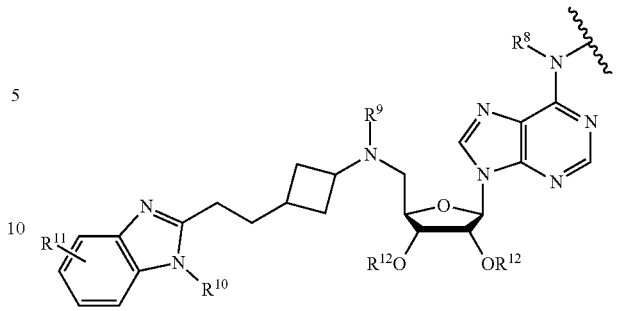

and pharmaceutically acceptable salts, solvates, hydrates, polymorphs, co-crystals, tautomers, stereoisomers, isotopically labeled derivatives, and prodrugs thereof. D is derived from RA 190, a binder of the ubiquitin receptor RPN13. In Formula (I), the moiety is a binder of DOT1L. See US Appl. Pub. No. US 2016/0060269 published Mar. 3, 2016, which is incorporated herein by reference.

Exemplary compounds of Formula (I) include, but are not limited to:

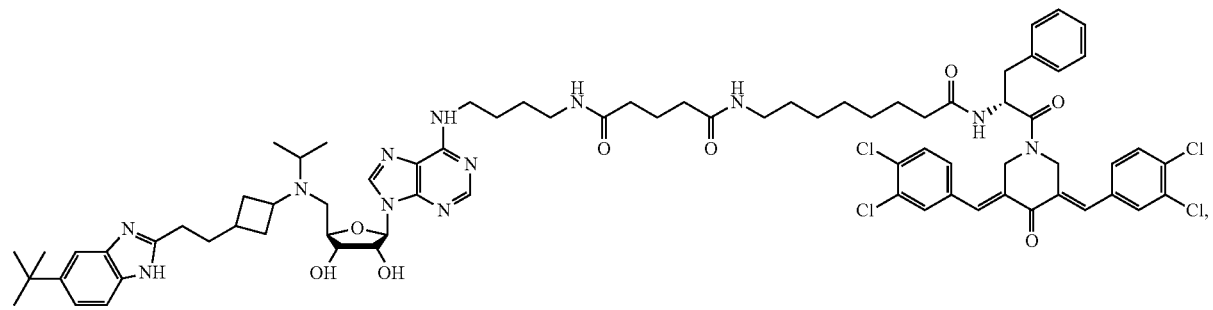

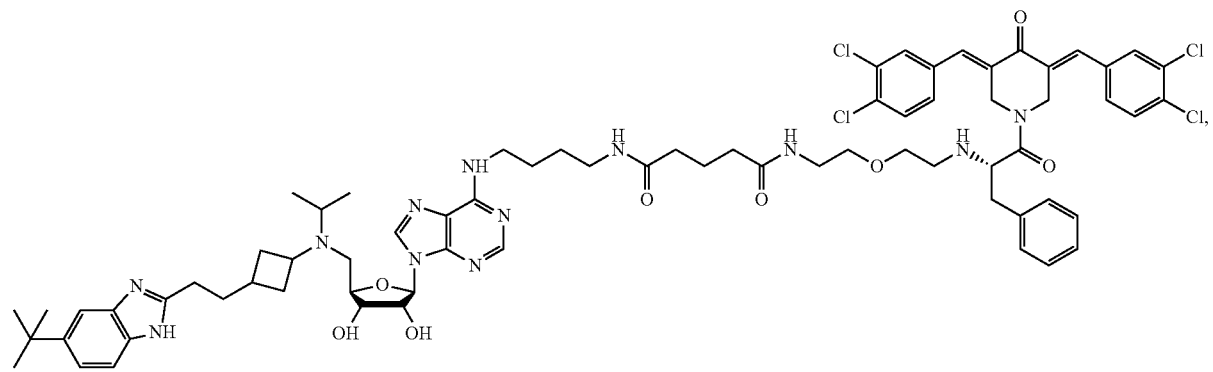

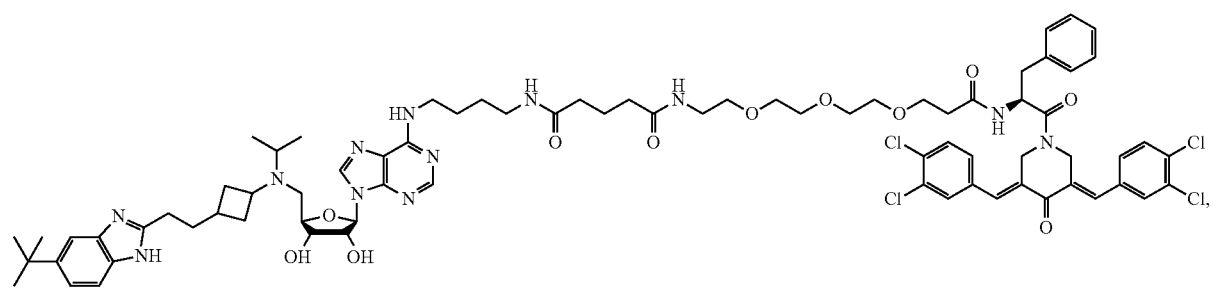

and pharmaceutically acceptable salts, solvates, hydrates, polymorphs, co-crystals, tautomers, stereoisomers, isotopically labeled derivatives, and prodrugs thereof.

In another aspect, described herein are pharmaceutical compositions including a compound described herein, and optionally a pharmaceutically acceptable excipient. In certain embodiments, a pharmaceutical composition described herein includes a therapeutically or prophylactically effective amount of a compound described herein. The pharmaceutical compositions may be useful in inducing the degradation of the target (e.g., DOT1L protein) in a subject or cell, in treating a disease (e.g., a proliferative disease) in a subject in need thereof, or in preventing a disease in a subject in need thereof. In certain embodiments, the compound being administered or used induces the degradation of DOT1L protein, thereby treating and/or preventing diseases associated with DOT1L (e.g., proliferative diseases, cancers, benign neoplasms, pathological angiogenesis, inflammatory diseases, autoimmune diseases, and musculoskeletal diseases).

In still another aspect, described herein are kits including a container with a compound or pharmaceutical composition described herein. A kit described herein may include a single dose or multiple doses of the compound or pharmaceutical composition. The described kits may be useful in inducing the degradation of DOT1L protein in a subject, biological sample, tissue, or cell, in treating a disease associated with aberrant activity of DOT1L in a subject in need thereof, in preventing a disease associated with aberrant activity of DOT1L protein in a subject in need thereof, in treating a disease (e.g., proliferative disease) in a subject in need thereof, and/or in preventing a disease (e.g., proliferative disease) in a subject in need thereof. In certain embodiments, a kit described herein further includes instructions for using the compound or pharmaceutical composition included in the kit.

In another aspect, the present disclosure provides methods of inducing the degradation of DOT1L protein in a subject in need thereof, the methods comprising administering to the subject a therapeutically effective amount of a compound or pharmaceutical composition described herein.

In another aspect, the present disclosure provides methods of inducing the degradation of DOT1L protein in a biological sample, tissue, or cell, the methods comprising contacting the biological sample, tissue, or cell with an effective amount of a compound or pharmaceutical composition described herein.

In certain embodiments, the compound being administered or used selectively induces the degradation of the DOT1L protein. The degradation of DOT1L thereby treats and/or preventing diseases associated with DOT1L (e.g., proliferative diseases, cancers, benign neoplasms, pathological angiogenesis, inflammatory diseases, autoimmune diseases, and musculoskeletal diseases). When a compound, pharmaceutical composition, method, use, or kit is referred to as "selectively," "specifically," or "competitively" inducing the degradation of a target (e.g., a protein), the compound, pharmaceutical composition, method, use, or kit induces the degradation of a particular target (e.g., DOT1L protein) to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than another protein (e.g., other methyltransferases).

In another aspect, the present disclosure provides methods of killing cells (e.g. killing a cancer cell or tumor cell), the methods comprising contacting the cell with an effective amount of a compound or pharmaceutical composition described herein.

Another aspect of the present disclosure relates to methods of treating a disease in a subject in need thereof, the methods comprising administering to the subject a therapeutically effective amount of a compound or pharmaceutical composition described herein. In another aspect, the present disclosure provides methods of preventing a disease in a subject in need thereof, the methods comprise administering to the subject a prophylactically effective amount of a compound or pharmaceutical composition described herein.

In yet another aspect, the present disclosure provides compounds and pharmaceutical compositions described herein for use in a method of the disclosure (e.g., a method of inducing the degradation of a target (e.g., DOT1L protein), a method of killing cells (e.g. cancer cells or tumor cells), a method of treating a disease (e.g., a proliferative disease), or a method of preventing a disease (e.g., a proliferative disease)).

Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987. The disclosure is not intended to be limited in any manner by the exemplary listing of substituents described herein.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, N Y, 1962); and Wilen, *Tables of Resolving Agents and Optical Resolutions* p. 268 (E. L. Eliel, Ed., Univ. of Notre Dame Press, Notre Dame, IN 1972). The disclosure additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, the term "alkyl" includes straight, branched and cyclic alkyl groups. An analogous convention applies to other generic terms such as "alkenyl", "alkynyl", and the like. Furthermore, the terms "alkyl", "alkenyl", "alkynyl", and the like encompass both substituted and unsubstituted groups. In certain embodiments, "lower alkyl" is used to indicate those alkyl groups (cyclic, acyclic, substituted, unsubstituted, branched or unbranched) having 1-6 carbon atoms.

In certain embodiments, the alkyl, alkenyl, and alkynyl groups employed in the disclosure contain 1-20 aliphatic carbon atoms. In certain other embodiments, the alkyl, alkenyl, and alkynyl groups employed in the disclosure contain 1-10 aliphatic carbon atoms. In yet other embodiments, the alkyl, alkenyl, and alkynyl groups employed in the disclosure contain 1-8 aliphatic carbon atoms. In still other embodiments, the alkyl, alkenyl, and alkynyl groups employed in the disclosure contain 1-6 aliphatic carbon atoms. In yet other embodiments, the alkyl, alkenyl, and alkynyl groups employed in the disclosure contain 1-4 carbon atoms. Illustrative aliphatic groups thus include, but are not limited to, for example, methyl, ethyl, n-propyl, isopropyl, cyclopropyl, —$CH_2$-cyclopropyl, vinyl, allyl, n-butyl, sec-butyl, isobutyl, tert-butyl, cyclobutyl, —$CH_2$-cyclobutyl, n-pentyl, sec-pentyl, isopentyl, tert-pentyl, cyclopentyl, —$CH_2$-cyclopentyl, n-hexyl, sec-hexyl, cyclohexyl, —$CH_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl, and the like.

The term "alkyl" refers to a radical of a straight-chain or branched saturated hydrocarbon group. In some embodiments, the term "alkyl" refers to a radical of a straight-chain or branched saturated hydrocarbon group having a specified amount of carbon atoms.

In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), propyl ($C_3$) (e.g., n-propyl, isopropyl), butyl ($C_4$) (e.g., n-butyl, tert-butyl, sec-butyl, isobutyl), pentyl ($C_5$) (e.g., n-pentyl, 3-pentanyl, amyl, neopentyl, 3-methyl-2-butanyl, tertiary amyl), and hexyl ($C_6$) (e.g., n-hexyl). Additional examples of alkyl groups include n-heptyl ($C_7$), n-octyl ($C_8$), and the like. Unless otherwise specified, each instance of an alkyl group is independently unsubstituted (an "unsubstituted alkyl") or substituted (a "substituted alkyl") with one or more substituents (e.g., halogen, such as F). In certain embodiments, the alkyl group is an unsubstituted $C_{1-10}$ alkyl (such as unsubstituted $C_{1-6}$ alkyl, e.g., —$CH_3$ (Me), unsubstituted ethyl (Et), unsubstituted propyl (Pr, e.g., unsubstituted n-propyl (n-Pr), unsubstituted isopropyl (i-Pr)), unsubstituted butyl (Bu, e.g., unsubstituted n-butyl (n-Bu), unsubstituted tert-butyl (tert-Bu or t-Bu), unsubstituted sec-butyl (sec-Bu), unsubstituted isobutyl (i-Bu)). In certain embodiments, the alkyl group is a substituted $C_{1-10}$ alkyl (such as substituted $C_{1-6}$ alkyl, e.g., —$CH_2F$, —$CHF_2$, —$CF_3$, Bn). In some embodiments, a substituted alkyl group is a haloalkyl group.

The term "haloalkyl" refers to an alkyl group as defined above wherein one or more hydrogen atoms are replaced with a halogen (i.e., —F, —Cl, —Br, or —I). In certain embodiments, the haloalkyl group includes one or more terminal moieties selected from —$CH_2F$, —$CHF_2$, and —$CF_3$ (e.g., —$CH_2CH_2CF_3$). In certain embodiments, the haloalkyl group includes one or more internal moieties selected from —CHF and —$CF_2$ (e.g., —$CHFCH_2CH_3$, —$CHFCHFCH_3$, —$CH_2CF_2CH_3$, —$CF_2CH_2CH_3$, —$CF_2CHFCH_3$, —$CF_2CF_2CH_3$, —$CH_2CHFCH_3$, and —$CH_2CF_2CH_3$).

In certain embodiments, the haloalkyl group includes at least one terminal moiety that includes a halogen atom and at least one internal moiety that includes a halogen atom (e.g., —$CHFCH_2F$, —$CHFCF_2H$, —$CHFCF_3$, —$CF_2CH_2F$, —$CF_2CF_2H$, —$CF_2CF_3$). In certain embodiment, the haloalkyl group is a perhaloalkyl group (e.g., —$CF_3$, —$CF_2CF_3$, —$CF(CF_3)_2$, and —$CF_2CF_2CF_3$).

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted C$_{2-10}$ alkenyl. In an alkenyl group, a C=C double bond for which the stereochemistry is not specified (e.g., —CH=CHCH$_3$ or

)

may be an (E)- or (Z)-double bond.

"Alkynyl" refers to a radical of a straight-chain or branched hydrocarbon group having from 2 to 20 carbon atoms, one or more carbon-carbon triple bonds, and optionally one or more double bonds ("C$_{2-20}$ alkynyl"). In some embodiments, an alkynyl group has 2 to 10 carbon atoms ("C$_{2-10}$ alkynyl"). In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1-butynyl). Examples of C$_{2-4}$ alkynyl groups include, without limitation, ethynyl (C$_2$), 1-propynyl (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted C$_{2-10}$ alkynyl. In certain embodiments, the alkynyl group is substituted C$_{2-10}$ alkynyl.

"Carbocyclyl" or "carbocyclic" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"). In some embodiments, a carbocyclyl group has 3 to 6 ring carbon atoms ("C$_{3-6}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted C$_{3-10}$ carbocyclyl. In certain embodiments, the carbocyclyl group is substituted C$_{3-10}$ carbocyclyl.

In some embodiments, "carbocyclyl" is a monocyclic, saturated carbocyclyl group having from 3 to 10 ring carbon atoms ("C$_{3-10}$ cycloalkyl"). In some embodiments, a cycloalkyl group has 3 to 8 ring carbon atoms ("C$_{3-8}$ cycloalkyl"). In some embodiments, a cycloalkyl group has 3 to 6 ring carbon atoms ("C$_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_5$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted C$_{3-10}$ cycloalkyl. In certain embodiments, the cycloalkyl group is substituted C$_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged, or spiro ring system, such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl, and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like.

Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 pi electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 pi electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl, and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl and refers to an optionally substituted alkyl group substituted by an optionally substituted heteroaryl group.

"Unsaturated" or "partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups). Likewise, "saturated" refers to a group that does not contain a double or triple bond, i.e., contains all single bonds.

Alkyl, alkenyl, alkynyl, carbocyclyl, heterocyclyl, aryl, and heteroaryl groups, which are divalent bridging groups, are further referred to using the suffix -ene, e.g., alkylene, alkenylene, alkynylene, carbocyclylene, heterocyclylene, arylene, and heteroarylene.

An atom, moiety, or group described herein may be unsubstituted or substituted, as valency permits, unless otherwise provided expressly. The term "optionally substituted" refers to substituted or unsubstituted.

A group is optionally substituted unless expressly provided otherwise. The term "optionally substituted" refers to being substituted or unsubstituted. In certain embodiments, alkyl, alkenyl, alkynyl, carbocyclyl, heterocyclyl, aryl, and heteroaryl groups are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present disclosure contemplates any and all such combinations in order to arrive at a stable compound. For purposes of this disclosure, heteroatoms such as nitrogen may have hydrogen substituents and/or any suitable substituent as described herein which satisfy the valencies of the heteroatoms and results in the formation of a stable moiety. In certain embodiments, the substituent is a carbon atom substituent. In certain embodiments, the substituent is a nitrogen atom substituent. In certain embodiments, the substituent is an oxygen atom substituent. In certain embodiments, the substituent is a sulfur atom substituent.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^\circledR$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ haloalkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups; wherein X$^-$ is a counterion;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ haloalkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{cc}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, $C_{1-10}$ alkyl, $C_{1-10}$ haloalkyl, $C_{1-10}$ perhaloalkyl, $C_{2-10}$ alkenyl, $C_{2-10}$ alkynyl, heteroC$_{1-10}$alkyl, heteroC$_{2-10}$ alkenyl, heteroC$_{2-10}$alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups; wherein $X^-$ is a counterion;

each instance of $R^{cc}$ is, independently, selected from hydrogen, $C_{1-10}$ alkyl, $C_{1-10}$ haloalkyl, $C_{1-10}$ perhaloalkyl, $C_{2-10}$ alkenyl, $C_{2-10}$ alkynyl, heteroC$_{1-10}$ alkyl, heteroC$_{2-10}$ alkenyl, heteroC$_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ haloalkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_2$-6alkynyl, $C_{3-10}$ carbocyclyl, 3-10 membered heterocyclyl, $C_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S; wherein $X^-$ is a counterion;

each instance of $R^{ee}$ is, independently, selected from $C_{1-6}$ alkyl, $C_{1-6}$ haloalkyl, $C_{1-6}$ perhaloalkyl, $C_{2-6}$ alkenyl, $C_{2-6}$ alkynyl, heteroC$_{1-6}$ alkyl, heteroC$_{2-6}$alkenyl, heteroC$_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of Ra is, independently, selected from hydrogen, $C_{1-6}$ alkyl, $C_{1-6}$ haloalkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, and 5-10 membered heteroaryl, or two R$^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^{30}$ X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)(OC$_{1-6}$ alkyl)$_2$, —P(=O)(C$_{1-6}$ alkyl)$_2$, —OP(=O)(C$_{1-6}$ alkyl)$_2$, —OP(=O)(OC$_{1-6}$ alkyl)$_2$, $C_{1-6}$ alkyl, $C_{1-6}$ haloalkyl, $C_{1-6}$ perhaloalkyl, $C_{2-6}$ alkenyl, $C_{2-6}$ alkynyl, heteroC$_{1-6}$alkyl, heteroC$_{2-6}$alkenyl, heteroC$_{2-6}$alkynyl, $C_{3-10}$ carbocyclyl, $C_{6-10}$ aryl, 3-10 membered heterocyclyl, 5-10 membered heteroaryl; or two geminal R$^{gg}$ substituents can be joined to form =O or =S; wherein $X^-$ is a counterion.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HCO$_3$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4$$^-$, PF$_4$$^-$, PF$_6$$^-$, AsF$_6$$^-$, SbF$_6$$^-$, B[3,5-(CF$_3$)$_2$C$_6$H$_3$]$_4$]$^-$, B(C$_6$F$_5$)$_4$$^-$, BPh$_4$$^-$, Al(OC(CF$_3$)$_3$)$_4$$^-$, and carborane anions (e.g., CB$_{11}$H$_{12}$$^-$ or (HCB$_{11}$Me$_5$Br$_6$)$^-$). Exemplary counterions which may be multivalent include CO$_3$$^{2-}$, HPO$_4$$^{2-}$, PO$_4$$^{3-}$, B$_4$O$_7$$^{2-}$, SO$_4$$^{2-}$, S$_2$O$_3$$^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes.

"Halo" or "halogen" refers to fluorine (fluoro, —F), chlorine (chloro, —Cl), bromine (bromo, —Br), or iodine (iodo, —I).

"Acyl" refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(OR$^{cc}$)$_2$, —P(=O)(R$^{aa}$)$_2$, —P(=O)(N(R$^{cc}$)$_2$)$_2$, C$_{1-10}$ alkyl, C$_{1-10}$ haloalkyl, C$_{1-10}$ perhaloalkyl, C$_{2-10}$ alkenyl, C$_{2-10}$ alkynyl, heteroC$_{1-10}$alkyl, heteroC$_{2-10}$ alkenyl, heteroC$_{2-10}$alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), (3-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $X^-$, $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-naphthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3^+X^-$, —$P(OR^{cc})_2$, —$P(OR^{cc})_3^+X^-$, —$P(=O)(R^{aa})_2$, —$P(=O)(OR^{cc})_2$, and —$P(=O)(N(R^{bb})_2)_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

As used herein, a "leaving group" (LG) is an art-understood term referring to a molecular fragment that departs with a pair of electrons in heterolytic bond cleavage, wherein the molecular fragment is an anion or neutral molecule. As used herein, a leaving group can be an atom or a group capable of being displaced by a nucleophile. See, for example, Smith, *March Advanced Organic Chemistry* 6th ed. (501-502). Exemplary leaving groups include, but are not limited to, halo (e.g., chloro, bromo, iodo) and activated substituted hydroxyl groups (e.g., —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein).

A "hydrocarbon chain" refers to a substituted or unsubstituted divalent alkyl, alkenyl, or alkynyl group. A hydrocarbon chain includes (1) one or more chains of carbon atoms immediately between the two radicals of the hydrocarbon chain; (2) optionally one or more hydrogen atoms on the chain(s) of carbon atoms; and (3) optionally one or more substituents ("non-chain substituents," which are not hydrogen) on the chain(s) of carbon atoms. A chain of carbon atoms consists of consecutively connected carbon atoms ("chain atoms") and does not include hydrogen atoms or heteroatoms. However, a non-chain substituent of a hydrocarbon chain may include any atoms, including hydrogen atoms, carbon atoms, and heteroatoms. For example, hydrocarbon chain —C$^A$H(C$^B$H$_2$C$^C$H$_3$)— includes one chain atom C$^A$, one hydrogen atom on C$^A$, and non-chain substituent —(C$^B$H$_2$C$^C$H$_3$). The term "C$_x$ hydrocarbon chain," wherein x is a positive integer, refers to a hydrocarbon chain that includes x number of chain atom(s) between the two radicals of the hydrocarbon chain. If there is more than one possible value of x, the smallest possible value of x is used for the definition of the hydrocarbon chain. For example, —CH(C$_2$H$_5$)— is a C$_1$ hydrocarbon chain, and

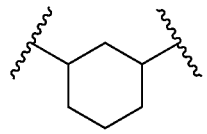 [SMILES: *C1CCCC(*)C1]

is a C$_3$ hydrocarbon chain. When a range of values is used, the meaning of the range is as described herein. For example, a C$_{3-10}$ hydrocarbon chain refers to a hydrocarbon chain where the number of chain atoms of the shortest chain of carbon atoms immediately between the two radicals of the hydrocarbon chain is 3, 4, 5, 6, 7, 8, 9, or 10. A hydrocarbon chain may be saturated (e.g., —(CH$_2$)$_4$—). A hydrocarbon chain may also be unsaturated and include one or more C=C and/or C≡C bonds anywhere in the hydrocarbon chain. For instance, —CH=CH—(CH$_2$)$_2$—, —CH$_2$—C≡C—CH$_2$—, and —C≡C—CH=CH— are all examples of a unsubstituted and unsaturated hydrocarbon chain. In certain embodiments, the hydrocarbon chain is unsubstituted (e.g., —C≡C— or —(CH$_2$)$_4$—). In certain embodiments, the hydrocarbon chain is substituted (e.g., —CH(C$_2$H$_5$)— and —CF$_2$—). Any two substituents on the hydrocarbon chain may be joined to form an optionally substituted carbocyclyl, optionally substituted heterocyclyl, optionally substituted aryl, or optionally substituted heteroaryl ring.

For instance,

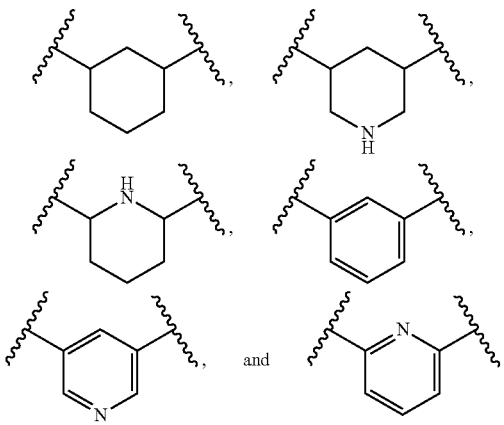

are all examples of a hydrocarbon chain. In contrast, in certain embodiments,

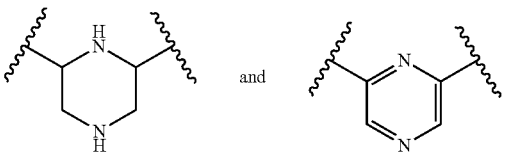 [SMILES: *C1CNCC(*)N1 ; *c1cncc(*)n1]

are not within the scope of the hydrocarbon chains described herein. When a chain atom of a C$_x$ hydrocarbon chain is replaced with a heteroatom, the resulting group is referred to as a C$_x$ hydrocarbon chain wherein a chain atom is replaced with a heteroatom, as opposed to a C$_{x-1}$ hydrocarbon chain. For example,

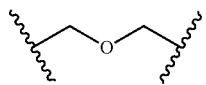 [SMILES: *COC*]

is a C$_3$ hydrocarbon chain wherein one chain atom is replaced with an oxygen atom.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds described herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

A "non-hydrogen group" refers to any group that is defined for a particular variable that is not hydrogen.

These and other exemplary substituents are described in more detail in the Detailed Description, Examples, and claims. The invention is not intended to be limited in any manner by the above exemplary listing of substituents.

Other Definitions

The following definitions are more general terms used throughout the present application.

As used herein, the term "salt" refers to any and all salts, and encompasses pharmaceutically acceptable salts.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula R·x $H_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates (R·0.5 $H_2O$)), and polyhydrates (x is a number greater than 1, e.g., dihydrates (R·2 $H_2O$) and hexahydrates (R·6 $H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof). All polymorphs have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphs of a compound can be prepared by crystallization under different conditions.

The term "prodrugs" refers to compounds that have cleavable groups and become by solvolysis or under physiological conditions the compounds described herein, which are pharmaceutically active in vivo. Such examples include, but are not limited to, choline ester derivatives and the like, N-alkylmorpholine esters and the like. Other derivatives of the compounds described herein have activity in both their acid and acid derivative forms, but in the acid sensitive form often offer advantages of solubility, tissue compatibility, or delayed release in the mammalian organism (see Bundgard, H., *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds described herein are particular prodrugs. In some cases it is desirable to prepare double ester type prodrugs such as (acyloxy)alkyl esters or ((alkoxycarbonyl)oxy)alkylesters. $C_1$-$C_8$alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds described herein may be preferred.

As used herein, the term "inhibit" or "inhibition," for example, in the context of promoting the degradation of a protein or enzyme, refers to a reduction in the amount of a target protein by promoting degradation of the protein. The reduction in the amount of the target protein thus reduces the level of the activity of the protein. As used herein, the term "inhibit" or "inhibition" in the context of DOT1L, for example, refers to a reduction in the level of activity of the DOT1L enzyme, for example, reducing the level of methyltransferase activity. In some embodiments, the term refers to a reduction in the level of DOT1L activity to a level that is statistically significantly lower than an initial level, which may, for example, be a baseline level of DOT1L activity. In some embodiments, the term refers to a reduction of the level of DOT1L activity to a level that is less than 75%, less than 50%, less than 40%, less than 30%, less than 25%, less than 20%, less than 10%, less than 9%, less than 8%, less than 7%, less than 6%, less than 5%, less than 4%, less than 3%, less than 2%, less than 1%, less than 0.5%, less than 0.1%, less than 0.01%, less than 0.001%, or less than 0.0001% of an initial level, which may, for example, be a baseline level of DOT1L activity.

When a compound, pharmaceutical composition, method, use, or kit is referred to as "selectively," "specifically," or "competitively" inhibiting a target (e.g., enzyme, methyltransferase, DOT1L), the compound, pharmaceutical composition, method, use, or kit inhibits the target enzyme, to a greater extent (e.g., not less than 2-fold, not less than 5-fold, not less than 10-fold, not less than 30-fold, not less than 100-fold, not less than 1,000-fold, or not less than 10,000-fold; and/or: not more than 2-fold, not more than 5-fold, not more than 10-fold, not more than 30-fold, not more than 100-fold, not more than 1,000-fold, or not more than 10,000-fold) than inhibiting a different target (e.g., enzyme, DOT1L).

The term "aberrant activity" refers to activity deviating from normal activity. In certain embodiments, the aberrant activity is increased activity. In certain embodiments, the aberrant activity is decreased activity. The term "increased activity" refers to activity higher than normal activity. The term "decreased activity" refers to activity lower than normal activity.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal. A "patient" refers to a human subject in need of treatment of a disease. The subject may also be a plant. In certain embodiments, the plant is a land plant. In certain embodiments, the plant is a non-vascular land plant. In certain embodiments, the plant is a vascular land plant. In certain embodiments, the plant is a seed plant. In certain embodiments, the plant is a cultivated plant. In certain embodiments, the plant is a dicot. In certain embodiments, the plant is a monocot. In certain embodiments, the plant is a flowering plant. In some embodiments, the plant is a cereal plant, e.g., maize, corn, wheat, rice, oat, barley, rye, or millet. In some embodiments, the plant is a legume, e.g., a bean plant, e.g., soybean plant. In some embodiments, the plant is a tree or shrub.

The term "biological sample" refers to any sample including tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

The term "tissue" refers to any biological tissue of a subject (including a group of cells, a body part, or an organ) or a part thereof, including blood and/or lymph vessels, which is the object to which a compound, particle, and/or composition of the invention is delivered. A tissue may be an abnormal or unhealthy tissue, which may need to be treated. A tissue may also be a normal or healthy tissue that is under a higher than normal risk of becoming abnormal or unhealthy, which may need to be prevented. In certain embodiments, the tissue is the central nervous system. In certain embodiments, the tissue is the brain.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms). Treatment may also be continued after symptoms have resolved, for example, to delay or prevent recurrence.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactic treatment. In certain embodiments, an effective amount is the amount of a compound described herein in a single dose. In certain embodiments, an effective amount is the combined amounts of a compound described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces, or avoids symptoms, signs, or causes of the condition, and/or enhances the therapeutic efficacy of another therapeutic agent. In certain embodiments, a therapeutically effective amount is an amount sufficient for binding a DOT1L protein. In certain embodiments, a therapeutically effective amount is an amount sufficient for treating a proliferative disease (e.g., cancer). In certain embodiments, a therapeutically effective amount is an amount sufficient for binding a DOT1L protein and/or inducing the degradation of the DOT1L protein.

A "prophylactically effective amount" of a compound described herein is an amount sufficient to prevent a condition, or one or more signs or symptoms associated with the condition, or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent. In certain embodiments, a prophylactically effective amount is an amount sufficient for binding a DOT1L protein, and/or inducing the degradation of the DOT1L protein. In certain embodiments, a prophylactically effective amount is an amount sufficient for treating a proliferative disease (e.g., cancer). In certain embodiments, a prophylactically effective amount is an amount sufficient for binding a DOT1L protein and/or binding the proteasome or a section of the proteasome (e.g., RPN13), and/or inducing the degradation of the DOT1L protein and treating a proliferative disease (e.g., cancer).

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary*, 25th ed.; Hensyl ed.; Williams & Wilkins: Philadelphia, 1990. Exemplary cancers include, but are not limited to, hematological malignancies. Additional exemplary cancers include, but are not limited to, lung cancer (e.g., bronchogenic carcinoma, small cell lung cancer (SCLC), non-small cell lung cancer (NSCLC), adenocarcinoma of the lung); kidney cancer (e.g., nephroblastoma, a.k.a. Wilms' tumor, renal cell carcinoma); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); heavy chain disease (e.g., alpha chain disease, gamma chain disease, mu chain disease; hemangioblastoma; hypopharynx cancer; inflammatory myofibroblastic tumors; immunocytic amyloidosis; liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than about 1,000 g/mol, not more than about 900 g/mol, not more than about 800 g/mol, not more than about 700 g/mol, not more than about 600 g/mol, not more than about 500 g/mol, not more than about 400 g/mol, not more than about 300 g/mol, not more than about 200 g/mol, or not more than about 100 g/mol. In certain embodiments, the molecular weight of a small molecule is at least about 100 g/mol, at least about 200 g/mol, at least about 300 g/mol, at least about 400 g/mol, at least about 500 g/mol, at least about 600 g/mol, at least about 700 g/mol, at least about 800 g/mol, or at least about 900 g/mol, or at least about 1,000 g/mol. Combinations of the above ranges (e.g., at least about 200 g/mol and not more than about 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include, but are not limited to, radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

The term "therapeutic agent" refers to any substance having therapeutic properties that produce a desired, usually beneficial, effect. For example, therapeutic agents may treat, ameliorate, and/or prevent disease. Therapeutic agents, as disclosed herein, may be biologics or small molecule therapeutics.

The term "E3 ubiquitin ligase" or "E3 ligase" refers to any protein that recruits an E2 ubiquitin-conjugating enzyme that has been loaded with ubiquitin, recognizes a protein substrate, and assists or directly catalyzes the transfer of ubiquitin from the E2 protein to the protein substrate. For E3 ubiquitin ligase, exemplary sequences for GenBank: ACH72645.1 (*Homo sapiens*) include: MESGGRPSLC QFILLGTTSV VTAALYSVYR QKARVSQELK GAKKVHLGED LKSILSEAPG KCVPYAVIEG AVRSVKETLN SQFVENCKGV IQRLTLQEHK MVWNRTTHLW NDCSKIIHQR TNTVPFDLVP HEDGVDVAVR VLKPLDSVDL GLETVYEKFH PSIQSFTDVI GHYISGERPK GIQETEEMLK VGATLTGVGE LVLDNNSVRL QPPKQGMQYY LSSQDFDSLL QRQESSVRLW KVLALVFGFA TCATLF-FILR KQYLQRQERL RLKQMQEEFQ EHEAQLLSRA KPEDRESLKS ACVVCLSSFK SCVFLECGHV CSCTECYRAL PEPKKCPICR QAITRVIPPY NS (SEQ ID NO: 1). FOR E3 UBIQUITIN LIGASE, EXEMPLARY SEQUENCES FOR GENBANK: AAP47175.1 (*Homo sapiens*) INCLUDE: MEEGNNNEEV IHLNNFHCHR GQEWINLRDG PITISDSSDE ERIPMLVTPA PQQHEEEDLD DDVILTETNK PQRSRPNLIK PAAQWQDLKR LGEERPKKSR AAFESDKSSY FSVCNNPLFD SGAQDDSEDD YGEFLDLGPP GISEFTKPSG QTEREPKPGP SHNQAANDIV NPRSEQKVII LEEGSLLYTE SDPLETQNQS SEDSETELLS NLGESAALAD DQAIEEDCWL DHPYFQSLNQ QPREITNQVV PQERQPEAEL GRLLFQHEFP GPAFPRPEPQ QGGISGPSSP QPAHPLGEFE DQQLASDDEE PGPAFPMQES QEPNLENIWG QEAAEVDQEL VELLVKETEA RFPDVANGFI EEIIHFKNYY DLNVLCNFLL ENPDYPKRED RIIINPSSSL LASQDETKLP KIDFFDYSKL TPLDQRCFIQ AADLLMADFK VLSSQDIKWA LHELKGHYAI TRKALSDAIK KWQELSPETS GKRKKRKQMN QYSYIDFKFE QGDIKIEKRM FFLENKRRHC RSYDRRALLP AVQQEQEFYE QKIKEMAEHE DFLLALQMNE EQYQKDGQLI ECRCCYGEFP FEELTQCADA HLFCKECLIR YAQEAVFGSG KLELSCMEGS CTCSFPTSEL EKVLPQTILY KYYERKAEEE VAAAYADELV RCPSCSFPAL LDSDVKRFSC PNPHCRKETC RKCQGLWKEH NGLTCEELAE KDDIKYRTSI EEKMTAARIR KCHKCGTGLI KSEGCNRMSC RCGAQMCYLC RVSINGYDHF CQHPRSPGAP CQECSRCSLW TDPTEDDEKL IEEIQKEAEE EQKRKNGENT FKRIGPPLEK PVEKVQRVEA LPRPVPQNLP QPQMPPYAFA HPPFPLPPVR PVFNNFPLNM GPIPAPYVPP LPNVRVNYDF GPIHMPLEHN LPMHFGPQPR HRF (SEQ ID NO: 2). For E3 ubiquitin ligase, exemplary sequences for GenBank: AAP47174.1 (*Homo sapiens*) include: MEEGNNNEEV IHLNNFHCHR GQEWINLRDG PITISDSSDE ERIPMLVTPA PQQHEEEDLD DDVILTEDDS EDDYGEFLDL GPPGISEFTK PSGQTEREPK PGPSHNQAAN DIVNPRSEQK VIILEEGSLL YTESDPLETQ NQSSEDSETE LLSNLGESAA LADDQAIEED CWLDHPYFQS LNQQPREITN QVVPQERQPE AELGRLLFQH EFPGPAFPRP EPQQGGISGP SSPQPAHPLG EFEDQQLASD DEEPGPAFPM QESQEPNLEN IWGQEAAEVD QELVELLVKE TEARFPDVAN GFIEEIIHFK NYYDLNVLCN FLLENPDYPK REDRIIINPS SSLLASQDET KLPKIDFFDY SKLTPLDQRC FIQAADLLMA DFKVLSSQDI KWALHELKGH YAITRKALSD AIKKWQELSP ETSGKRKKRK QMNQYSYIDF KFEQGDIKIE KRMFFLENKR RHCRSYDRRA LLPAVQQEQE FYEQKIKEMA EHEDFLLALQ MNEEQYQKDG QLIECRCCYG EFPFEELTQC ADAHLFCKEC LIRYAQEAVF GSGKLELSCM EGSCTCSFPT SELEKVLPQT ILYKYYERKA EEEVAAAYAD ELVRCPSCSF PALLDSDVKR FSCPNPHCRK ETCRKCQGLW KEHNGLTCEE LAEKDDIKYR TSIEEKMTAA RIRKCHKCGT GLIKSEGCNR MSCRCGAQMC YLCRVSINGY DHFCQHPRSP GAPCQECSRC SLWTDPTEDD EKLIEEIQKE AEEEQKRKNG ENTFKRIGPP LEKPVEKVQR VEALPRPVPQ NLPQPQMPPY AFAHPPFPLP PVRPVFNNFP LNMGPIPAPY VPPLPNVRVN YDFGPIHMPL EHNLPMHFGP QPRHRF (SEQ ID NO: 3).

The term "ubiquitin RPN13 receptor," "26S Proteasome regulatory subunit Rpn13," "RPN13," or "Proteasomal ubiquitin receptor ADRM1" refers to a protein encoded by the ADRM1 gene. The ubiquitin RPN13 receptor is a subunit of the 19S proteasome complex.

"Histone methyltransferases" or "HMTs" are histone-modifying enzymes that catalyze the transfer of one, two, or three methyl groups to lysine and/or arginine residues of histone proteins. HMTs modify histones at certain sites through methylation. Methylation of histones is of biological significance because such methylation is a principal epigenetic modification of chromatin that determines gene expression, genomic stability, stem cell maturation, cell lineage development, genetic imprinting, DNA methylation, and/or cell mitosis. In certain embodiments, an HMT described herein is DOT1L (Disruptor of telomeric silencing 1-like, histone H3K79 methyltransferase).

The term "binder" refers to a compound that binds to a protein. The binder binds to a protein with a $K_d$ of less than 50,000 nM, less than 20,000 nM, less than 10,000 nM, less than 5,000 nM, less than 2,500 nM, less than 1,000 nM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, less than 4 nM, less than 3 nM, less than 2 nM, or less than 1 nM.

The term "proteasome" refers to a multisubunit enzyme complex that plays a key role regulating proteins that control cell-cycle progression and apoptosis. The proteasome conducts proteolysis of selected proteins.

The term "DOT1L" or "Disruptor of telomeric silencing 1-like histone H3K79 methyltransferase" refers to an enzyme that is encoded by the DOT1L gene. DOT1L is a histone methyltransferase that methylates lysine-79 of histone H3. DOT1L is inactive against free core histones but shows significant histone methyltransferase activity against nucleosomes. For DOT1L, an exemplary GenBank (*Homo sapiens*) accession ID is: NP_115871.

BRIEF DESCRIPTION OF THE DRAWINGS

FIG. 3 also shows a schematic depicting two different pathways of a polyubiquitinated protein wherein degradation of the protein by the proteasome leads to a healthy tumor cell, and conversely, inhibition of the proteasome using an exemplary compound which includes RA190 leads to toxic accumulation of the polyubiquitinated protein, and a dead tumor cell. The present disclosure does not involve the second pathway—inhibition of the proteasome. The compound binding does not dislocate RPN13 from the proteasome. The compound is used to recruit targeted protein directly to proteasome for selective degradation.

FIG. 6A shows a crystal structure of the interaction between the DOT1L protein and an exemplary DOT1L degrader compound. FIG. 6B shows a closer view of the crystal structure of the interaction between the DOT1L protein and an exemplary DOT1L degrader compound. FIG. 6C shows a detailed description of the various portions of an exemplary DOT1L degrader that involves linkages between RA190 and the DOT1L binder at different positions.

FIGS. 9A-9C show a biochemical assay for detecting the target inhibitors that can disrupt the binding of RPN13 with poly-ubiquitinylation. FIG. 9A portrays a biochemical assay for detecting the target inhibitors that can disrupt the binding of RPN13 with poly-ubiquitinylation. FIG. 9B shows the optimization of the assay. FIG. 9C shows that compound RA190 can disrupt the binding, and create the alpha signal.

FIGS. 10A-10C show exemplary DOT1L degraders. FIG. 10A shows an exemplary DOT1L degrader (dDOT1L-6). FIG. 10B shows an exemplary DOT1L degrader (dDOT1L-7). FIG. 10C shows an exemplary DOT1L degrader (dDOT1L-8).

FIGS. 12A-12D show the relative cell growth (%), based on a cell count of acute myeloid leukemia cells upon the treatment of Molm13 PA cells, Molm13 RE cells, and human leukemia (HL60; as negative control) cells with exemplary DOT1L degraders at various concentrations in for 10 days. FIG. 12A shows the results of cells treated with exemplary DOT1L degrader DOT1L-6. FIG. 12B shows the results of cells treated with exemplary DOT1L degrader DOT1L-7. FIG. 12C shows the results of cells treated with exemplary DOT1L degrader DOT1L-8. FIG. 12D shows the results on day 3 of cells treated with exemplary DOT1L inhibitor RA190 (used as a control).

DETAILED DESCRIPTION OF CERTAIN EMBODIMENTS OF THE INVENTION

Figure 1:
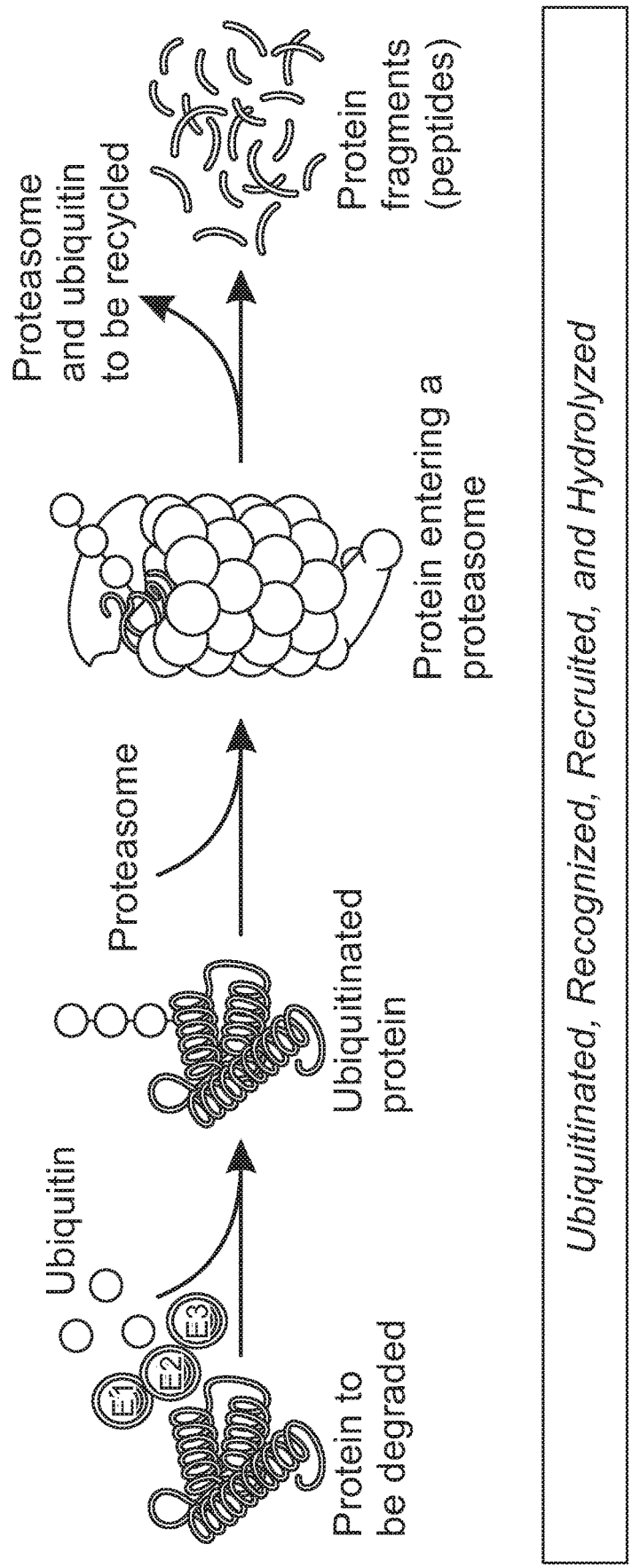
FIG. 1 shows a schematic of RPN13-linked protein degradation, in which the target protein is recruited by RPN13, a ubiquitin receptor protein to the proteasome. The protein enters the proteasome and then is hydrolyzed.
Figure 2:
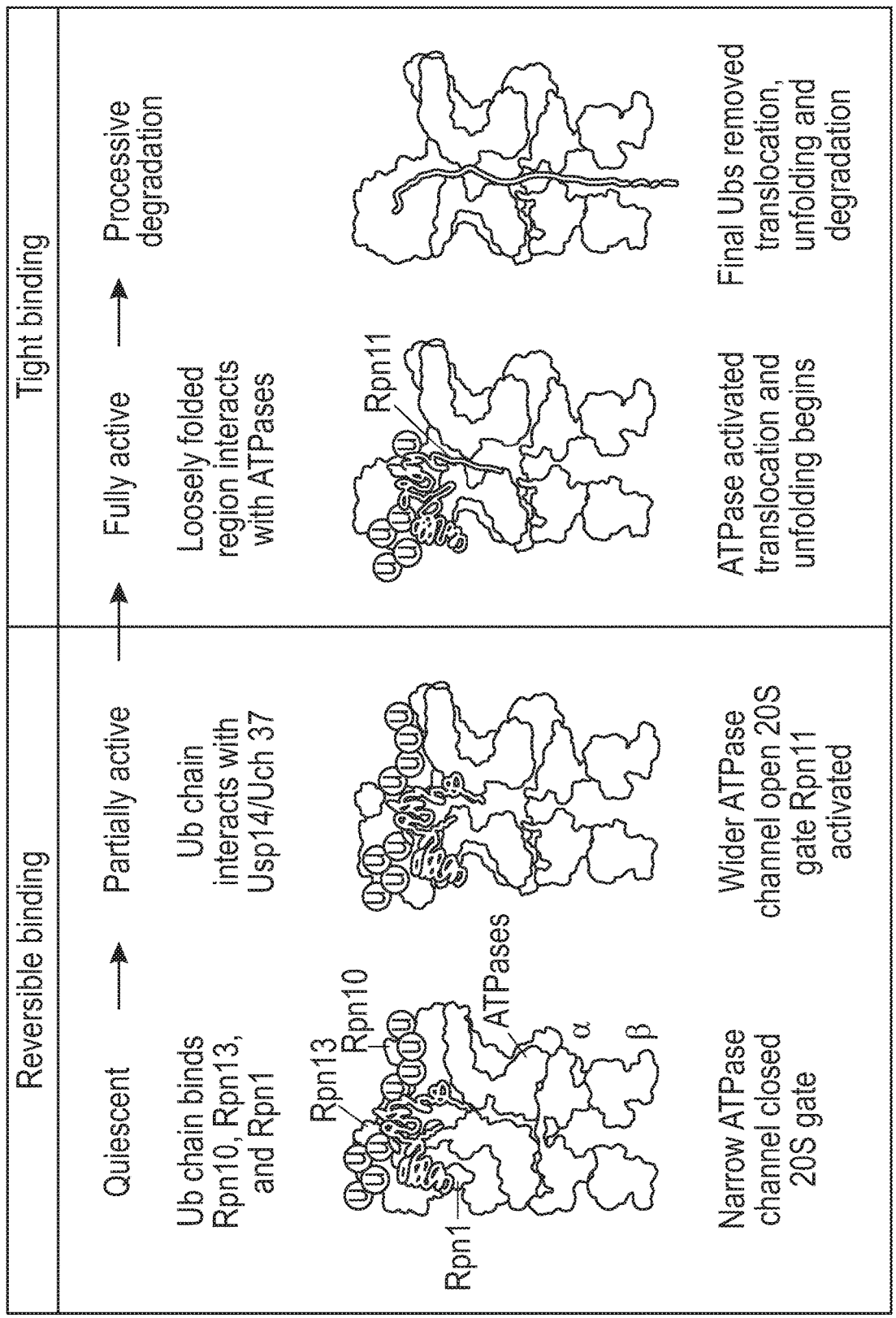
FIG. 2 shows a schematic of the RPN13 function in binding and in recognition to recruit a poly-ubiquitinylated protein into the proteasome.
Figure 3:
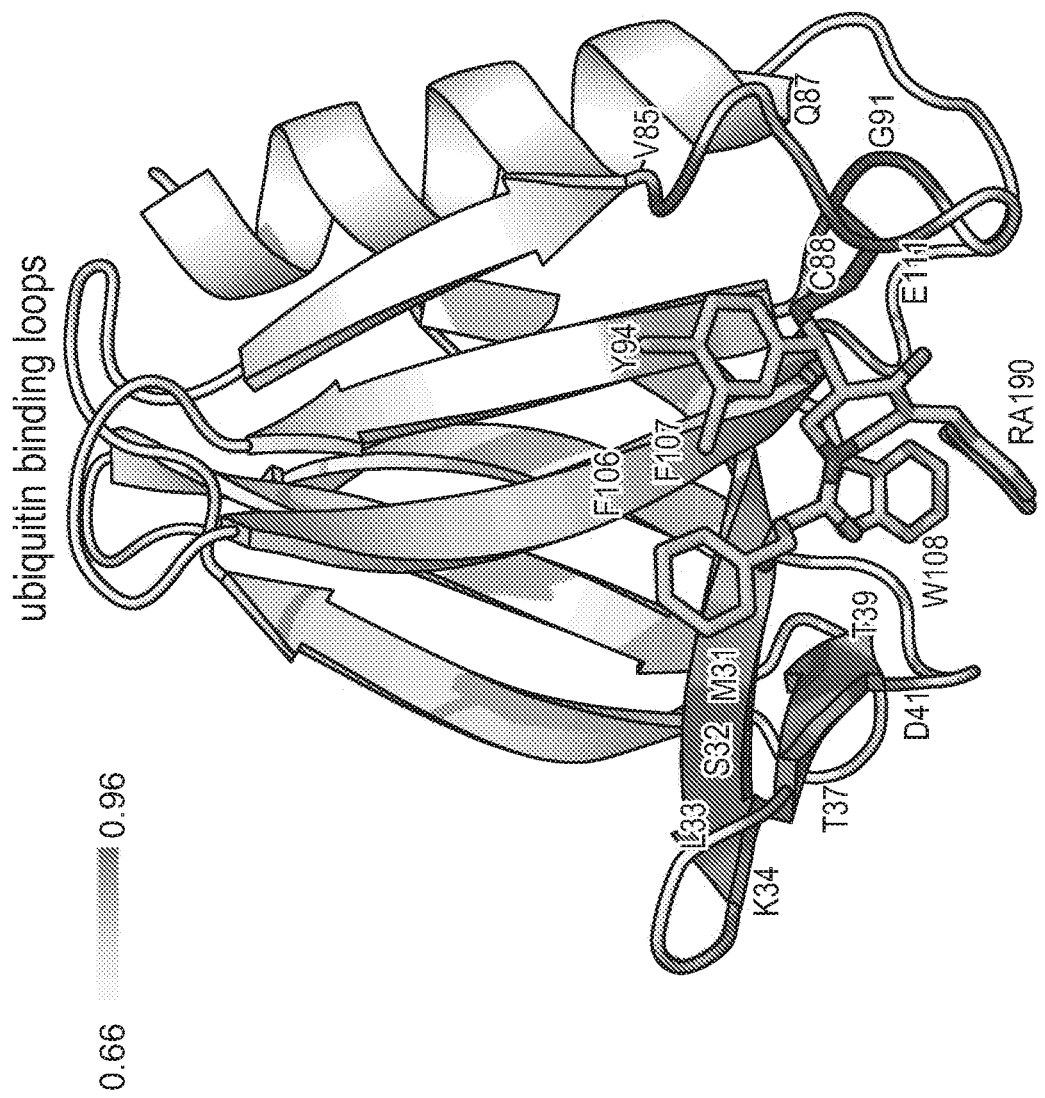
FIG. 3 shows a NMR structure of compound RA190 binding to RPN13.
Figure 3:
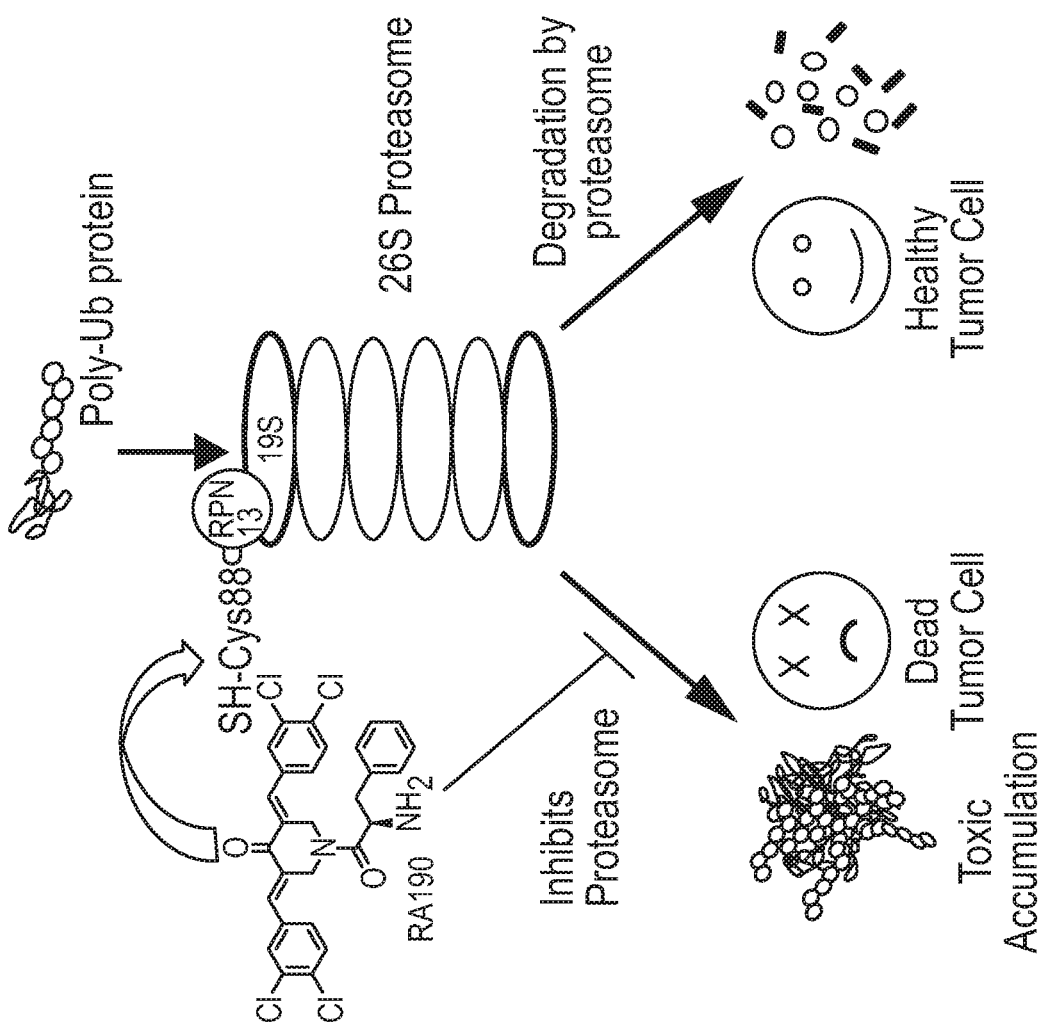
Figure 4:
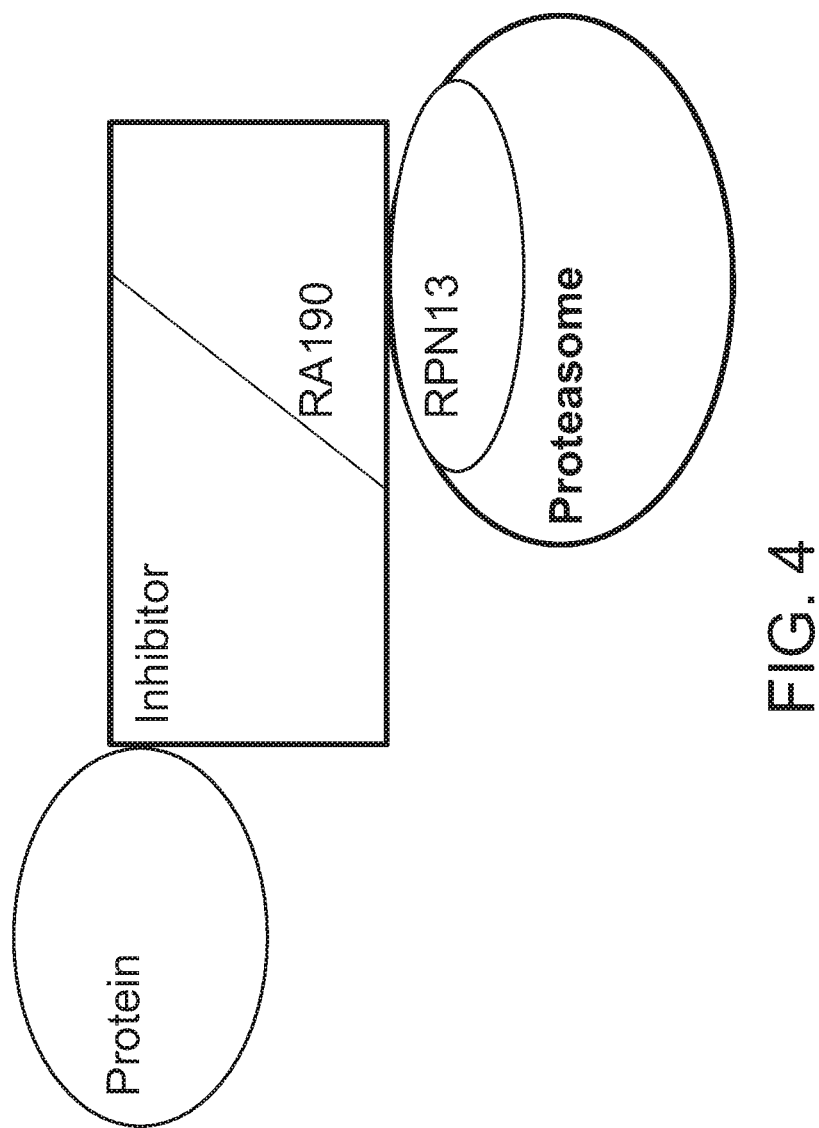
FIG. 4 shows a schematic depicting an exemplary compound which includes RA190 (a binder of the ubiquitin receptor RPN13), wherein the compound promotes the degradation of a target protein by proteasomal degradation.
Figure 5:
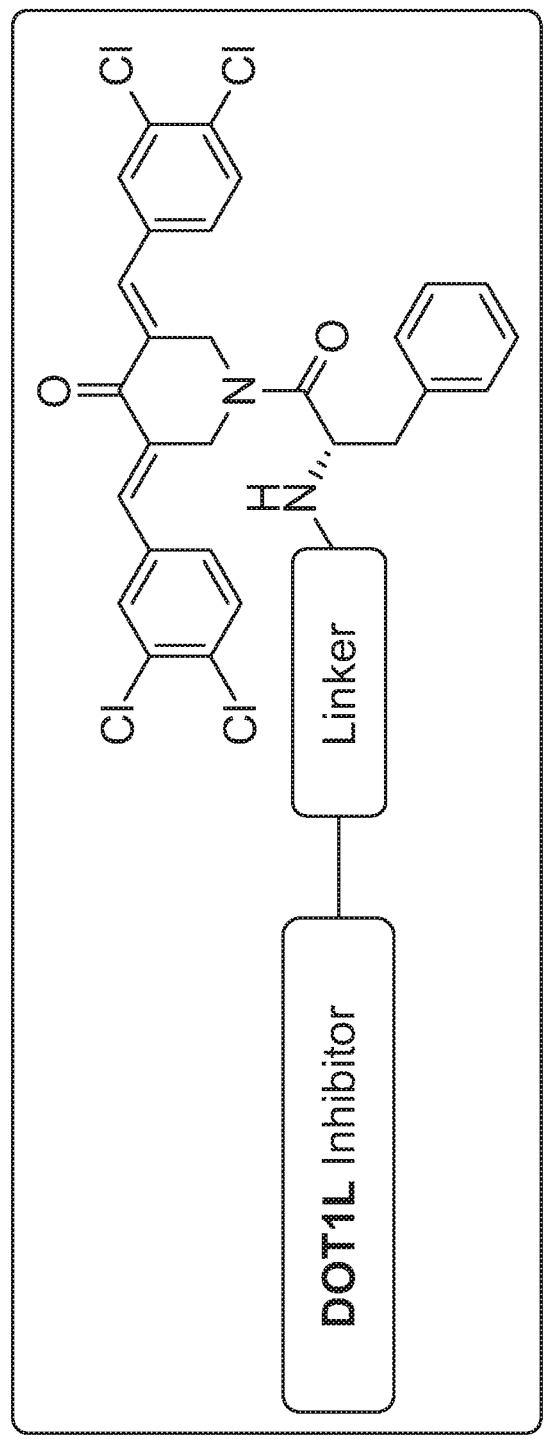
FIG. 5 shows an exemplary compound which includes a DOT1L inhibitor connected to RA190 via a linker.
Figure 6A:
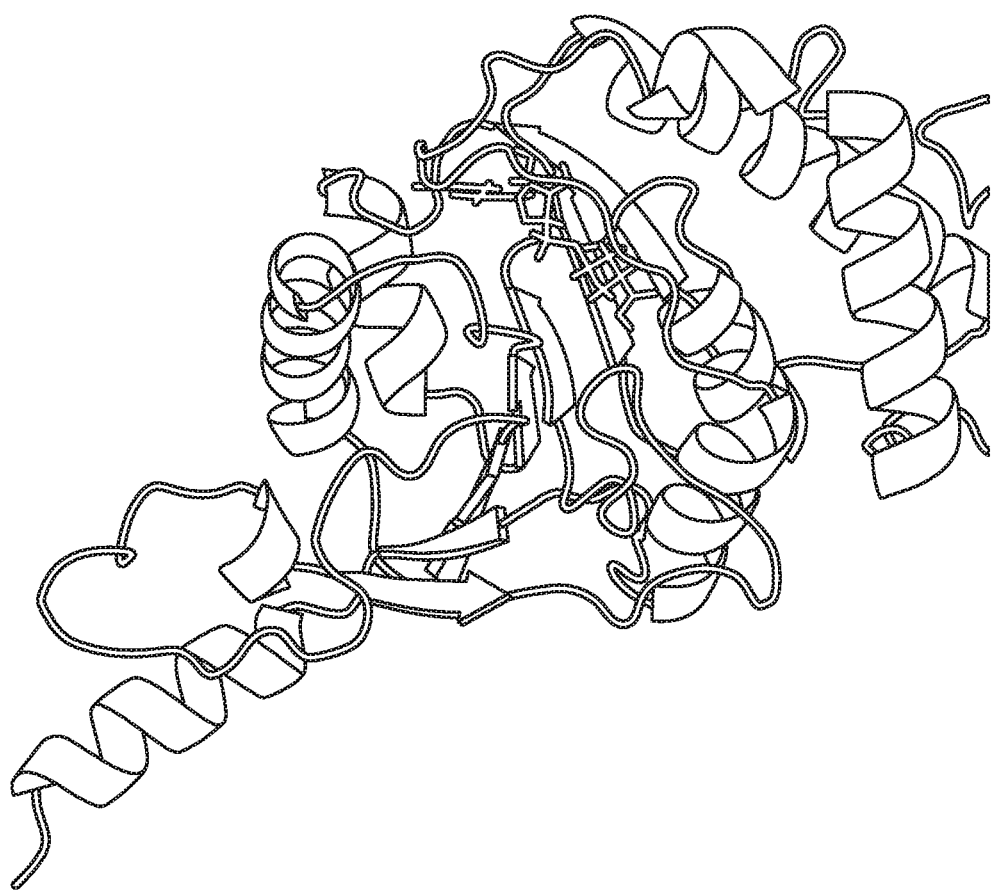
FIGS. 6A-6C show the degradation of DOT1L using an exemplary DOT1L degrader compound.
Figure 6B:
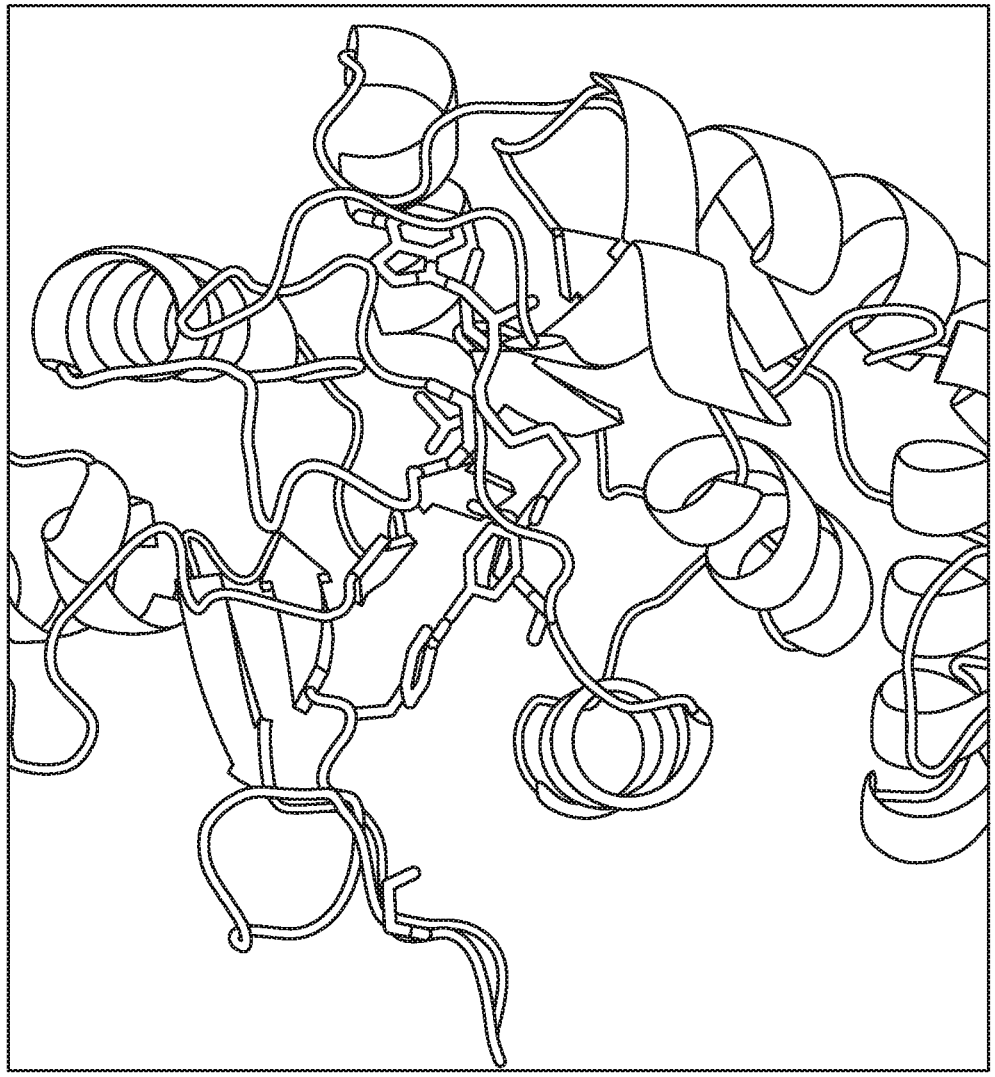
Figure 6C:
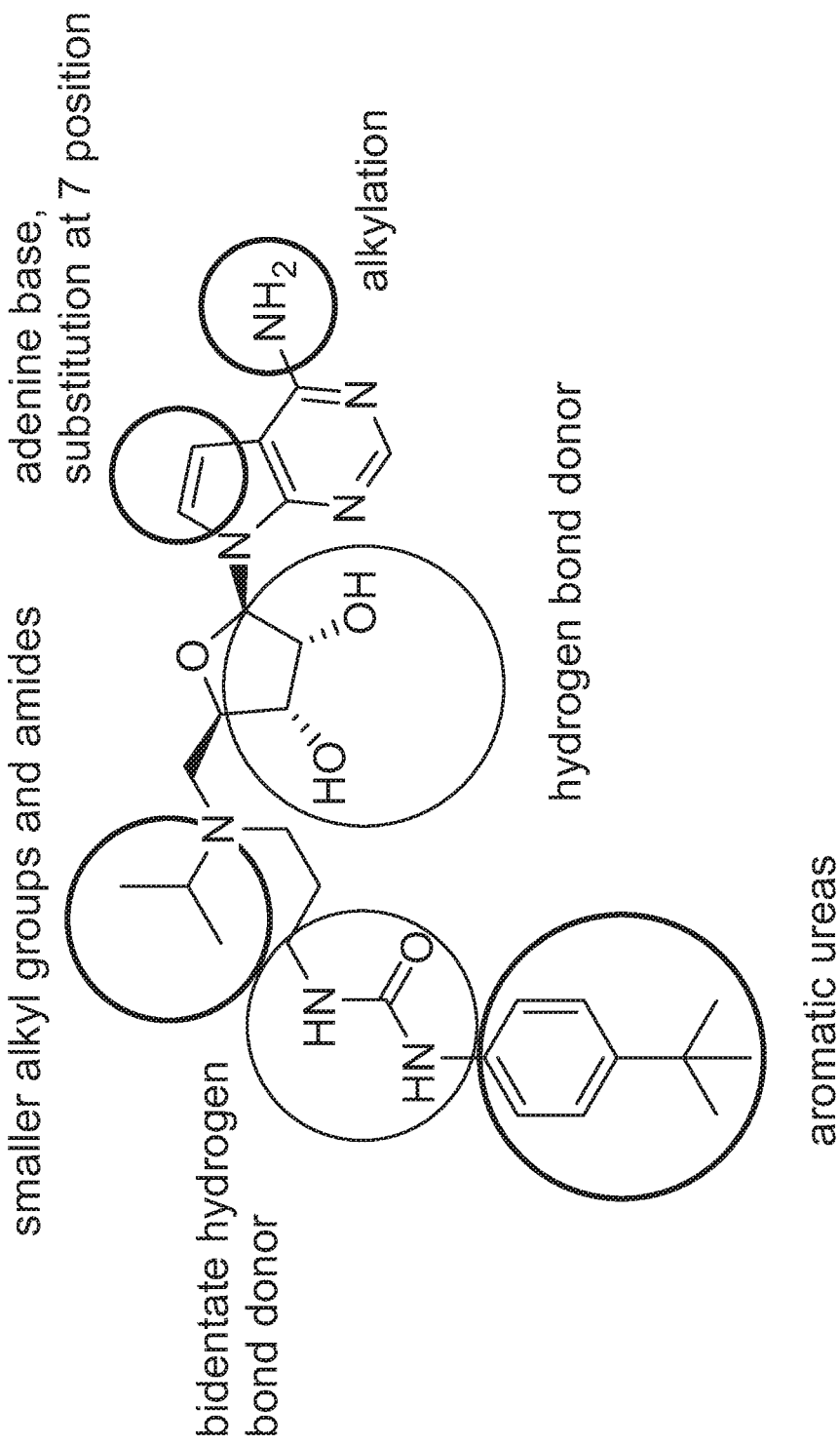
Figure 7:
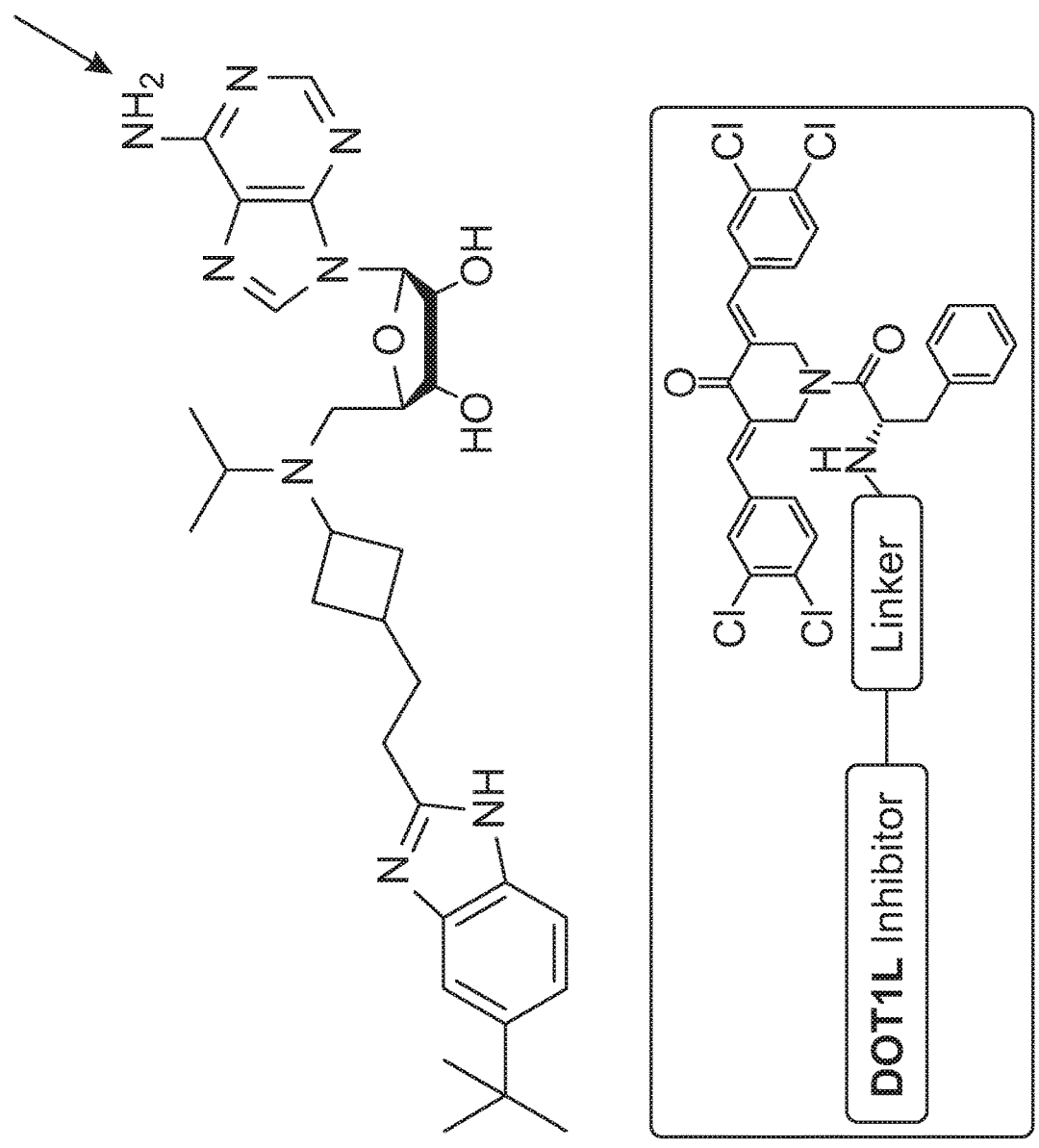
FIG. 7 shows the design principles behind the portions of exemplary, RPN13-based DOT1L degraders.
Figure 8:
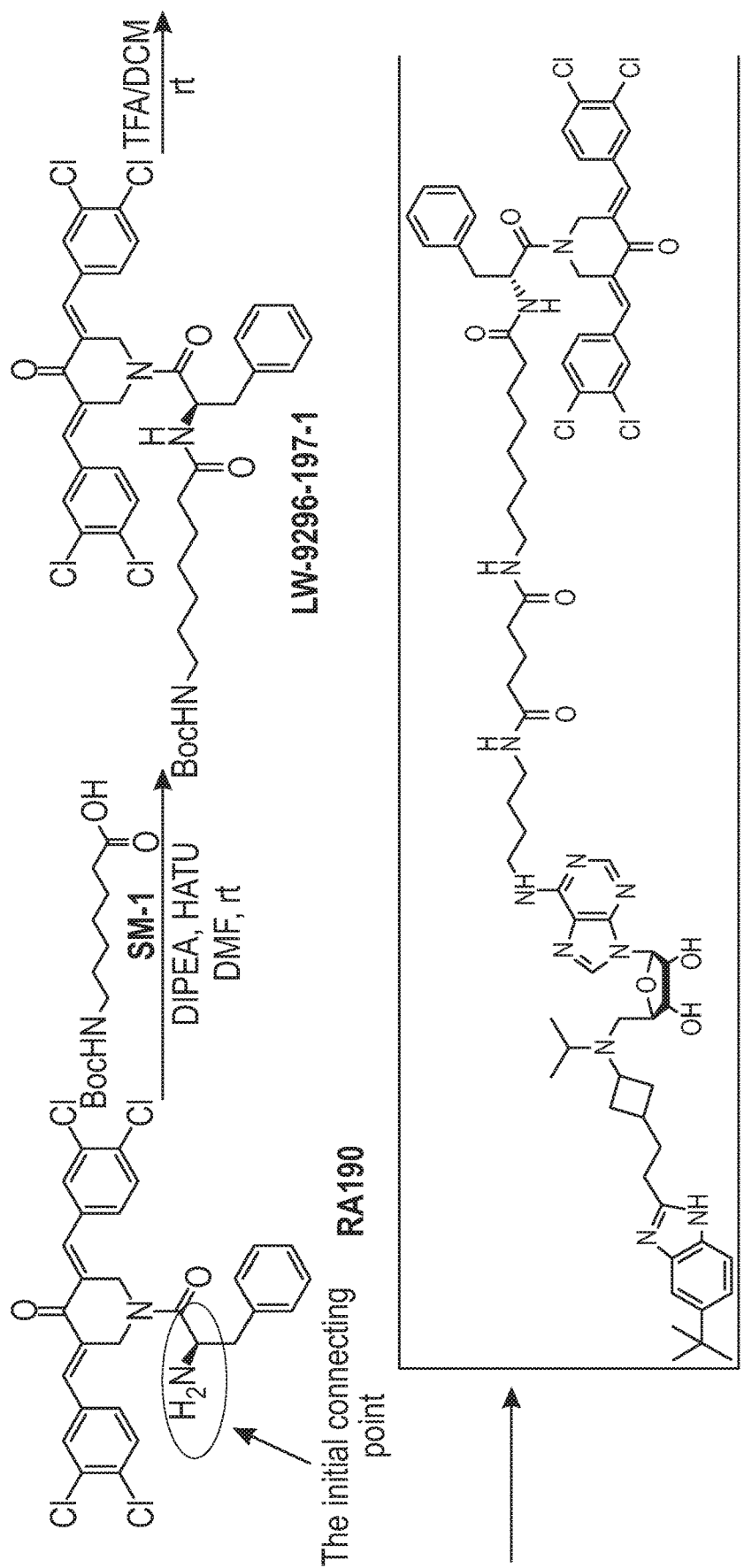
FIG. 8 shows an exemplary synthetic scheme for synthesizing an exemplary DOT1L degrader which includes a DOT1L inhibitor linked to RA190 via a linker.

The bifunctional compounds described herein interact with the target protein DOT1L and the ubiquitin receptor RPN13 (ADRM1). As described herein, without wishing to be bound by any particular theory, the therapeutic effect may be the result of degradation, modulation, or binding of the target (i.e., DOT1L) by a compound described herein. The therapeutic effect may be a result of the bifunctional compound, which includes a binder of the ubiquitin receptor RPN13, bringing the target protein DOT1L to the proteasome, thereby inducing the degradation of DOT1L. In certain embodiments, the compounds described herein selectively bind and degrade DOT1L over other proteins (e.g., other methyltransferases).

In certain embodiments, bifunctional compounds of Formula (I) are bifunctional compounds derived from the RA190-based compounds which bind RPN13 and inhibit proteasome function described in U.S. patent application Ser. No. 14/889,768, filed May 6, 2014, issued as U.S. Pat. No. 9,913,834, on Mar. 13, 2018, which is incorporated herein by reference.

In certain embodiments, the compounds that bind to RPN13 are compounds derived from the RPN13-binding compounds described in U.S. patent application Ser. No. 14/889,768, filed May 6, 2014, issued as U.S. Pat. No. 9,913,834, on Mar. 13, 2018, which is incorporated herein by reference.

In one aspect, disclosed are compounds of Formula (I):

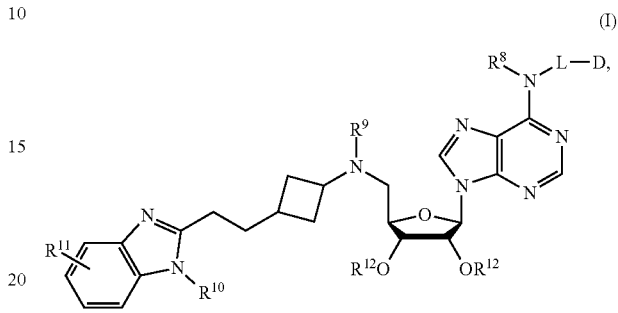

or a pharmaceutically acceptable salt, co-crystal, tautomer, stereoisomer, solvate, hydrate, polymorph, isotopically enriched derivative, or prodrug thereof, wherein:

$R^8$ is hydrogen, optionally substituted acyl, optionally substituted alkyl, or a nitrogen protecting group;

$R^9$ is hydrogen, optionally substituted acyl, optionally substituted alkyl, or a nitrogen protecting group;

$R^{10}$ is hydrogen, optionally substituted acyl, optionally substituted alkyl, or a nitrogen protecting group;

$R^{11}$ is halogen, optionally substituted acyl, or optionally substituted alkyl; each instance of $R^{12}$ is independently hydrogen, optionally substituted acyl, or an oxygen protecting group;

L is a linker; and

D is a binder of the ubiquitin receptor RPN13.

Compounds of Formula (I) are bifunctional compounds that bind to the target protein DOT1L on one end and bind to ubiquitin receptor RPN13 on the other end.

Substituents $R^8$, $R^9$, $R^{10}$, $R^{11}$, and $R^{12}$

For compounds of Formula (I), the DOT1L binding moiety includes substituents $R^8$, $R^9$, $R^{10}$, $R^{11}$, and $R^{12}$.

In certain embodiments, $R^8$ is hydrogen. In certain embodiments, $R^8$ is optionally substituted acyl (e.g., —C(═O)Me). In certain embodiments, $R^8$ is optionally substituted alkyl (e.g., optionally substituted $C_{1-6}$ alkyl). In certain embodiments, $R^8$ is optionally substituted methyl or optionally substituted ethyl. In certain embodiments, $R^8$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, $R^9$ is hydrogen. In certain embodiments, $R^9$ is optionally substituted acyl (e.g., —C(═O)Me). In certain embodiments, $R^9$ is optionally substituted alkyl (e.g., optionally substituted $C_{1-6}$ alkyl). In certain embodiments, $R^9$ is optionally substituted methyl or optionally substituted ethyl. In certain embodiments, $R^9$ is optionally substituted n-propyl. In certain embodiments, $R^9$ is optionally substituted isopropyl. In certain embodiments, $R^9$ is unsubstituted isopropyl. In certain embodiments, $R^9$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R¹⁰ is hydrogen. In certain embodiments, R¹⁰ is optionally substituted acyl (e.g., —C(=O)Me). In certain embodiments, R¹⁰ is optionally substituted alkyl (e.g., optionally substituted $C_{1-6}$ alkyl). In certain embodiments, R¹⁰ is optionally substituted methyl or optionally substituted ethyl. In certain embodiments, R⁹ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, R¹¹ is halogen (e.g., F, Cl, Br, or I). In certain embodiments, R¹¹ is optionally substituted acyl (e.g., —C(=O)Me). In certain embodiments, R¹¹ is optionally substituted alkyl (e.g., optionally substituted $C_{1-6}$ alkyl). In certain embodiments, R¹¹ is optionally substituted $C_{1-6}$ alkyl. In certain embodiments, R¹¹ is optionally substituted methyl or optionally substituted ethyl. In certain embodiments, R¹¹ is optionally substituted n-propyl. In certain embodiments, R¹¹ is optionally substituted isopropyl. In certain embodiments, R¹¹ is unsubstituted isopropyl. In certain embodiments, R¹¹ is optionally substituted butyl. In certain embodiments, R¹¹ is optionally substituted t-butyl. In certain embodiments, R¹¹ is unsubstituted t-butyl.

In certain embodiments, at least one instance of R¹² is hydrogen. In certain embodiments, at least one instance of R¹² is optionally substituted acyl (e.g., —C(=O)Me). In certain embodiments, at least one instance of R¹² is an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), methanesulfonate (mesylate), benzylsulfonate, and tosylate (Ts)). In certain embodiments, both instances of R¹² are hydrogen. In certain embodiments, one instance of R¹² is hydrogen and the instance of R¹² is optionally substituted acyl (e.g., —C(=O)Me). In certain embodiments, one instance of R¹² is hydrogen and the instance of R¹² is an oxygen protecting group (e.g., methyl, methoxylmethyl (MOM), trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), methanesulfonate (mesylate), benzylsulfonate, and tosylate (Ts)).

In certain embodiments, a compound of Formula (I) is of formula:

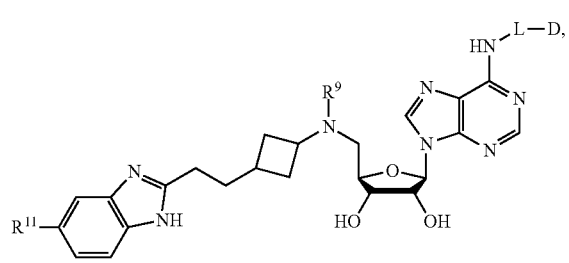

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of formula:

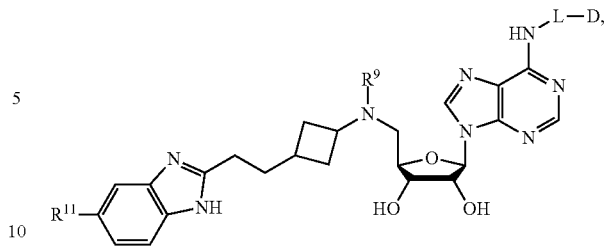

or a pharmaceutically acceptable salt thereof.

In certain embodiments, a compound of Formula (I) is of formula:

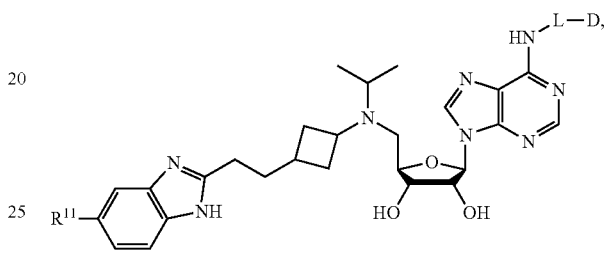

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of formula:

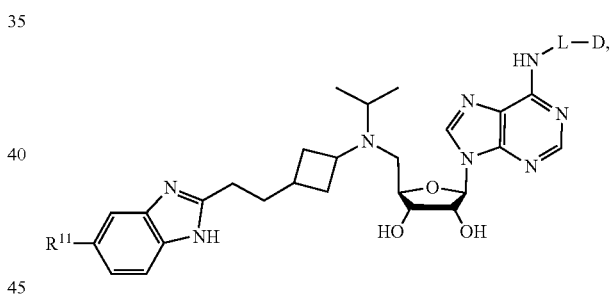

or a pharmaceutically acceptable salt thereof.

In certain embodiments, a compound of Formula (I) is of formula:

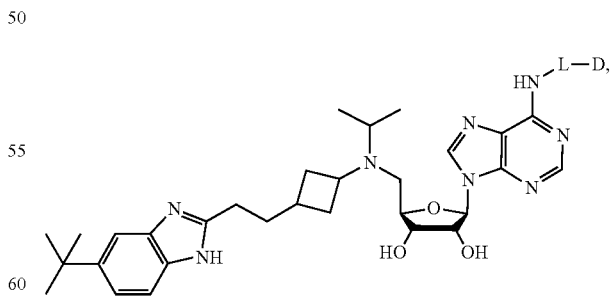

or a pharmaceutically acceptable salt, solvate, hydrate, polymorph, co-crystal, tautomer, stereoisomer, isotopically labeled derivative, or prodrug thereof.

In certain embodiments, a compound of Formula (I) is of formula:

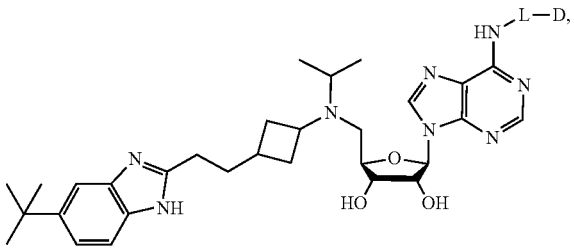

or a pharmaceutically acceptable salt thereof.
Group D
Substituents A, Y, Z, and $R^7$ In certain embodiments, D is a binder of the ubiquitin receptor RPN13. In certain embodiments, D is of the formula:

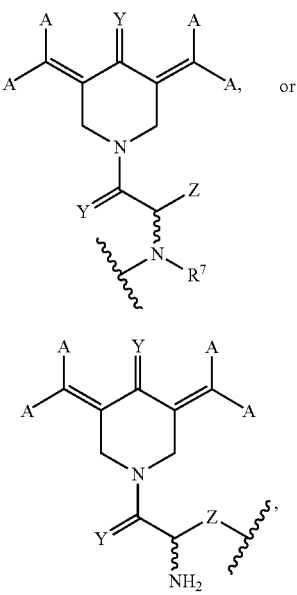

wherein:
in each pair of A's, one A is hydrogen, and the other A is one of:
(i) phenyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
(ii) naphthyl, optionally substituted with 1-5 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;
(iii) a 5- or 6-membered monocyclic heteroaryl group, having 1-3 heteroatoms selected from the group consisting of O, N, and S, optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$; and
(iv) an 8- to 10-membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of $R^1$, $OR^1$, $NR^1R^2$, $S(O)_qR^1$, $SO_2R^1R^2$, $NR^1SO_2R^2$, $C(O)R^1$, $C(O)OR^1$, $C(O)NR^1R^2$, $NR^1C(O)R^2$, $NR^1C(O)OR^2$, $CF_3$, and $OCF_3$;

wherein Y is $=O$, $=S$, $=NR^1$, or $=CR^1R^2$, and wherein $R^1$ and $R^2$ are selected from the group consisting of hydrogen, nitro, hydroxyl, carboxy, amino, halogen, cyano, and $C_1$-$C_{14}$ linear or branched alkyl groups, that are optionally substituted with 1-3 substituents selected from the group consisting of $C_1$-$C_{14}$ linear or branched alkyl, up to perhalo substituted $C_1$-$C_{14}$ linear or branched alkyl, $C_1$—$C_{14}$ alkoxy, hydrogen, nitro, hydroxyl, carboxy, amino, $C_1$-$C_{14}$ alkylamino, $C_1$-$C_{14}$ dialkylamino, halogen, and cyano;

wherein $R^7$ is hydrogen, $C_{1-6}$ alkyl, or a nitrogen protecting group;

wherein Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; $(CH_2)_q$—K, wherein K is a 5- or 6-membered monocyclic heterocyclic ring, containing 1 to 4 atoms selected from oxygen, nitrogen, and sulfur, which is saturated, partially saturated, or aromatic, or an 8- to 10-membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4.

In certain embodiments, D is of the formula:

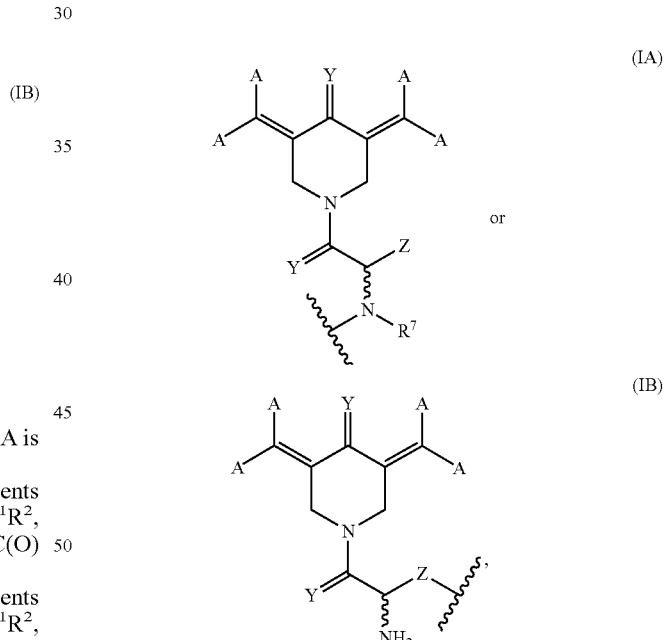

wherein:
for each set of two moieties A bound to the same carbon atom, one A is hydrogen, and the other A is one of:
(i) phenyl, optionally substituted with 1-5 substituents selected from the group consisting of —$R^1$, —$OR^1$, —$NR^1R^2$, —$S(O)_qR^1$, —$SO_2R^1R^2$, —$NR^1SO_2R^2$, —$C(O)R^1$, —$C(O)OR^1$, —$C(O)NR^1R^2$, —$NR^1C(O)R^2$, —$NR^1C(O)OR^2$, —$CHF_2$, —$CH_2F$, —$CF_3$, and —$OCF_3$;
(ii) naphthyl, optionally substituted with 1-5 substituents selected from the group consisting of —$R^1$, —$OR^1$, —$NR^1R^2$, —$S(O)_qR^1$, —$SO_2R^1R^2$, —$NR^1SO_2R^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$;

(iii) a 5- or 6-membered monocyclic heteroaryl group, having 1-3 heteroatoms selected from the group consisting of O, N, and S, optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$; and (iv) an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$;

Y is =O, =S, =NR$^1$, or =CR$^1$R$^2$,

R$^1$ and R$^2$ are each independently selected from the group consisting of hydrogen, nitro, hydroxyl, —COOH, —NH$_2$, halogen, cyano, and C$_1$-C$_{14}$ alkyl optionally substituted with 1-3 substituents selected from the group consisting of C$_1$-C$_{14}$ alkyl, C$_1$-C$_{14}$haloalkyl, C$_1$-C$_{14}$ alkoxy, nitro, hydroxyl, —COOH, —NH$_2$, C$_1$-C$_{14}$ alkylamino, C$_1$-C$_{14}$ dialkylamino, halogen, and cyano;

R$^7$ is hydrogen, optionally substituted C$_{1-6}$ alkyl, or a nitrogen protecting group;

Z is selected from the group consisting of hydrogen, optionally substituted C$_1$-C$_{14}$ alkyl, optionally substituted C$_3$-C$_{10}$ cycloalkyl, optionally substituted aryl, optionally substituted aralkyl, optionally substituted alkyl-aryl, and —(CH$_2$)$_p$—K; K is a 5- or 6-membered monocyclic heterocyclic or heteroaryl group containing 1-4 heteroatoms selected from the group consisting of O, N, and S, or an 8- to 10-membered bicyclic heteroaryl group containing 1-4 heteroatoms selected from the group consisting of 0, N, and S;

p is an integer selected from the group consisting of 0, 1, 2, 3, and 4; and q is an integer selected from the group consisting of 0, 1, 2, 3, and 4.

The moieties

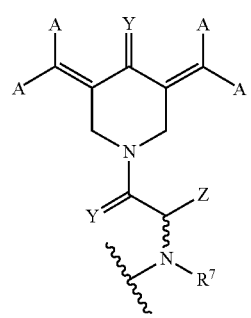

(IA)

and

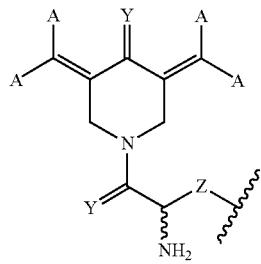

(IB)

are derived from RA190, a binder of the ubiquitin receptor RPN13. The structure of RA190 is

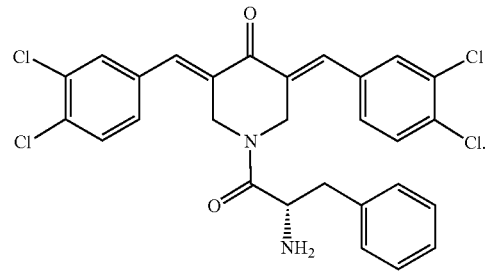 [SMILES: N[C@@H](Cc1ccccc1)C(=O)N1C/C(=C\c2ccc(Cl)c(Cl)c2)C(=O)/C(=C/c2ccc(Cl)c(Cl)c2)C1]

Compounds of Formula (IA) include substituents A, Y, Z, and R$^7$. Compounds of Formula (IB) include substituents A, Y, and Z.

For each set of two moieties A bound to the same carbon atom, one A is hydrogen, and the other A is one of:

(i) phenyl, optionally substituted with 1-5 substituents selected from the group consisting of R$^1$, OR$^1$, NR$^1$R$^2$, S(O)$_q$R$^1$, SO$_2$R$^1$R$^2$, NR$^1$SO$_2$R$^2$, C(O)R$^1$, C(O)OR$^1$, C(O)NR$^1$R$^2$, NR$^1$C(O)R$^2$, NR$^1$C(O)OR$^2$, CF$_3$, and OCF$_3$;

(ii) naphthyl, optionally substituted with 1-5 substituents selected from the group consisting of R$^1$, OR$^1$, NR$^1$R$^2$, S(O)$_q$R$^1$, SO$_2$R$^1$R$^2$, NR$^1$SO$_2$R$^2$, C(O)R$^1$, C(O)OR$^1$, C(O)NR$^1$R$^2$, NR$^1$C(O)R$^2$, NR$^1$C(O)OR$^2$, CF$_3$, and OCF$_3$;

(iii) a 5 or 6 membered monocyclic heteroaryl group, having 1-3 heteroatoms selected from the group consisting of O, N, and S, optionally substituted with 1-3 substituents selected from the group consisting of R$^1$, OR$^1$, NR$^1$R$^2$, S(O)$_q$R$^1$, SO$_2$R$^1$R$^2$, NR$^1$SO$_2$R$^2$, C(O)R$^1$, C(O)OR$^1$, C(O)NR$^1$R$^2$, NR$^1$C(O)R$^2$, NR$^1$C(O)OR$^2$, CF$_3$, and OCF$_3$; and (iv) an 8 to 10 membered bicyclic heteroallyl group containing 1-3 heteroatoms selected from the group consisting of O, N, and S; and the second ring is fused to the first ring using 3 to 4 carbon atoms, and the bicyclic hetero aryl group is optionally substituted with 1-3 substituents selected from the group consisting of R$^1$, OR$^1$, NR$^1$R$^2$, S(O)$_q$R$^1$, SO$_2$R$^1$R$^2$, NR$^1$SO$_2$R$^2$, C(O)R$^1$, C(O)OR$^1$, C(O)NR$^1$R$^2$, NR$^1$C(O)R$^2$, NR$^1$C(O)OR$^2$, CF$_3$, and OCF$_3$.

In each set of two moieties A bound to the same carbon atom, one A is hydrogen, and the other A is one of:

(i) phenyl, optionally substituted with 1-5 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$;

(ii) naphthyl, optionally substituted with 1-5 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$;

(iii) a 5- or 6-membered monocyclic heteroaryl group, having 1-3 heteroatoms selected from the group consisting of O, N, and S, optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$; and (iv) an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$.

In each pair of A's, in some embodiments, one A is phenyl, optionally substituted with 1-5 substituents including —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CF$_3$, and —OCF$_3$. In some embodiments, one A is phenyl. In some embodiments, one A is phenyl substituted with halogen.

In each set of two moieties A bound to the same carbon atom, in some embodiments, one A is phenyl, optionally substituted with 1-5 substituents including —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, or —OCF$_3$. In some embodiments, one A is phenyl. In some embodiments, one A is phenyl substituted with halogen.

In each pair of A's, in some embodiments, one A is naphthyl, optionally substituted with 1-5 substituents including —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CF$_3$, and —OCF$_3$.

In each set of two moieties A bound to the same carbon atom, in some embodiments, one A is naphthyl, optionally substituted with 1-5 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)OR$^1$, —C(O)NR$^1$R$^2$, —NR$^1$C(O)R$^2$, —NR$^1$C(O)OR$^2$, —CHF$_2$, —CH$_2$F, —CF$_3$, and —OCF$_3$. In each set of two moieties A bound to the same carbon atom, in some embodiments, one A is hydrogen and the other A is naphthyl optionally substituted with R$^1$.

In each set of two moieties A bound to the same carbon atom, in some embodiments, one A is a 5- or 6-membered monocyclic heteroaryl group, having 1-3 heteroatoms selected from the group consisting of O, N, and S, optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)ORI, —C(O)NR$^1$R$^2$, —NR$^1$C(O)R$^2$, —NR$^1$C(O)OR$^2$, —CHF$_2$, —CH$_2$F, —CF$_3$, and —OCF$_3$. In some embodiments, one A is a 5- or 6-membered monocyclic heteroaryl group, having 1-3 heteroatoms selected from the group consisting of O, N, and S. In each set of two moieties A bound to the same carbon atom, in some embodiments, one A is hydrogen and the other A is a 5- or 6-membered monocyclic heteroaryl group, having 1-3 heteroatoms selected from the group consisting of O, N, and S, optionally substituted with R$^1$. In some embodiments, one A is a 5- or 6-membered monocyclic heteroaryl group, having 1-3 heteroatoms selected from the group consisting of O, N, and S, substituted with halogen.

In each set of two moieties A bound to the same carbon atom, in some embodiments, one A is an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with 1-3 substituents selected from the group consisting of —R$^1$, —OR$^1$, —NR$^1$R$^2$, —S(O)$_q$R$^1$, —SO$_2$R$^1$R$^2$, —NR$^1$SO$_2$R$^2$, —C(O)R$^1$, —C(O)ORI, —C(O)NR$^1$R$^2$, —NR$^1$C(O)R$^2$, —NR$^1$C(O)OR$^2$, —CHF$_2$, —CH$_2$F, —CF$_3$, and —OCF$_3$. In some embodiments, one A is an 8- to 10-membered bicyclic heteroaryl group containing 1-3 heteroatoms selected from the group consisting of O, N, and S, and having a first ring fused to a second ring through 3 to 4 carbon atoms. In each set of two moieties A bound to the same carbon atom, in some embodiments, one A is hydrogen and the other A is an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with R$^1$. In some embodiments, one A is an 8- to 10-membered bicyclic heteroaryl group containing 1-3 heteroatoms selected from the group consisting of O, N, and S, and having a first ring fused to a second ring through 3 to 4 carbon atoms, substituted with halogen.

In some embodiments, Y is selected from the group consisting of =O, =S, =NR$^1$ and =CR$^1$R$^2$. In some embodiments, at least one instance of Y is =O. In certain embodiments, both Y are =O. In some embodiments, one instance of Y is =O and the other instance of Y is =CH$_2$. In some embodiments, both instances of Y are =CH$_2$.

In some embodiments, at least one instance of R$^1$ or R$^2$ is hydrogen, nitro, hydroxyl, —COOH, —NH$_2$, halogen, cyano, and C$_1$-C$_{14}$ alkyl optionally substituted with 1-3 substituents selected from the group consisting of C$_1$-C$_{14}$ alkyl, C$_1$-C$_{14}$ haloalkyl, C$_1$-C$_{14}$ alkoxy, nitro, hydroxyl, —COOH, —NH$_2$, C$_1$-C$_{14}$ alkylamino, C$_1$-C$_{14}$ dialkylamino, halogen, or cyano. In some embodiments, at least one instance of R$^1$ is hydrogen. In some embodiments, at least one instance of R$^1$ is nitro. In some embodiments, at least one instance of R$^1$ is hydroxyl. In some embodiments, at least one instance of R$^1$ is —COOH. In some embodiments, at least one instance of R$^1$ is —NH$_2$. In some embodiments, at least one instance of R$^1$ is halogen. In some embodiments, at least one instance of R$^1$ is cyano. In some embodiments, at least one instance of R$^1$ is C$_1$-C$_{14}$ alkyl optionally substituted with 1-3 substituents selected from the group consisting of C$_1$-C$_{14}$ alkyl, C$_1$-C$_{14}$ haloalkyl, C$_1$-C$_{14}$ alkoxy, nitro, hydroxyl, —COOH, —NH$_2$, C$_1$-C$_{14}$ alkylamino, C$_1$-C$_{14}$ dialkylamino, halogen, or cyano.

In some embodiments, at least one instance of R$^2$ is hydrogen. In some embodiments, at least one instance of R$^2$ is nitro. In some embodiments, at least one instance of R$^2$ is hydroxyl. In some embodiments, at least one instance of R$^2$ is —COOH. In some embodiments, at least one instance of R$^2$ is —NH$_2$. In some embodiments, at least one instance of R$^2$ is halogen. In some embodiments, at least one instance of R$^2$ is cyano. In some embodiments, at least one instance of R$^2$ is C$_1$-C$_{14}$ alkyl optionally substituted with 1-3 substituents selected from the group consisting of C$_1$-C$_{14}$ alkyl, $C_1$-$C_{14}$ haloalkyl, $C_1$-$C_{14}$ alkoxy, nitro, hydroxyl, —COOH, —$NH_2$, $C_1$-$C_{14}$ alkylamino, $C_1$-$C_{14}$ dialkylamino, halogen, or cyano.

In some embodiments, Z is selected from the group consisting of hydrogen; $C_1$ to $C_{14}$ linear, branched, or cyclic alkyls; phenyl; benzyl, 1-5 substituted benzyl, $C_1$ to $C_3$ alkyl-phenyl, wherein the alkyl moiety is optionally substituted with halogen up to perhalo; up to perhalo substituted $C_1$ to $C_{14}$ linear or branched alkyls; and —$(CH_2)_q$—K. In some embodiments, K is a 5 or 6 membered monocyclic heterocyclic ring, containing 1 to 4 atoms selected from oxygen, nitrogen and sulfur, which is saturated, partially saturated, or aromatic, or an 8 to 10 membered bicyclic heteroaryl having 1-4 heteroatoms selected from the group consisting of O, N, and S, wherein said alkyl moiety is optionally substituted with halogen up to perhalo, and wherein the variable q is an integer ranging from 0 to 4. In certain embodiments, q is 0. In certain embodiments, q is 1. In certain embodiments, q is 2. In certain embodiments, q is 3. In certain embodiments, q is 4.

In some embodiments, Z is hydrogen, optionally substituted $C_1$-$C_{14}$ alkyl, optionally substituted $C_3$-$C_{10}$ cycloalkyl, optionally substituted aryl, optionally substituted aralkyl, optionally substituted alkyl-aryl, or —$(CH_2)_p$—K; K is a 5- or 6-membered monocyclic heterocyclic or heteroaryl group containing 1-4 heteroatoms selected from the group consisting of O, N, and S, or an 8- to 10-membered bicyclic heteroaryl group containing 1-4 heteroatoms selected from the group consisting of O, N, and S; and p is an integer selected from the group consisting of 0, 1, 2, 3, and 4. In some embodiments, Z is hydrogen. In some embodiments, Z is optionally substituted $C_1$-$C_{14}$ alkyl (e.g., optionally substituted methyl, optionally substituted ethyl, optionally substituted propyl). In some embodiments, Z is ($C_{1-6}$alkyl)phenyl or ($C_{1-6}$haloalkyl)phenyl. In some embodiments, Z is ($C_{1-3}$alkyl)phenyl or ($C_{1-3}$haloalkyl)phenyl. In some embodiments, Z is ($C_{1-3}$alkyl)phenyl. In some embodiments, Z is ($C_{1-3}$haloalkyl)phenyl. In some embodiments, Z is optionally substituted $C_1$-$C_6$ alkyl. In some embodiments, Z is optionally substituted $C_3$-$C_{10}$ cycloalkyl. In some embodiments, Z is optionally substituted aryl (e.g., optionally substituted phenyl). In some embodiments, Z is phenyl. In some embodiments, Z is benzyl. In some embodiments, Z is unsubstituted benzyl.

In some embodiments, Z is optionally substituted aralkyl. In some embodiments, Z is optionally substituted alkyl-aryl. In some embodiments, Z is —$(CH_2)_p$—K. In some embodiments, K is a 5- or 6-membered monocyclic heterocyclic or heteroaryl group containing 1-4 heteroatoms selected from the group consisting of O, N, and S, or an 8- to 10-membered bicyclic heteroaryl group containing 1-4 heteroatoms selected from the group consisting of O, N, and S. In some embodiments, K is a 5- or 6-membered monocyclic heterocyclic or heteroaryl group containing 1-3 heteroatoms selected from the group consisting of O, N, and S, or an 8- to 10-membered bicyclic heteroaryl group containing 1-3 heteroatoms selected from the group consisting of O, N, and S. In certain embodiments, p and q are the same. In certain embodiments, p is 0. In certain embodiments, p is 1. In certain embodiments, p is 2. In certain embodiments, p is 3. In certain embodiments, p is 4. In certain embodiments, q is 0. In certain embodiments, q is 1. In certain embodiments, q is 2. In certain embodiments, q is 3. In certain embodiments, q is 4.

In certain embodiments, $R^7$ is hydrogen. In certain embodiments, $R^7$ is optionally substituted $C_{1-6}$ alkyl (e.g., optionally substituted methyl, optionally substituted ethyl).

In certain embodiments, $R^7$ is optionally substituted methyl. In certain embodiments, $R^7$ is substituted methyl. In certain embodiments, $R^7$ is unsubstituted methyl. In certain embodiments, $R^7$ is nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In some embodiments, Z is phenyl. In some embodiments, Z is benzyl. In some embodiments, Z is unsubstituted benzyl. In some embodiments, in each pair of A's, one A is hydrogen and the other A is phenyl optionally substituted with $R^1$. In some embodiments, in each pair of A's, one A is hydrogen and the other A is phenyl substituted with halogen (e.g., fluoro, chloro).

In some embodiments, Z is phenyl. In some embodiments, Z is benzyl. In some embodiments, Z is unsubstituted benzyl. In some embodiments, for each set of two moieties A bound to the same carbon atom, one A is hydrogen, and the other A is phenyl optionally substituted with $R^1$. In some embodiments, for each set of two moieties A bound to the same carbon atom, one A is hydrogen, and the other A is phenyl substituted with halogen (e.g., fluoro, chloro). In some embodiments, for each set of two moieties A bound to the same carbon atom, one A is hydrogen, and the other A is phenyl substituted with at least one instance of halogen (e.g., fluoro, chloro). In some embodiments, for each set of two moieties A bound to the same carbon atom, one A is hydrogen, and the other A is phenyl substituted with at least one instance of —Cl. In some embodiments, for each set of two moieties A bound to the same carbon atom, one A is hydrogen, and the other A is phenyl substituted with two instances of halogen. In some embodiments, for each set of two moieties A bound to the same carbon atom, one A is hydrogen, and the other A is phenyl substituted with two instances of —Cl.

In certain embodiments, D is of formula:

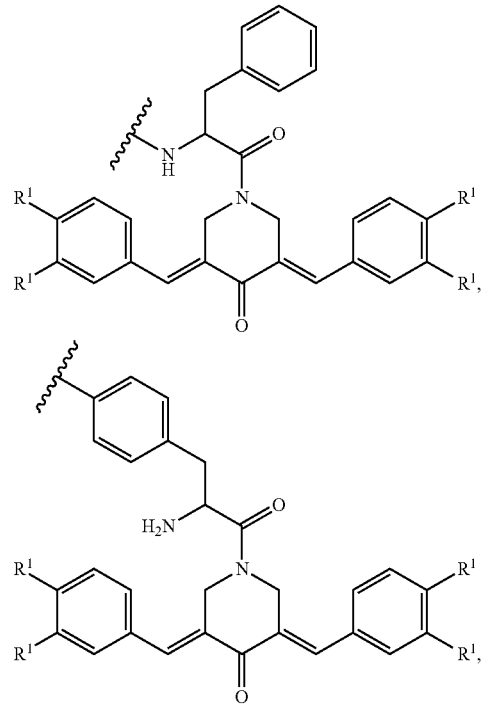

or a pharmaceutically acceptable salt thereof.

In certain embodiments, D is of formula:
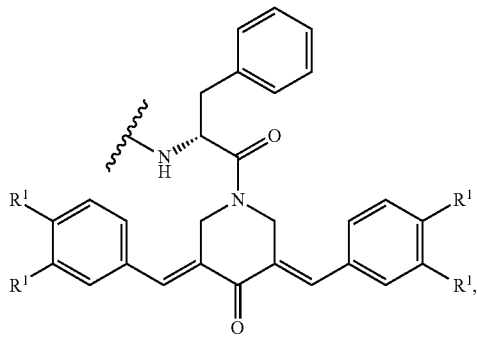
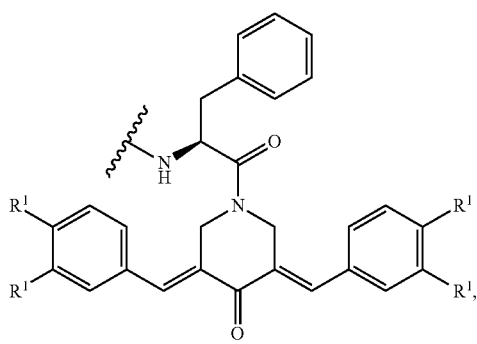
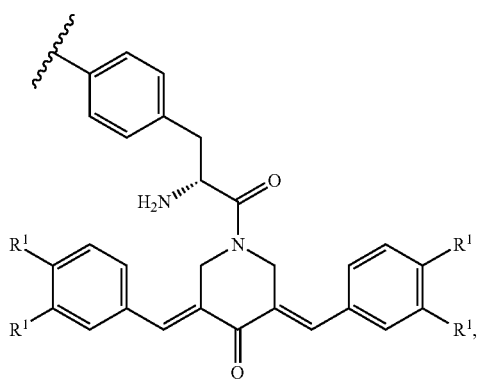
or a pharmaceutically acceptable salt thereof.
In certain embodiments, D is of formula:
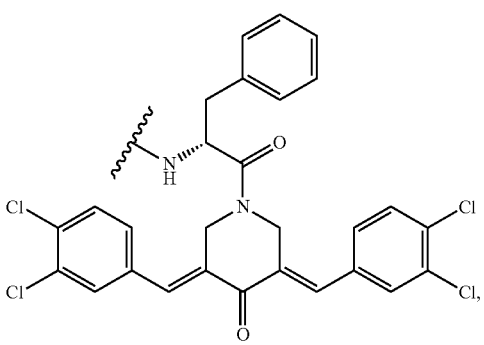 [SMILES: *N[C@H](Cc1ccccc1)C(=O)N1C/C(=C\c2ccc(Cl)c(Cl)c2)C(=O)/C(=C/c2ccc(Cl)c(Cl)c2)C1]
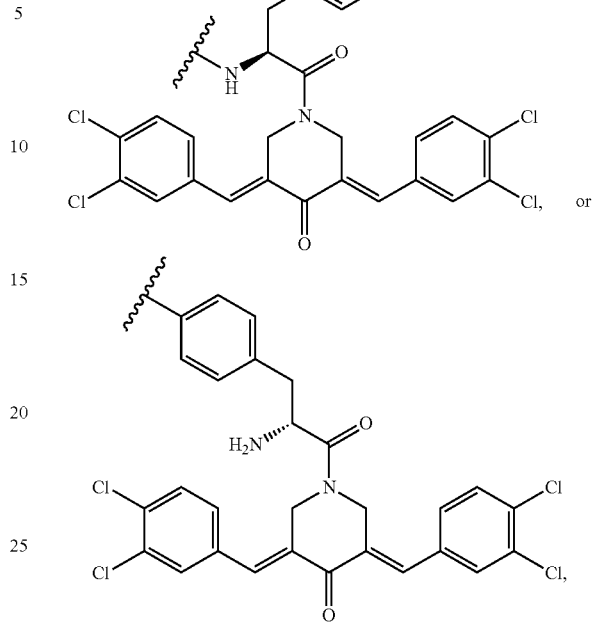
or a pharmaceutically acceptable salt thereof.
In certain embodiments, D is of formula:
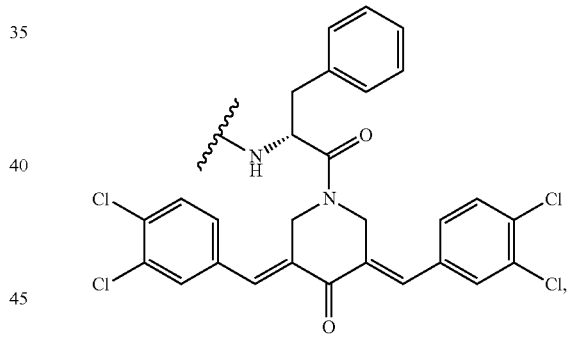
or a pharmaceutically acceptable salt thereof.
In certain embodiments, D is of formula:
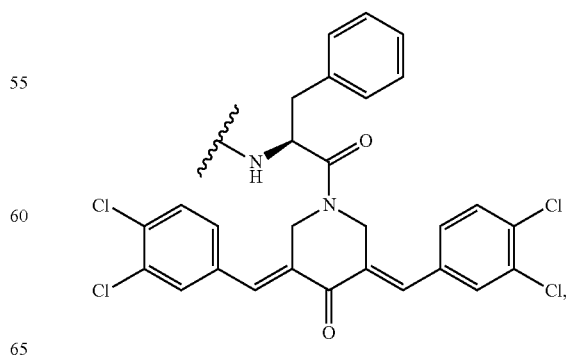
or a pharmaceutically acceptable salt thereof.

In certain embodiments, D is of formula:

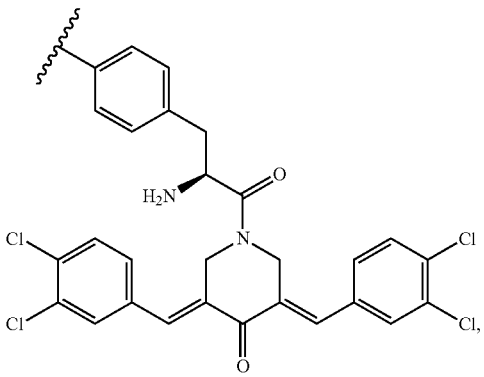 [SMILES: *c1ccc(C[C@H](N)C(=O)N2C/C(=C\c3ccc(Cl)c(Cl)c3)C(=O)/C(=C/c3ccc(Cl)c(Cl)c3)C2)cc1]

or a pharmaceutically acceptable salt thereof.

In certain embodiments, D is of formula:

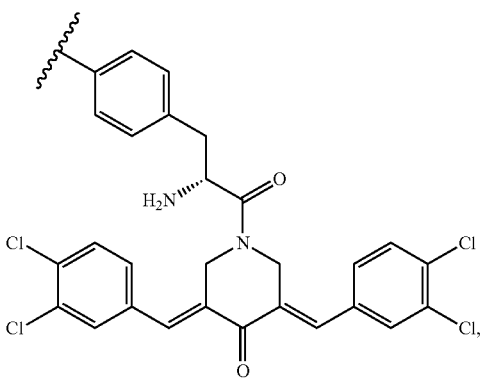 [SMILES: *c1ccc(C[C@@H](N)C(=O)N2C/C(=C\c3ccc(Cl)c(Cl)c3)C(=O)/C(=C/c3ccc(Cl)c(Cl)c3)C2)cc1]

or a pharmaceutically acceptable salt thereof.

Linker L

In Formula (I), L is a divalent moiety linking the group D (i.e., the RPN13 binding moiety) to the moiety of

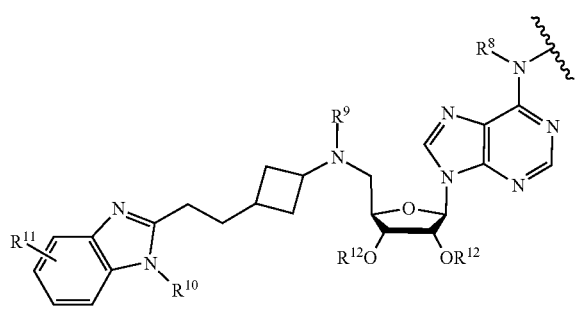

(i.e., the DOT1L binding moiety). In Formula (I), L covalently links the group D to the moiety of

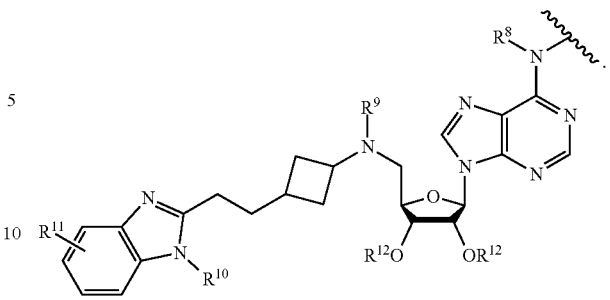

In Formula (I), L is a divalent moiety. In certain embodiments, L is a substituted or unsubstituted $C_{1-50}$ hydrocarbon chain, optionally wherein one or more chain atoms of the hydrocarbon chain are independently replaced with —C(=O)—, —O—, —NR$^b$—, —N=, =N—, —S—, or a cyclic moiety, wherein R$^b$ is independently hydrogen, substituted or unsubstituted $C_{1-6}$ alkyl, or a nitrogen protecting group. In certain embodiments, L is a substituted or unsubstituted $C_{1-30}$ hydrocarbon chain, optionally wherein one or more chain atoms of the hydrocarbon chain are independently replaced with —C(=O)—, —O—, —NR$^b$—, —N=, =N—, —S—, or a cyclic moiety, wherein R$^b$ is independently hydrogen, substituted or unsubstituted $C_{1-6}$ alkyl, or a nitrogen protecting group. In certain embodiments, L is an unsubstituted $C_{1-30}$ hydrocarbon chain, optionally wherein one or more chain atoms of the hydrocarbon chain are independently replaced with —C(=O)—, —O—, —NR$^b$—, —N=, =N—, —S—, or a cyclic moiety, wherein R$^b$ is independently hydrogen, substituted or unsubstituted $C_{1-6}$ alkyl, or a nitrogen protecting group. In certain embodiments, L is a substituted or unsubstituted $C_{1-26}$ hydrocarbon chain, optionally wherein one or more chain atoms of the hydrocarbon chain are independently replaced with —C(=O)—, —O—, —NR$^b$—, —N=, =N—, —S—, or a cyclic moiety, wherein R$^b$ is independently hydrogen, substituted or unsubstituted $C_{1-6}$ alkyl, or a nitrogen protecting group. In certain embodiments, L is an unsubstituted $C_{1-26}$ hydrocarbon chain, optionally wherein one or more chain atoms of the hydrocarbon chain are independently replaced with —C(=O)—, —O—, —NR$^b$—, —N=, =N—, —S—, or a cyclic moiety, wherein R$^b$ is independently hydrogen, substituted or unsubstituted $C_{1-6}$ alkyl, or a nitrogen protecting group. In certain embodiments, L is any "L0" group or "Linker" group recited in U.S. patent application Ser. No. 14/707,930, filed May 8, 2015, issued as U.S. Pat. No. 9,694,084, on Jul. 4, 2017, which is incorporated herein by reference. In certain embodiments, L is any "L" group recited in U.S. patent application Ser. No. 14/792,414, filed Jul. 6, 2015, published as US 2016-0058872, on Mar. 3, 2016, which is incorporated herein by reference.

In certain embodiments, the chain of linker L comprises up to 50 atoms as the shortest path between D and the moiety of

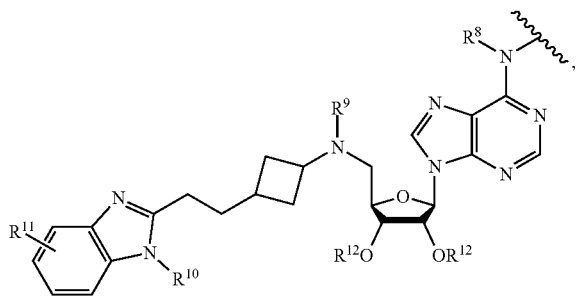

excluding hydrogen atoms. In certain embodiments, the chain of linker L comprises up to 50 atoms, excluding hydrogen atoms. In certain embodiments, L comprises up to 46 atoms, excluding hydrogen atoms. In certain embodiments, L comprises up to 45 atoms, excluding hydrogen atoms. In certain embodiments, L comprises up to 40 atoms, excluding hydrogen atoms. In certain embodiments, L comprises up to 35 atoms, excluding hydrogen atoms. In certain embodiments, L comprises up to 32 atoms, excluding hydrogen atoms. In certain embodiments, L comprises up to 30 atoms, excluding hydrogen atoms. In certain embodiments, L comprises up to 28 atoms, excluding hydrogen atoms. In certain embodiments, L comprises up to 27 atoms, excluding hydrogen atoms. In certain embodiments, L comprises up to 26 atoms, excluding hydrogen atoms. In certain embodiments, L comprises up to 25 atoms, excluding hydrogen atoms. In certain embodiments, L comprises up to 25 atoms, excluding hydrogen atoms. In certain embodiments, L comprises up to 23 atoms, excluding hydrogen atoms. In certain embodiments, L comprises up to 20 atoms, excluding hydrogen atoms. In certain embodiments, L comprises up to 14 atoms, excluding hydrogen atoms. In certain embodiments, L comprises up to 15 atoms, excluding hydrogen atoms. In certain embodiments, L comprises up to 12 atoms, excluding hydrogen atoms. In certain embodiments, L comprises up to 10 atoms, excluding hydrogen atoms. In certain embodiments, L comprises up to 9 atoms excluding hydrogen atoms. In certain embodiments, L comprises up to 6 atoms excluding hydrogen atoms. In certain embodiments, L comprises up to 5 atoms excluding hydrogen atoms. In certain embodiments, L comprises up to 3 atoms excluding hydrogen atoms.

In certain embodiments, any of the atoms in L can be substituted. In certain embodiments, none of the atoms in the linker L are substituted. In certain embodiments, none of the carbon atoms in the linker are substituted.

In certain embodiments, L comprises substituted or unsubstituted carbocyclylene, substituted or unsubstituted heterocyclylene, substituted or unsubstituted arylene, substituted or unsubstituted heteroarylene, or substituted or unsubstituted heteroalkylene. In certain embodiments, each instance of $R^b$ is independently hydrogen, substituted or unsubstituted $C_{1-6}$ alkyl, or a nitrogen protecting group, or optionally two instances of $R^b$ are taken together with their intervening atoms to form a substituted or unsubstituted heterocyclic or substituted or unsubstituted heteroaryl ring. In certain embodiments, at least one instance of $R^b$ is hydrogen. In certain embodiments, at least one instance of $R^b$ is substituted or unsubstituted $C_{1-6}$ alkyl (e.g., substituted or unsubstituted methyl or ethyl). In certain embodiments, at least one instance of $R^b$ is a nitrogen protecting group (e.g., benzyl (Bn), t-butyl carbonate (BOC or Boc), benzyl carbamate (Cbz), 9-fluorenylmethyl carbonate (Fmoc), trifluoroacetyl, triphenylmethyl, acetyl, or p-toluenesulfonamide (Ts)).

In certain embodiments, L is an unsubstituted $C_{1-45}$ hydrocarbon chain, optionally wherein one or more chain atoms of the hydrocarbon chain are independently replaced with —C(=O)—, —O—, —NR$^b$—, or a cyclic moiety, wherein $R^b$ is independently hydrogen, substituted or unsubstituted $C_{1-6}$ alkyl, or a nitrogen protecting group. In certain embodiments, L is an unsubstituted $C_{1-30}$ hydrocarbon chain, wherein one or more chain atoms of the hydrocarbon chain are independently replaced with —O— or —NR$^b$—. In certain embodiments, L is an unsubstituted $C_{1-30}$ hydrocarbon chain, wherein one or more chain atoms of the hydrocarbon chain are independently replaced with C(=O)—. In certain embodiments, L is an unsubstituted $C_{1-26}$ hydrocarbon chain, wherein one or more chain atoms of the hydrocarbon chain are independently replaced with C(=O)—. In certain embodiments, L is an unsubstituted $C_{1-30}$ hydrocarbon chain, wherein at least one chain atom of the hydrocarbon chain is independently replaced with —O—. In certain embodiments, L is an unsubstituted $C_{1-26}$ hydrocarbon chain, wherein one or more chain atoms of the hydrocarbon chain are independently replaced with —C(=O)—, —O—, or —NR$^b$—. In certain embodiments, L is an unsubstituted $C_{1-26}$ hydrocarbon chain, wherein at least one chain atom of the hydrocarbon chain is independently replaced with —C(=O)—. In certain embodiments, L is an unsubstituted $C_{5-26}$ hydrocarbon chain, wherein one or more chain atoms of the hydrocarbon chain are independently replaced with —C(=O)—, —O—, or —NR$^b$—. In certain embodiments, L is an unsubstituted $C_{5-20}$ hydrocarbon chain, wherein one or more chain atoms of the hydrocarbon chain are independently replaced with —C(=O)—, —O—, or —NR$^b$—. In certain embodiments, L is an unsubstituted $C_{5-15}$ hydrocarbon chain, wherein one or more chain atoms of the hydrocarbon chain are independently replaced with —C(=O)—, —O—, or —NR$^b$—. In certain embodiments, L is an unsubstituted $C_{15-20}$ hydrocarbon chain, wherein one or more chain atoms of the hydrocarbon chain are independently replaced with —C(=O)—, —O—, or —NR$^b$—. In certain embodiments, L is an unsubstituted $C_{20-25}$ hydrocarbon chain, wherein one or more chain atoms of the hydrocarbon chain are independently replaced with —C(=O)—, —O—, or —NR$^b$— In certain embodiments, L is a substituted or unsubstituted $C_{1-45}$ hydrocarbon chain. In certain embodiments, L is a substituted or unsubstituted $C_{5-40}$ hydrocarbon chain. In certain embodiments, one or more chain atoms of the hydrocarbon chain of L are independently replaced with —C(=O)—, —O—, —S—, —NR$^b$—, —N=, or =N—, wherein $R^b$ is independently hydrogen, substituted or unsubstituted $C_{1-6}$ alkyl, or a nitrogen protecting group. In certain embodiments, one or more chain atoms of the hydrocarbon chain of L are independently replaced with —C(=O)—, —O—, or —NR$^b$—, wherein $R^b$ is independently hydrogen, substituted or unsubstituted $C_{1-6}$ alkyl, or a nitrogen protecting group.

In certain embodiments, L is an all-carbon, substituted or unsubstituted $C_{1-50}$ hydrocarbon chain. In certain embodiments, L is an all-carbon, substituted or unsubstituted $C_{1-45}$ hydrocarbon chain. In certain embodiments, L is an all-carbon, substituted or unsubstituted $C_{1-30}$ hydrocarbon chain. In certain embodiments, L is an all-carbon, substituted or unsubstituted $C_{1-26}$ hydrocarbon chain.

In certain embodiments, L is an unsubstituted $C_{1-30}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is an unsubstituted C$_{1-26}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, L is an unsubstituted C$_{5-26}$ hydrocarbon chain, optionally wherein one or more chain atoms of the hydrocarbon chain are independently replaced with —C(=O)—, —O—, —NR$^b$—, or a cyclic moiety, wherein R$^b$ is independently hydrogen, substituted or unsubstituted C$_{1-6}$ alkyl, or a nitrogen protecting group. In certain embodiments, at least one chain atom of the hydrocarbon chain of L is independently replaced with —C(=O)—. In certain embodiments, at least one chain atom of the hydrocarbon chain of L is independently replaced with —NR$^b$—, wherein R$^b$ is independently hydrogen, substituted or unsubstituted C$_{1-6}$ alkyl, or a nitrogen protecting group. In certain embodiments, L is an unsubstituted C$_{5-26}$ hydrocarbon chain, wherein none of the chain atoms of the hydrocarbon chain are replaced with —C(=O)—, —O—, —NR$^b$—, or a cyclic moiety, wherein R$^b$ is as discussed above. In certain embodiments, L is an unsubstituted C$_{5-26}$ hydrocarbon alkylene chain.

In certain embodiments, L includes the moiety

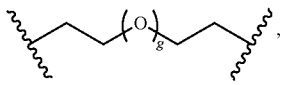

wherein g is 1, 2, 3, 4, 5, or 6. In certain embodiments, g is 1. In certain embodiments, g is 2. In certain embodiments, g is 3. In certain embodiments, g is 4. In certain embodiments, g is 5. In certain embodiments, g is 6. In certain embodiments, L includes the moiety —NHC(=O)—. In certain embodiments, L includes the moiety —NH—.

In certain embodiments, L includes an optionally substituted heterocyclyl group. In certain embodiments, L includes an unsubstituted heterocyclyl group. In certain embodiments, L includes the moiety

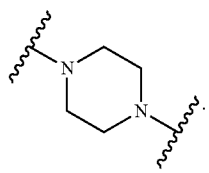 [SMILES: *N1CCN(*)CC1]

In certain embodiments, L is of the formula:

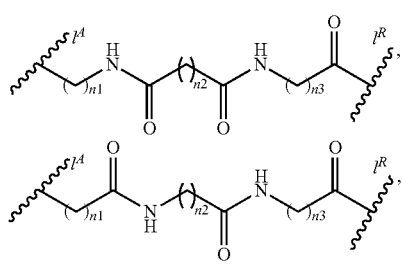

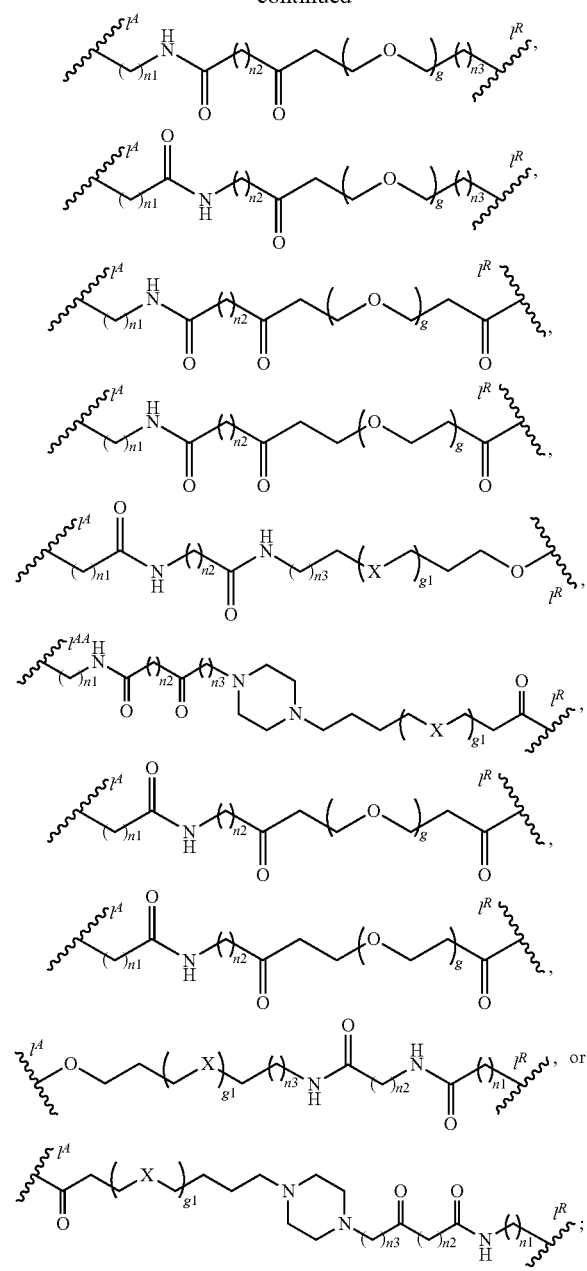

and l$^R$ indicates the point of attachment to D, and l$^A$ indicates the point of attachment to the moiety of formula:

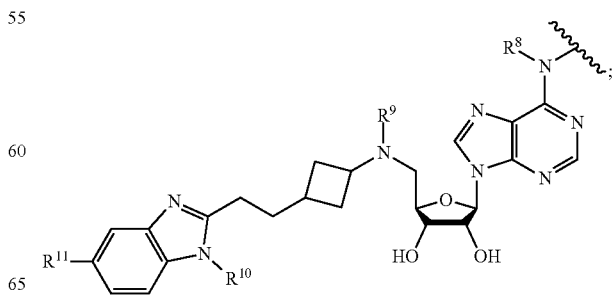

X is —CH$_2$— or —O—; n1 is 1, 2, 3, 4, 5, or 6; n2 is 1, 2, 3, 4, 5, or 6; n3 is 1, 2, 3, 4, 5, 6, 7, 8, 9, 10, 11, or 12; g is 1, 2, 3, 4, 5, or 6; and g1 is 1, 2, 3, 4, 5, 6, 7, 8, 9, or 10. In certain embodiments, X is —CH$_2$—. In certain embodiments, X is —O—. In certain embodiments, n1 is 1. In certain embodiments, n1 is 2. In certain embodiments, n1 is 3. In certain embodiments, n1 is 4. In certain embodiments, n1 is 5. In certain embodiments, n1 is 6. In certain embodiments, n2 is 1. In certain embodiments, n2 is 2. In certain embodiments, n2 is 3. In certain embodiments, n2 is 4. In certain embodiments, n2 is 5. In certain embodiments, n2 is 6. In certain embodiments, n3 is 1. In certain embodiments, n3 is 2. In certain embodiments, n3 is 3. In certain embodiments, n3 is 4. In certain embodiments, n3 is 5. In certain embodiments, n3 is 6. In certain embodiments, n3 is 7. In certain embodiments, n3 is 8. In certain embodiments, n3 is 9. In certain embodiments, n3 is 10. In certain embodiments, n3 is 11. In certain embodiments, n3 is 12. In certain embodiments, g is 1. In certain embodiments, g is 2. In certain embodiments, g is 3. In certain embodiments, g is 4. In certain embodiments, g is 5. In certain embodiments, g is 6. In certain embodiments, g1 is 1. In certain embodiments, g1 is 2. In certain embodiments, g1 is 3. In certain embodiments g1 is 4. In certain embodiments, g1 is 5. In certain embodiments, g1 is 6. In certain embodiments, g1 is 5. In certain embodiments, g1 is 6. In certain embodiments, g1 is 7. In certain embodiments, g1 is 8. In certain embodiments, g1 is 9. In certain embodiments, g1 is 10.

In certain embodiments, L is of the formula:

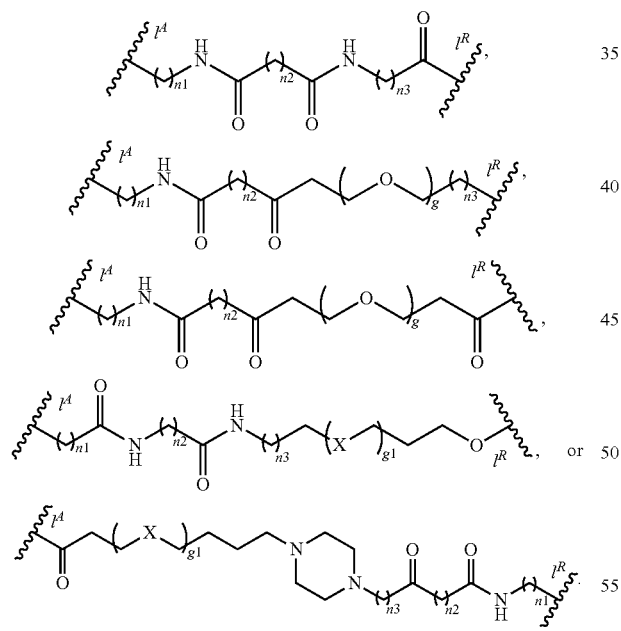

In certain embodiments, L is of the formula:

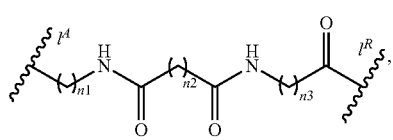

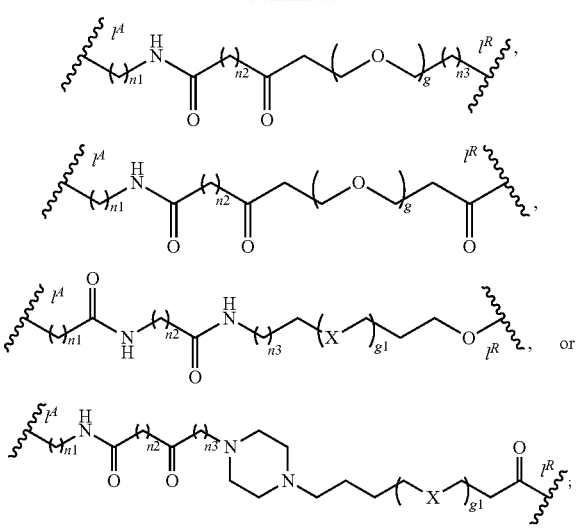

wherein X is —CH$_2$— or —O—; n1 is 1, 2, 3, 4, 5, or 6; n2 is 1, 2, 3, 4, 5, or 6; n3 is 1, 2, 3, 4, 5, 6, 7, 8, 9, 10, 11, or 12; g is 1, 2, 3, 4, 5, or 6; and g1 is 1, 2, 3, 4, 5, 6, 7, 8, 9, or 10. In certain embodiments, n1 is 3. In certain embodiments, n1 is 4. In certain embodiments, n1 is 5. In certain embodiments, n1 is 6. In certain embodiments, n2 is 2. In certain embodiments, n2 is 3. In certain embodiments, n2 is 4. In certain embodiments, n2 is 5. In certain embodiments, n3 is 1. In certain embodiments, n3 is 2. In certain embodiments, g is 1. In certain embodiments, g is 2. In certain embodiments, g is 3. In certain embodiments, g is 5. In certain embodiments, g is 6. In certain embodiments, g1 is 1. In certain embodiments, g1 is 2. In certain embodiments, X is —CH$_2$—. In certain embodiments, X is —O—.

In certain embodiments, L is of the formula:

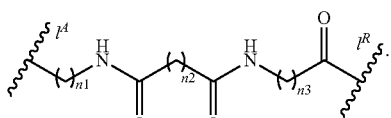

In certain embodiments, L is of the formula:

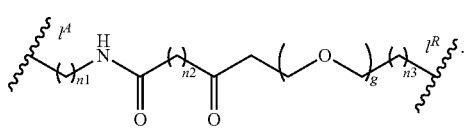

In certain embodiments, L is of the formula:

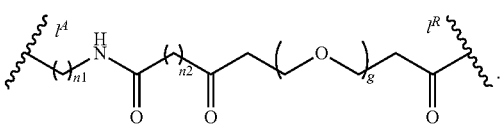

In certain embodiments, L is of the formula:

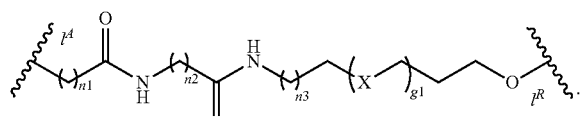

In certain embodiments, L is of the formula:

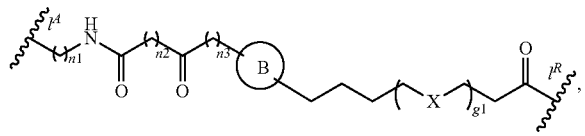

wherein ring B is an optionally substituted 5-10 membered heterocyclyl or optionally substituted 5-14 membered heteroaryl group. In certain embodiments, ring B is optionally substituted 5-10 membered heterocyclyl. In certain embodiments, ring B is optionally substituted 6 membered heterocyclyl. In certain embodiments, ring B is unsubstituted 6 membered heterocyclyl. In certain embodiments, ring B is unsubstituted 6 membered heterocyclyl. In certain embodiments, ring B is unsubstituted piperidinyl, piperazinyl, morpholinyl, dithianyl, or dioxanyl. In certain embodiments, L is of the formula:

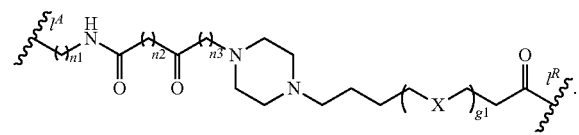

In certain embodiments, L is of the formula:

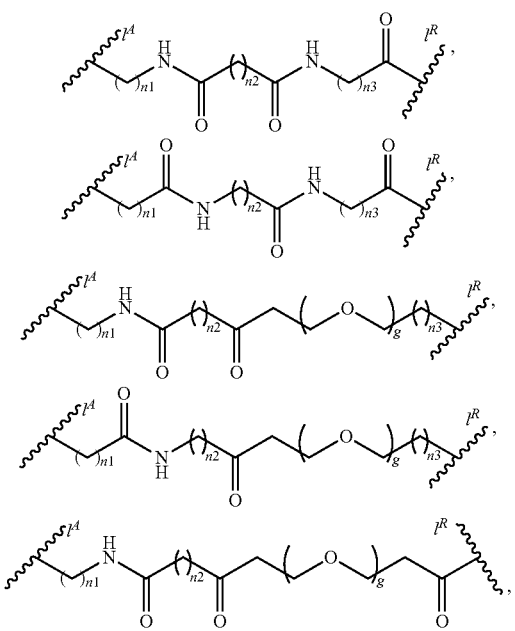

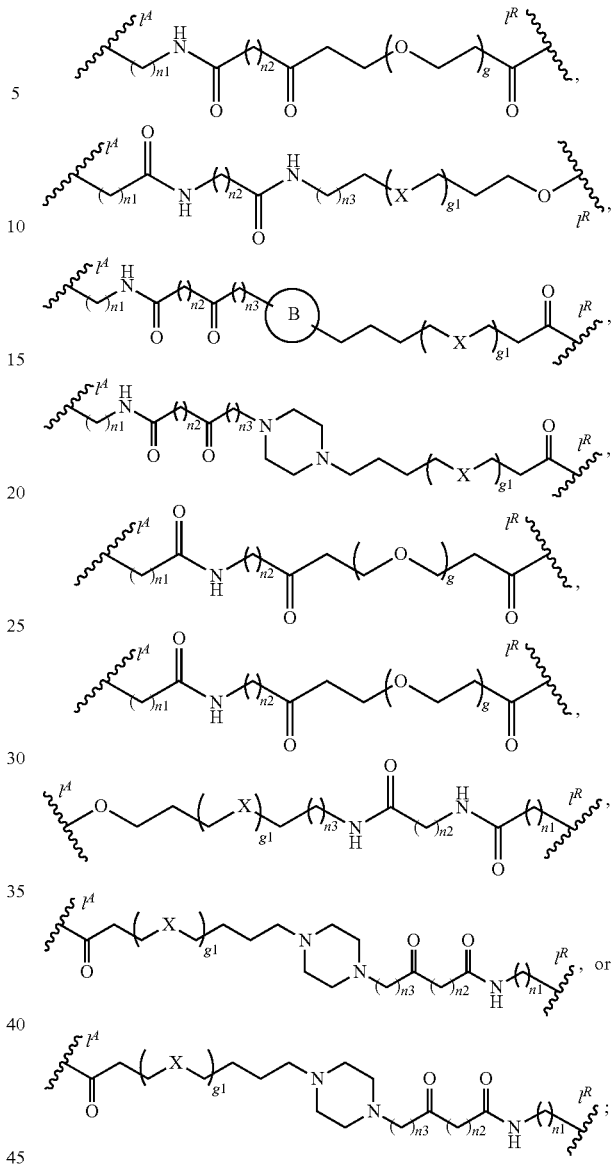

and $l^R$ indicates the point of attachment to D, and $l^A$ indicates the point of attachment to the moiety of formula

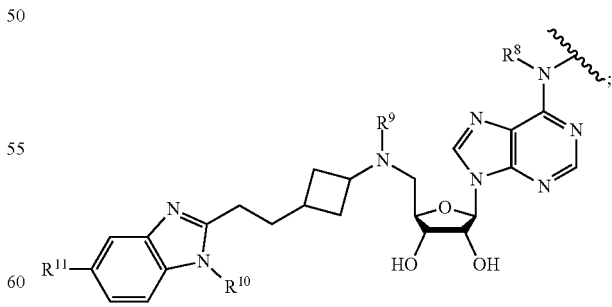

X is —CH$_2$— or —O—; ring B is an optionally substituted 5-10 membered heterocyclyl or optionally substituted 5-14 membered heteroaryl group; n1 is 1, 2, 3, 4, 5, or 6; n2 is 1, 2, 3, 4, 5, or 6; n3 is 1, 2, 3, 4, 5, 6, 7, 8, 9, 10, 11, or 12; g is 1, 2, 3, 4, 5, or 6; and g1 is 1, 2, 3, 4, 5, 6, 7, 8, 9, or 10.

In certain embodiments, L is of the formula:
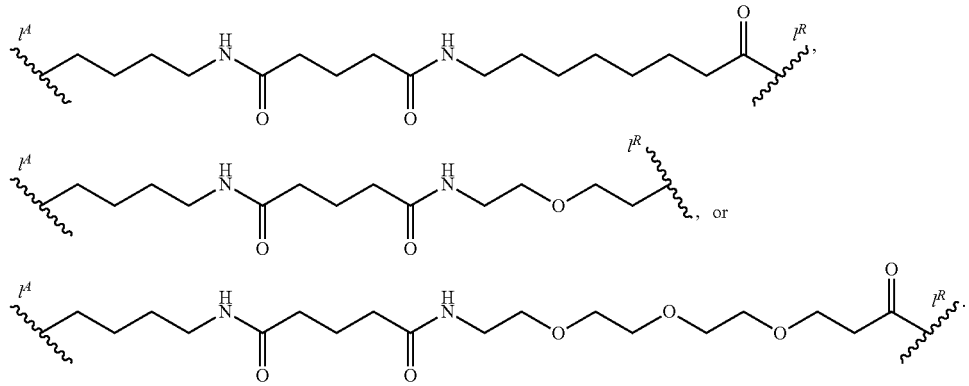
In certain embodiments, L is of the formula:
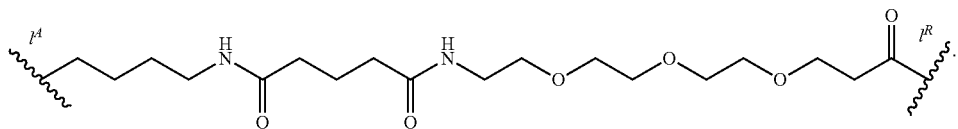
In certain embodiments, L is of the formula:
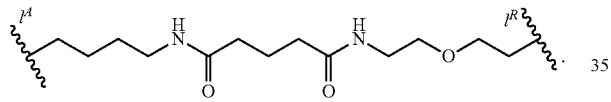
In certain embodiments, L is of the formula:
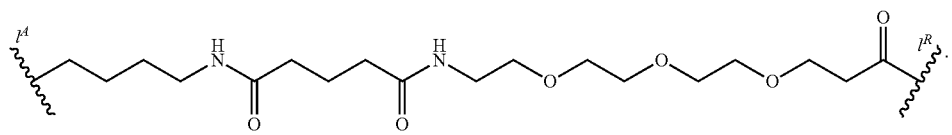 [SMILES: *CCCCNC(=O)CCCC(=O)NCCOCCOCCOCCC(*)=O]
In certain embodiments, L is of the formula:
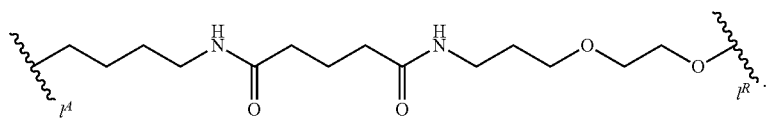 [SMILES: *CCCCNC(=O)CCCC(=O)NCCCOCCO*]
In certain embodiments, L is of the formula:
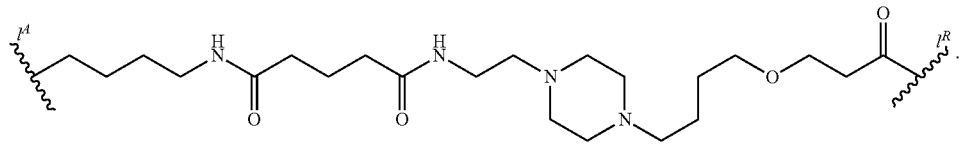 [SMILES: *CCCCNC(=O)CCCC(=O)NCCN1CCN(CCCCOCCC(*)=O)CC1]

In certain embodiments, L is of the formula:
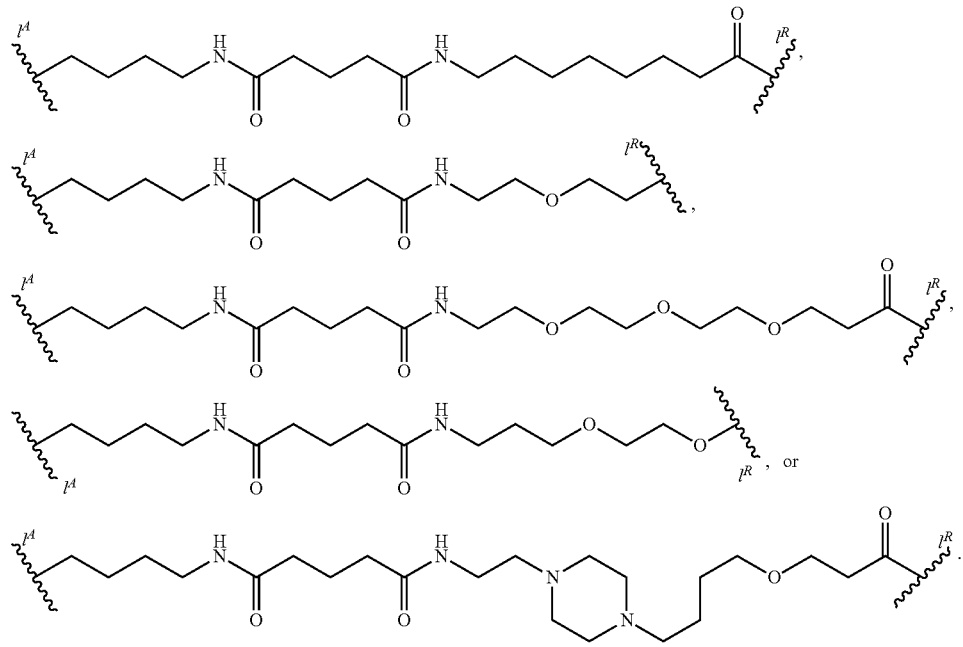
In certain embodiments, L is of the formula:
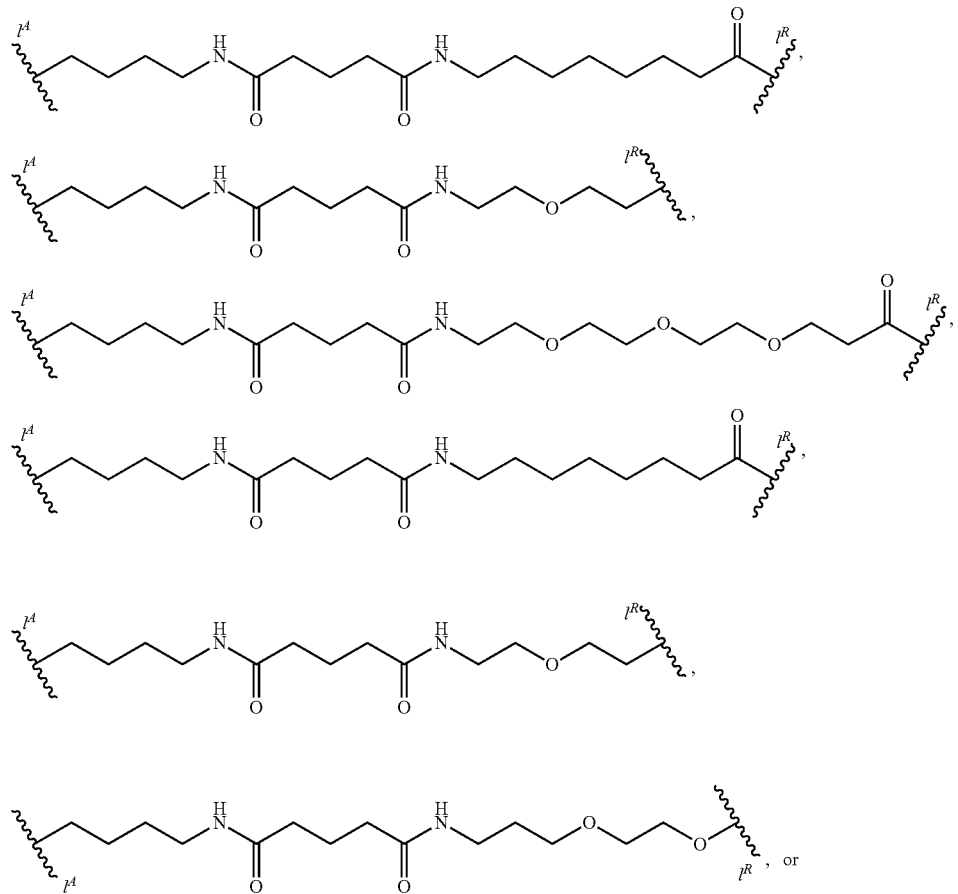

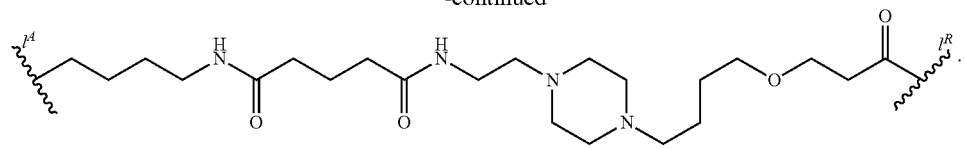
Compounds of Formula (I)
In certain embodiments, a compound of Formula (I) is of the formula:
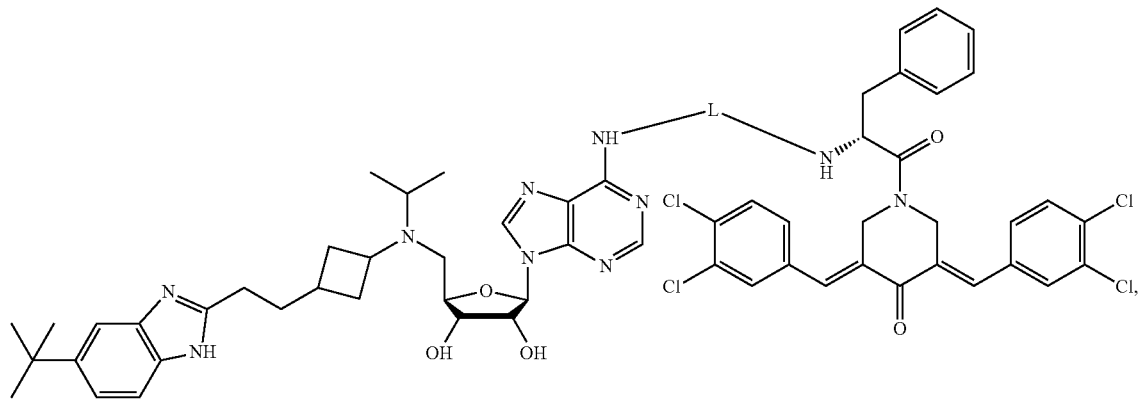
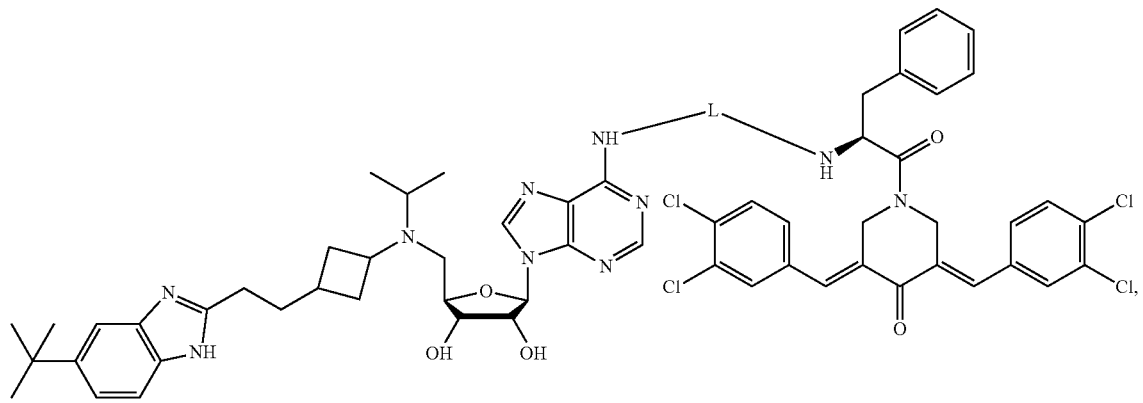
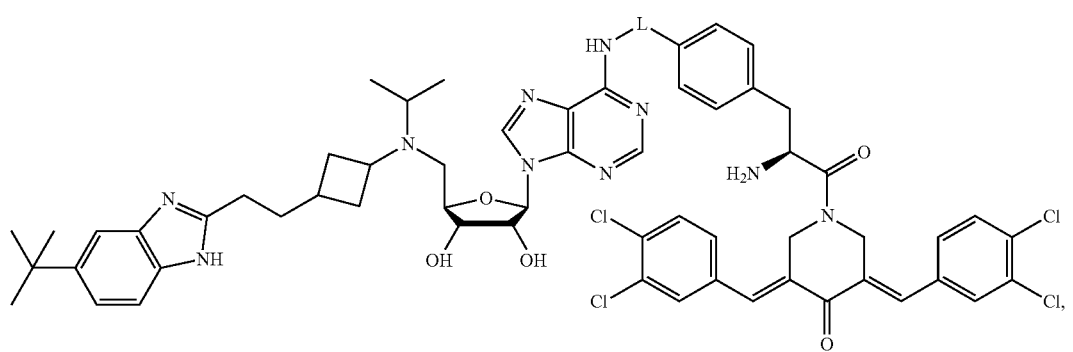

-continued

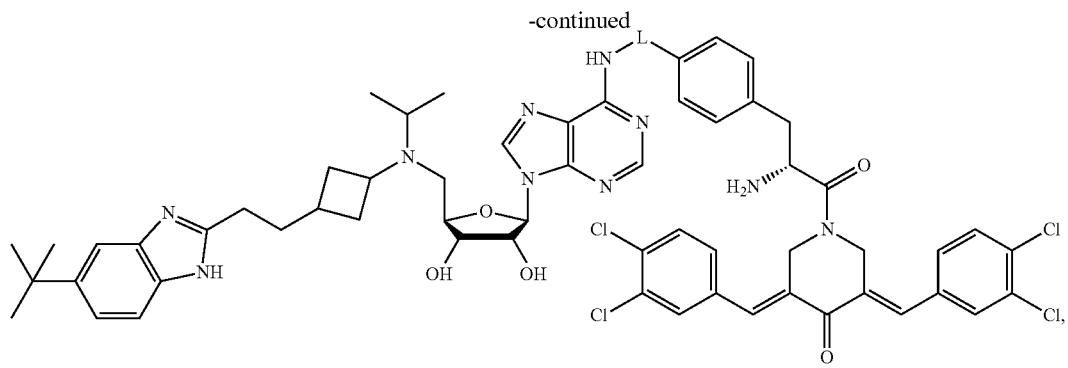

or a pharmaceutically acceptable salt, co-crystal, tautomer, stereoisomer, solvate, hydrate, polymorph, isotopically enriched derivative, or prodrug thereof.

In certain embodiments, a compound of Formula (I) is of the formula:

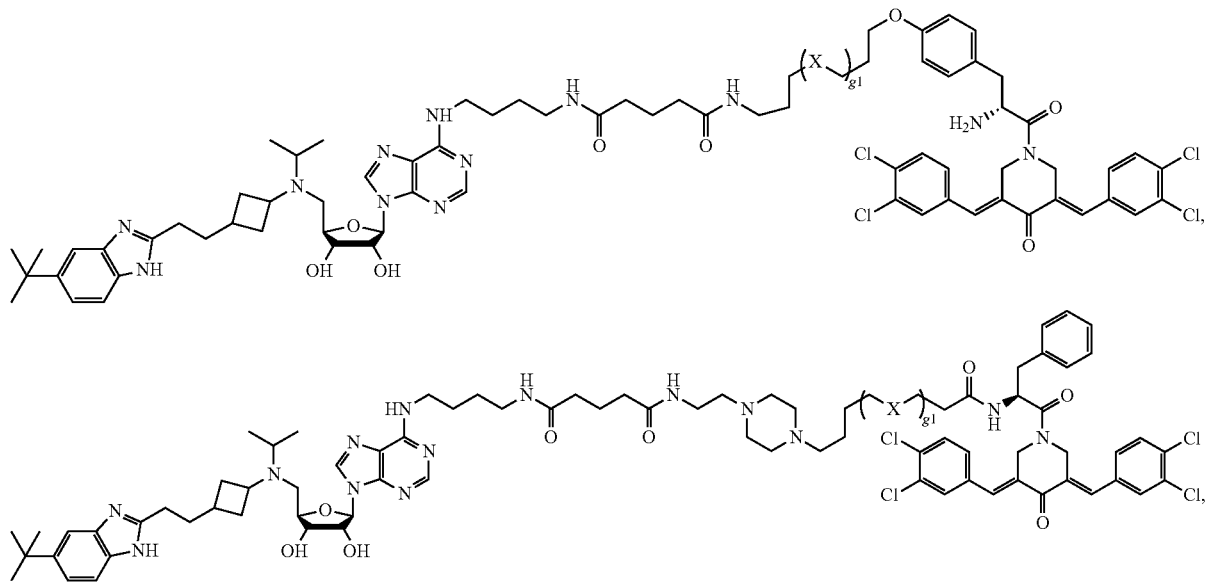

or a pharmaceutically acceptable salt, co-crystal, tautomer, stereoisomer, solvate, hydrate, polymorph, isotopically enriched derivative, or prodrug thereof.

In certain embodiments, a compound of Formula (I) is of the formula:

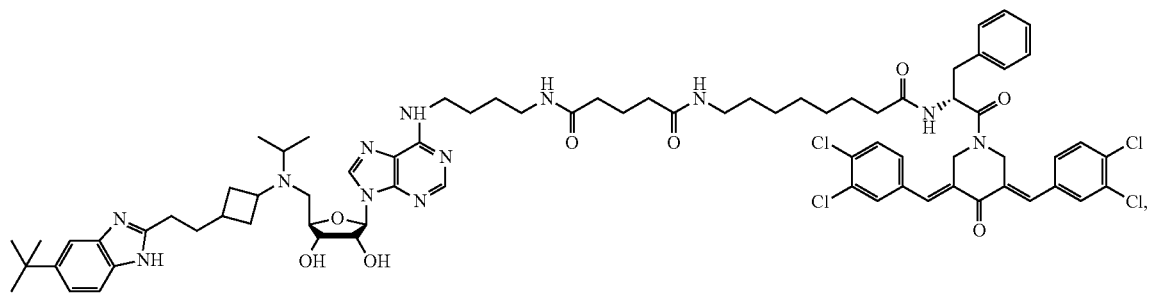

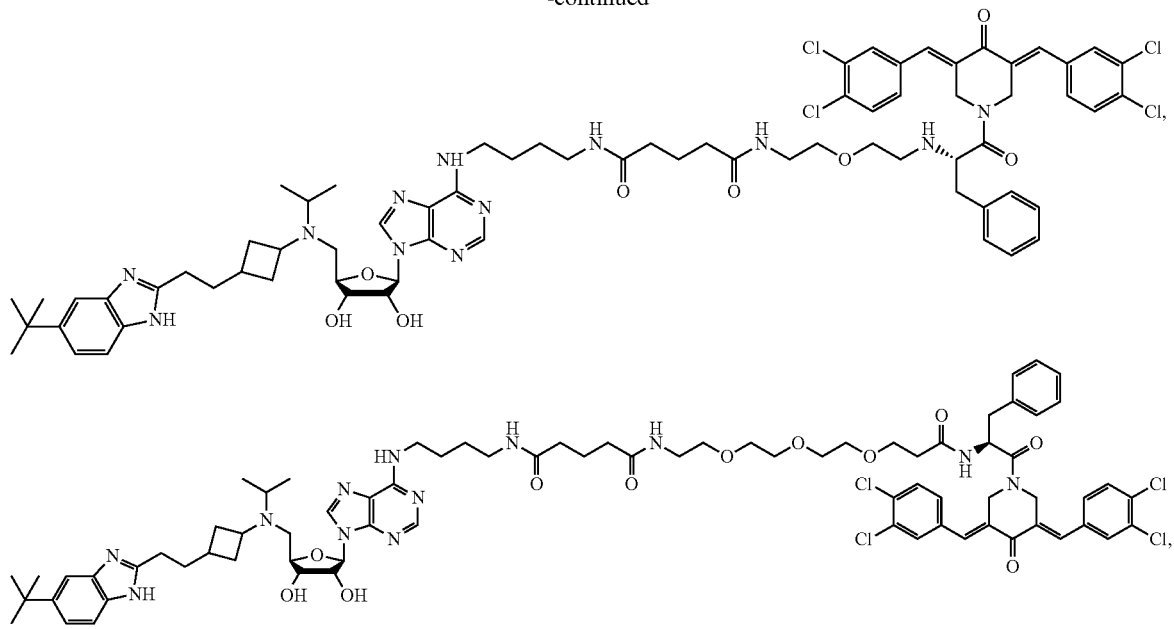

or a pharmaceutically acceptable salt, co-crystal, tautomer, stereoisomer, solvate, hydrate, polymorph, isotopically enriched derivative, or prodrug thereof.

In certain embodiments, the compound of Formula (I) includes a pharmaceutically acceptable salt, solvate, hydrate, tautomer, or stereoisomer thereof. In certain embodiments, the compound of Formula (I) includes a pharmaceutically acceptable salt thereof. In some embodiments, the compound of Formula (I) binds (e.g., non-covalently binds) to DOT1L over another protein. In some embodiments, the compound of Formula (I) selectively binds DOT1L over another protein (e.g., another methyltransferase). In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Without wishing to be bound by any particular theory, the compounds described herein are able to bind (e.g., non-covalently bind) the DOT1L protein being degraded. In certain embodiments, a compound described herein is able to bind (e.g., non-covalently bind) the protein DOT1L. In certain embodiments, a compound described herein is able to bind the protein DOT1L. In some embodiments, the compound of Formula (I) selectively degrades DOT1L over other proteins in the proteome. In some embodiments, the compound of Formula (I) selectively degrades DOT1L over other methyltransferases. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

Without wishing to be bound by any particular theory, the compounds described herein are able to bind (e.g., covalently bind) RPN13. In certain embodiments, a compound described herein is able to covalently bind RPN13. In some embodiments, the compound of Formula (I) selectively binds RPN13 over another protein. In certain embodiments, the selectivity is between about 2-fold and about 5-fold. In certain embodiments, the selectivity is between about 5-fold and about 10-fold. In certain embodiments, the selectivity is between about 10-fold and about 20-fold. In certain embodiments, the selectivity is between about 20-fold and about 50-fold. In certain embodiments, the selectivity is between about 50-fold and about 100-fold. In certain embodiments, the selectivity is between about 100-fold and about 200-fold. In certain embodiments, the selectivity is between about 200-fold and about 500-fold. In certain embodiments, the selectivity is between about 500-fold and about 1000-fold. In certain embodiments, the selectivity is at least about 1000-fold.

In certain embodiments, the compound of Formula (I) induces the degradation of up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% of the target protein DOT1L at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

In certain embodiments, the compound of Formula (I) increases the rate of degradation of the target protein DOT1L up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95%, up to 99%, or up to 100% at a concentration of 100,000 nM or less, 50,000 nM or less, 20,000 nM or less, 10,000 nM or less, 5,000 nM or less, 3,500 nM or less, 2,500 nM or less, 1,000 nM or less, 900 nM or less, 800 nM or less, 700 nM or less, 600 nM or less, 500 nM or less, 400 nM or less, 300 nM or less, 200 nM or less, 100 nM or less, 90 nM or less, 80 nM or less, 70 nM or less, 60 nM or less, 50 nM or less, 40 nM or less, 30 nM or less, 20 nM or less, 10 nM or less, 5 nM or less, 4 nM or less, 3 nM or less, 2 nM or less, or 1 nM or less.

Pharmaceutical Compositions, Kits, and Administration

The present disclosure provides pharmaceutical compositions comprising a compound of Formula (I), or a pharmaceutically acceptable salt, co-crystal, tautomer, stereoisomer, solvate, hydrate, polymorph, isotopically enriched derivative, or prodrug thereof, and optionally a pharmaceutically acceptable excipient. In certain embodiments, the pharmaceutical composition described herein comprises a compound of Formula (I), or a pharmaceutically acceptable salt thereof, and a pharmaceutically acceptable excipient.

In certain embodiments, the compound of Formula (I) is provided in an effective amount in the pharmaceutical composition. In certain embodiments, the effective amount is a therapeutically effective amount. In certain embodiments, the effective amount is a prophylactically effective amount. In certain embodiments, the effective amount is an amount effective for treating a disease (e.g., a proliferative disease) in a subject in need thereof. In certain embodiments, the effective amount is an amount effective for preventing a disease (e.g., a proliferative disease) in a subject in need thereof. In certain embodiments, the effective amount is an amount effective for treating cancer in a subject in need thereof. In certain embodiments, the effective amount is an amount effective for preventing cancer in a subject in need thereof. In certain embodiments, the effective amount is an amount effective for reducing the risk of developing a disease (e.g., proliferative disease or cancer) in a subject in need thereof.

In certain embodiments, the subject is an animal. The animal may be of either sex and may be at any stage of development. In certain embodiments, the subject described herein is a human. In certain embodiments, the subject is a non-human animal. In certain embodiments, the subject is a mammal. In certain embodiments, the subject is a non-human mammal. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal, such as a rodent (e.g., mouse, rat), dog, pig, or non-human primate. In certain embodiments, the animal is a genetically engineered animal. In certain embodiments, the animal is a transgenic animal (e.g., transgenic mice and transgenic pigs). In certain embodiments, the subject is a fish or reptile.

In certain embodiments, the effective amount is an amount effective for inducing the degradation of at least about 10%, at least about 15%, at least about 20%, at least about 25%, at least about 30%, at least about 35%, at least about 40%, at least about 42%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% of the target protein DOT1L in a cell. In certain embodiments, the effective amount is an amount effective for inducing the degradation of the target protein DOT1L in a cell by a range between a percentage described in this paragraph and another percentage described in this paragraph, inclusive.

The present disclosure provides pharmaceutical compositions comprising a compound that interacts with the ubiquitin receptor RPN13 and the target protein DOT1L for use in treating a disease (e.g., a proliferative disease) in a subject in need thereof. In certain embodiments, the composition is for use in treating cancer. In certain embodiments, the composition is for use in treating multiple myeloma, lymphoma, leukemia (e.g., acute myelocytic leukemia (e.g., acute myelocytic leukemia with a mutation in the nucleophosmin (NPM1) gene; acute myelocytic leukemia with a mutation in the DNMT3A gene), mixed-lineage leukemia (MLL) rearranged acute myelocytic leukemia), or a cancer resistant to proteasome inhibitors. In certain embodiments, the composition is for use in treating multiple myeloma. In certain embodiments, the composition is for use in treating lymphoma. In certain embodiments, the composition is for use in treating leukemia. In certain embodiments, the composition is for use in treating acute myelocytic leukemia. In certain embodiments, the composition is for use in treating acute myelocytic leukemia with a mutation in the nucleophosmin (NPM1) gene. In certain embodiments, the composition is for use in treating acute myelocytic leukemia with a mutation in the DNMT3A gene. In certain embodiments, the composition is for use in treating mixed-lineage leukemia (MLL) rearranged acute myelocytic leukemia). In certain embodiments, the composition is for use in treating cancer resistant to proteasome inhibitors. In certain embodiments, the composition is for use in treating cancer resistant to bortezomib. In certain embodiments, the composition is for use in treating cancer resistant to carfilzomib. In certain embodiments, the composition is for use in treating multiple myeloma.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (TWEEN® 20), polyoxyethylene sorbitan (TWEEN® 60), polyoxyethylene sorbitan monooleate (TWEEN® 80), sorbitan monopalmitate (SPAN® 40), sorbitan monostearate (SPAN® 60), sorbitan tristearate (SPAN® 65), glyceryl monooleate, sorbitan monooleate (SPAN® 80), polyoxyethylene esters (e.g., polyoxyethylene monostearate (MYRJ® 45), polyoxyethylene hydrogenated castor oil, polyethoxylated castor oil, polyoxymethylene stearate, and SOLUTOL®), sucrose fatty acid esters, polyethylene glycol fatty acid esters (e.g., CREMOPHOR®), polyoxyethylene ethers, (e.g., polyoxyethylene lauryl ether (BRIJ® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, PLURIONIC® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (VEEGUM®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, GLYDANT® Plus, PHENONIP®, methylparaben, GERMALL® 115, GERMABEN® II, NEOLONE®, KATHON®, and EUXYL®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as CREMOPHOR®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner.

Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a compound described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the compound or pharmaceutical composition described herein is suitable for topical administration to the eye of a subject.

The exact amount of a compound required to achieve an effective amount will vary from subject to subject, depending, for example, on species, age, and general condition of a subject, severity of the side effects or disorder, identity of the particular compound, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of a compound described herein. In certain embodiments, when multiple doses are administered to a subject or applied to a biological sample, tissue, or cell, the frequency of administering the multiple doses to the subject or applying the multiple doses to the biological sample, tissue, or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the biological sample, tissue, or cell is one dose per day. In certain embodiments, the frequency of administering the multiple doses to the subject or applying the multiple doses to the biological sample, tissue, or cell is two doses per day. In certain embodiments, the frequency of administering the multiple doses to the subject or applying the multiple doses to the biological sample, tissue, or cell is three doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 0.1 µg and 1 µg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a compound described herein. In certain embodiments, a dose described herein includes independently between 1 mg and 3 mg, inclusive, of a compound described herein. In certain embodiments, a dose described herein includes independently between 3 mg and 10 mg, inclusive, of a compound described herein. In certain embodiments, a dose described herein includes independently between 10 mg and 30 mg, inclusive, of a compound described herein. In certain embodiments, a dose described herein includes independently between 30 mg and 100 mg, inclusive, of a compound described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

A compound or composition, as described herein, can be administered in combination with one or more additional pharmaceutical agents (e.g., therapeutically and/or prophylactically active agents). The compounds or compositions can be administered in combination with additional pharmaceutical agents that improve their activity (e.g., activity (e.g., potency and/or efficacy) in treating a disease in a subject in need thereof, in preventing a disease in a subject in need thereof, in inducing the degradation of a target protein, and/or in reducing the risk to develop a disease in a subject in need thereof), improve bioavailability, improve their ability to cross the blood-brain barrier, improve safety, reduce drug resistance, reduce and/or modify metabolism, inhibit excretion, and/or modify distribution in a subject, biological sample, tissue, or cell. It will also be appreciated that the therapy employed may achieve a desired effect for the same disorder, and/or it may achieve different effects. In certain embodiments, a pharmaceutical composition described herein including a compound described herein and an additional pharmaceutical agent exhibit a synergistic effect that is absent in a pharmaceutical composition including one of the compound and the additional pharmaceutical agent, but not both.

The compound or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease). Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the compound described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, cytotoxic chemotherapeutic agents, epigenetic modifiers, glucocorticoids, immunotherapeutic agents, anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, pain-relieving agents, and a combination thereof. In certain embodiments, the additional pharmaceutical agent is an anti-proliferative agent (e.g., anti-cancer agent). In certain embodiments, the additional pharmaceutical agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase *Erwinia chrysanthemi* (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), ixazomib (e.g., NINLARO), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPOX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMBOCHLORIN, AMBOCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R—CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLASTONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARESTON), tositumomab and iodine 1131 tositumomab (e.g., BEXXAR), TPF, trametinib (e.g., MEKINIST), trastuzumab (e.g., HERCEPTIN), VAMP, vandetanib (e.g., CAPRELSA), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), or zoledronic acid (e.g., ZOMETA). In certain embodiments, the additional pharmaceutical agent is ENMD-2076, PCI-32765, AC220, dovitinib lactate (e.g., TKI258, CHIR-258), BIBW 2992 (e.g., TOVOK™), SGX523, PF-04217903, PF-02341066, PF-299804, BMS-777607, ABT-869, MP470, BIBF 1120 (e.g., VARGATEF®), AP24534, JNJ-26483327, MGCD265, DCC-2036, BMS-690154, CEP-11981, tivozanib (e.g., AV-951), OSI-930, MM-121, XL-184, XL-647, and/or XL228), proteasome inhibitors (e.g., bortezomib (e.g., Velcade)), mTOR inhibitors (e.g., rapamycin, temsirolimus (e.g., CCI-779), everolimus (e.g., RAD-001), ridaforolimus, AP23573 (e.g., Ariad), AZD8055, BEZ235, BGT226, XL765, PF-4691502, GDC0980, SF1126, and OSI-027), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine, or a combination thereof. In certain embodiments, the additional pharmaceutical agent is a cytotoxic chemotherapy (e.g., cytotoxic chemotherapeutic agent (e.g., gemcitabine, cytarabine, daunorubicin, doxorubicin, vincristine, 1-asparaginase, cyclophosphamide, or etoposide)). In certain embodiments, the additional pharmaceutical agent is an epigenetic modifier, such as azacitidine or romidepsin. In certain embodiments, the additional pharmaceutical agent is ruxolitinib, BBT594, CHZ868, CYT387, or BMS911543. In certain embodiments, the additional pharmaceutical agent is an inhibitor of a tyrosine kinase. In some embodiments, the additional pharmaceutical agent is a topoisomerase inhibitor, a MCL1 inhibitor, a BCL-2 inhibitor, a BCL-xL inhibitor, a BRD4 inhibitor, a BRCA1 inhibitor, BRCA2 inhibitor, HER1 inhibitor, HER2 inhibitor, a CDK9 inhibitor, a Jumonji histone demethylase inhibitor, or a DNA damage inducer. In some embodiments, the additional pharmaceutical agent is etoposide, obatoclax, navitoclax, JQ1, 4-(((5'-chloro-2'-(((1R,4R)-4-(((R)-1-methoxypropan-2-yl)amino)cyclohexyl)amino)-[2,4'-bipyridin]-6-yl)amino)methyl)tetrahydro-2H-pyran-4-carbonitrile, JIB04, or cisplatin. In certain embodiments, the additional pharmaceutical agent is a binder or inhibitor of a kinase (e.g., CDK). In certain embodiments, the additional pharmaceutical agent is an antibody or a fragment thereof (e.g., monoclonal antibody). In certain embodiments, the additional pharmaceutical agent is a tyrosine kinase inhibitor. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the additional pharmaceutical agent is a glucocorticoid (e.g., cortisol, cortisone, prednisone, methylprednisolone, dexamethasone, betamethasone, triamcinolone, fludrocortisone acetate, or deoxycorticosterone acetate). In certain embodiments, the additional therapy is an immunotherapy (e.g., an immunotherapeutic monoclonal antibody). In certain embodiments, the additional pharmaceutical agent is an immunomodulator. In certain embodiments, the additional pharmaceutical agent is an immune checkpoint inhibitor. In certain embodiments, the additional pharmaceutical agent is a programmed cell death 1 protein (PD-1) inhibitor. In certain embodiments, the additional pharmaceutical agent is a programmed cell death 1 protein ligand 1 (PD-L1) inhibitor. In certain embodiments, the additional pharmaceutical agent is a cytotoxic T-lymphocyte-associated protein 4 (CTLA-4) inhibitor. In certain embodiments, the additional pharmaceutical agent is a T-cell immunoglobulin domain and mucin domain 3 (TIM3) inhibitor, lymphocyte activation gene-3 (LAG3) inhibitor, V-set domain-containing T-cell activation inhibitor 1 (VTCN1 or B7-H4) inhibitor, cluster of differentiation 276 (CD276 or B7-H3) inhibitor, B and T lymphocyte attenuator (BTLA) inhibitor, galectin-9 (GAL9) inhibitor, checkpoint kinase 1 (Chk1) inhibitor, adenosine A2A receptor (A2AR) inhibitor, indoleamine 2,3-dioxygenase (IDO) inhibitor, killer-cell immunoglobulin-like receptor (KIR) inhibitor, or V-domain Ig suppressor of T cell activation (VISTA) inhibitor. In certain embodiments, the PD-1 inhibitor is nivolumab, pidilizumab, pembrolizumab, MEDI-0680, REGN2810, or AMP-224. In certain embodiments, the PD-L1 inhibitor is atezolizumab, durvalumab, BMS-936559, avelumab, or CA-170. In certain embodiments, the CTLA-4 inhibitor is ipilimumab or tremelimumab. In certain embodiments, the additional pharmaceutical agent is an aromatase inhibitor. In certain embodiments, the compounds described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy. In certain embodiments, the compounds described herein or pharmaceutical compositions can be administered in combination with immunotherapy and/or chemotherapy. In certain embodiments, the compounds described herein or pharmaceutical compositions can be administered in combination with immunotherapy. In certain embodiments, the compounds described herein or pharmaceutical compositions can be administered in combination with chemotherapy.

Also encompassed by the disclosure are kits (e.g., pharmaceutical packs). The kits provided may comprise a pharmaceutical composition or compound described herein and a container (e.g., a vial, ampule, bottle, syringe, and/or dispenser package, or other suitable container). In some embodiments, provided kits may optionally further include a second container comprising a pharmaceutical excipient for dilution or suspension of a pharmaceutical composition or compound described herein. In some embodiments, the pharmaceutical composition or compound described herein provided in the first container and the second container are combined to form one unit dosage form.

Thus, in one aspect, provided are kits including a first container comprising a compound or pharmaceutical composition described herein. In certain embodiments, the kits are useful for treating a disease (e.g., proliferative disease) in a subject in need thereof. In certain embodiments, the kits are useful for preventing a disease (e.g., proliferative disease) in a subject in need thereof.

In certain embodiments, a kit described herein further includes instructions for using the compound or pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for treating a disease (e.g., proliferative disease) in a subject in need thereof. In certain embodiments, the kits and instructions provide for preventing a disease (e.g., proliferative disease) in a subject in need thereof. In certain embodiments, the kits and instructions provide for inducing the degradation of target protein DOT1L in a subject, biological sample, tissue, or cell. A kit described herein may include one or more additional pharmaceutical agents described herein as a separate composition.

Methods of Treatment and Uses

The compounds described herein are capable of binding (e.g., irreversibly binding) the ubiquitin receptor RPN13 and the target protein DOT1L and inducing the degradation of the target protein DOT1L. The present disclosure thus also provides methods of inducing the degradation of the target protein DOT1L in a subject, biological sample, tissue, or cell. The present disclosure further provides methods for the treatment of diseases, such as proliferative diseases, in a subject in need thereof.

In certain embodiments, the application provides a method of binding an ubiquitin receptor RPN13 and promoting the degradation of the target protein DOT1L. In another aspect, the present disclosure provides methods of inducing the degradation of the target protein DOT1L in a subject in need thereof, the methods comprise administering to the subject an effective amount of a compound or pharmaceutical composition described herein. In another aspect, the present disclosure provides methods of inducing the degradation of the target protein DOT1L in a biological sample, tissue, or cell, the methods comprise contacting the biological sample, tissue, or cell with an effective amount of a compound or pharmaceutical composition described herein.

In certain embodiments, the application provides a method of binding the ubiquitin receptor RPN13 and the target protein DOT1L and inducing the degradation of the target protein DOT1L. In certain embodiments, the binder of the target protein DOT1L is of the formula:

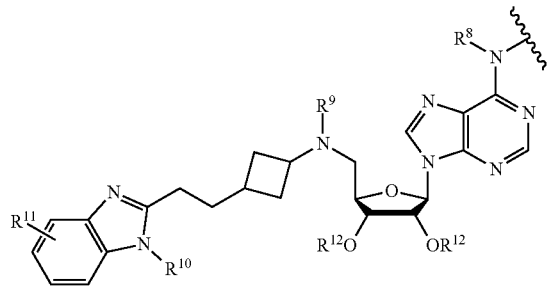

Use of a bifunctional compound that binds the ubiquitin receptor RPN13 and the target protein DOT1L provides a strategy for treating diseases associated with DOT1L (e.g. proliferative diseases), as research tools for studying the role of DOT1L in the cell, or as research tools for studying diseases associated with DOT1L (e.g. proliferative diseases).

The present disclosure also provides a compound of Formula (I), or a pharmaceutically acceptable salt, co-crystal, tautomer, stereoisomer, solvate, hydrate, polymorph, isotopically enriched derivative, or prodrug, or composition thereof, for use in the treatment of diseases, such as proliferative diseases, in a subject in need thereof.

The present disclosure also provides uses of a compound of Formula (I), or a pharmaceutically acceptable salt, co-crystal, tautomer, stereoisomer, solvate, hydrate, polymorph, isotopically enriched derivative, or prodrug, or composition thereof, in the manufacture of a medicament for the treatment of diseases, such as proliferative diseases, in a subject in need thereof.

In certain embodiments, the methods of the disclosure comprise administering to the subject an effective amount of a compound of Formula (I), or a pharmaceutically acceptable salt, co-crystal, tautomer, stereoisomer, solvate, hydrate, polymorph, isotopically enriched derivative, or prodrug, or composition thereof. In some embodiments, the effective amount is a therapeutically effective amount. In some embodiments, the effective amount is a prophylactically effective amount.

In certain embodiments, the subject being treated is an animal. The animal may be of either sex and may be at any stage of development. In certain embodiments, the subject is a mammal. In certain embodiments, the subject being treated is a human. In certain embodiments, the subject is a domesticated animal, such as a dog, cat, cow, pig, horse, sheep, or goat. In certain embodiments, the subject is a companion animal, such as a dog or cat. In certain embodiments, the subject is a livestock animal, such as a cow, pig, horse, sheep, or goat. In certain embodiments, the subject is a zoo animal. In another embodiment, the subject is a research animal such as a rodent (e.g., mouse, rat), dog, pig, or non-human primate. In certain embodiments, the animal is a genetically engineered animal. In certain embodiments, the animal is a transgenic animal.

Certain methods described herein may comprise administering one or more additional pharmaceutical agent(s) in combination with the compounds described herein. The additional pharmaceutical agent(s) may be administered at the same time as the compound of Formula (I), or at different times than the compound of Formula (I). For example, the compound of Formula (I) and any additional pharmaceutical agent(s) may be on the same dosing schedule or different dosing schedules. All or some doses of the compound of Formula (I) may be administered before all or some doses of an additional pharmaceutical agent, after all or some does an additional pharmaceutical agent, within a dosing schedule of an additional pharmaceutical agent, or a combination thereof. The timing of administration of the compound of Formula (I) and additional pharmaceutical agents may be different for different additional pharmaceutical agents.

In certain embodiments, the additional pharmaceutical agent comprises an agent useful in the treatment of diseases, such as proliferative diseases, in a subject in need thereof. In certain embodiments, the additional pharmaceutical agent is useful in the treatment of a proliferative disease. In certain embodiments, the additional pharmaceutical agent is useful in the treatment of an inflammatory disease. In certain embodiments, the additional pharmaceutical agent is useful in the treatment of proliferative diseases. In certain embodiments, the additional pharmaceutical agent is useful in the treatment of multiple myeloma. In certain embodiments, the additional pharmaceutical agent is useful in the treatment of leukemia. In certain embodiments, the additional pharmaceutical agent is useful in the treatment of acute myelocytic leukemia. In certain embodiments, the additional pharmaceutical agent is useful in the treatment of mixed-lineage leukemia (MLL) rearranged acute myelocytic leukemia. In certain embodiments, the additional pharmaceutical agent is useful in the treatment of acute myelocytic leukemia with a mutation in the nucleophosmin (NPM1) gene. In certain embodiments, the additional pharmaceutical agent is useful in the treatment of acute myelocytic leukemia with a mutation in the DNMT3A gene. In certain embodiments, the additional pharmaceutical agent is useful in the treatment of lymphoma. In certain embodiments, the additional pharmaceutical agent is useful in the treatment of a non-Hodgkin's lymphoma. In certain embodiments, the additional pharmaceutical agent is useful in the treatment of cancer resistant to proteasome inhibitors (e.g., resistant to bortezomib).

In another aspect, the present disclosure provides methods for inducing the degradation of DOT1L, the method comprising administering to the subject a compound of Formula (I), or a pharmaceutically acceptable salt, co-crystal, tautomer, stereoisomer, solvate, hydrate, polymorph, isotopically enriched derivative, or prodrug, or composition thereof.

In another aspect, the present disclosure provides methods for binding the ubiquitin receptor RPN13 and promoting the degradation and/or ubiquitination of DOT1L, the method comprising administering to the subject a compound of Formula (I), or a pharmaceutically acceptable salt, co-crystal, tautomer, stereoisomer, solvate, hydrate, polymorph, isotopically enriched derivative, or prodrug, or composition thereof. In certain embodiments, provided are methods of treating cancers resistant to standard cancer treatment. In certain embodiments, provided are methods of treating cancers resistant to proteasome inhibitors.

In still another aspect, the present disclosure provides pharmaceutical compositions described herein for use in binding the ubiquitin receptor RPN13 and DOT1L and promoting the degradation of DOT1L; inducing the ubiquitination of DOT1L in a subject, biological sample, tissue, or cell; and treating and/or preventing proliferative diseases.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

The compounds (e.g., compounds of Formula (I)) provided herein can be prepared from readily available starting materials using the following general methods and procedures or methods known in the art. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by those skilled in the art by routine optimization procedures.

Example 1. Biological Assays of Exemplary Compounds with DOT1L

Figure 9A:
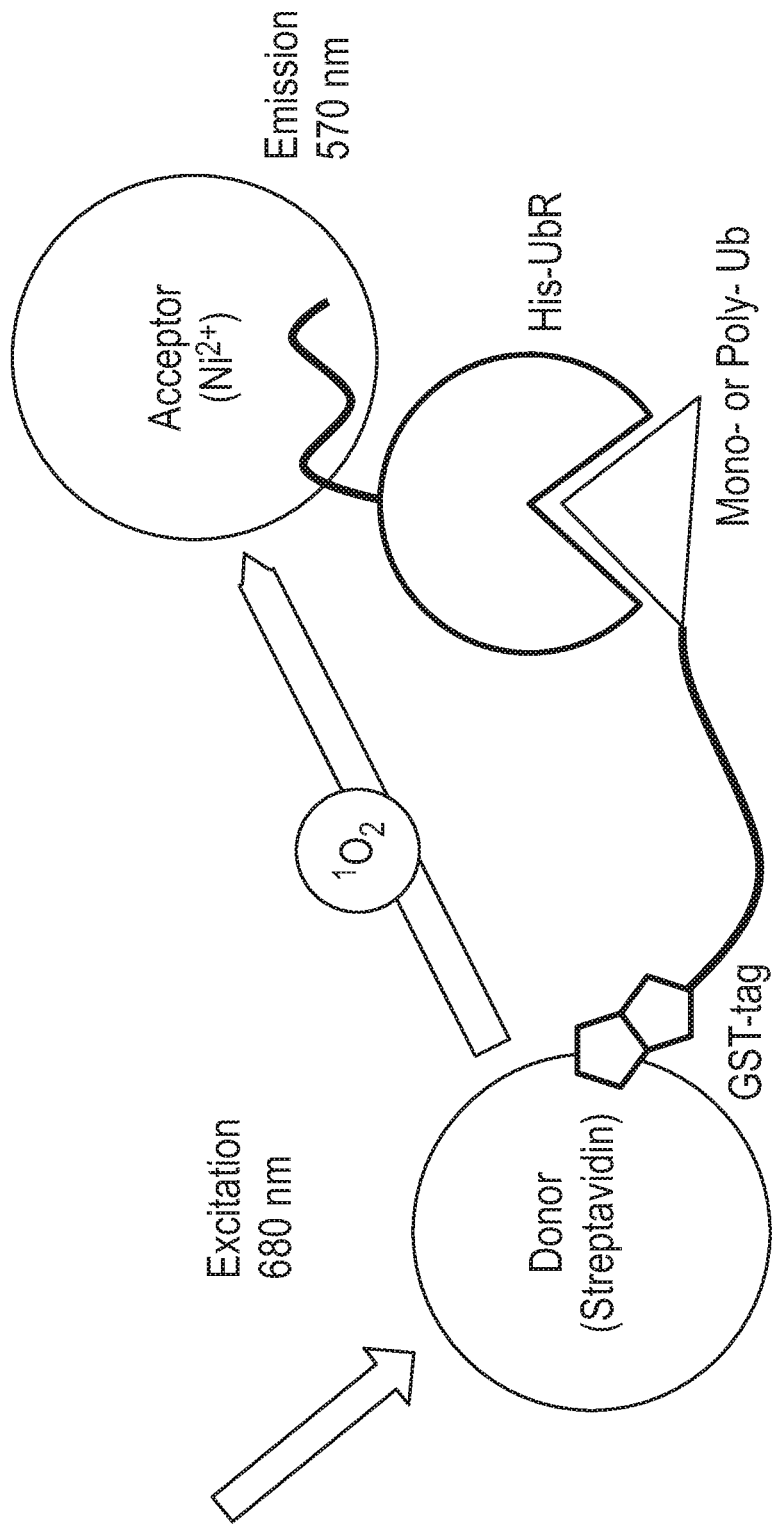
Figure 9B:
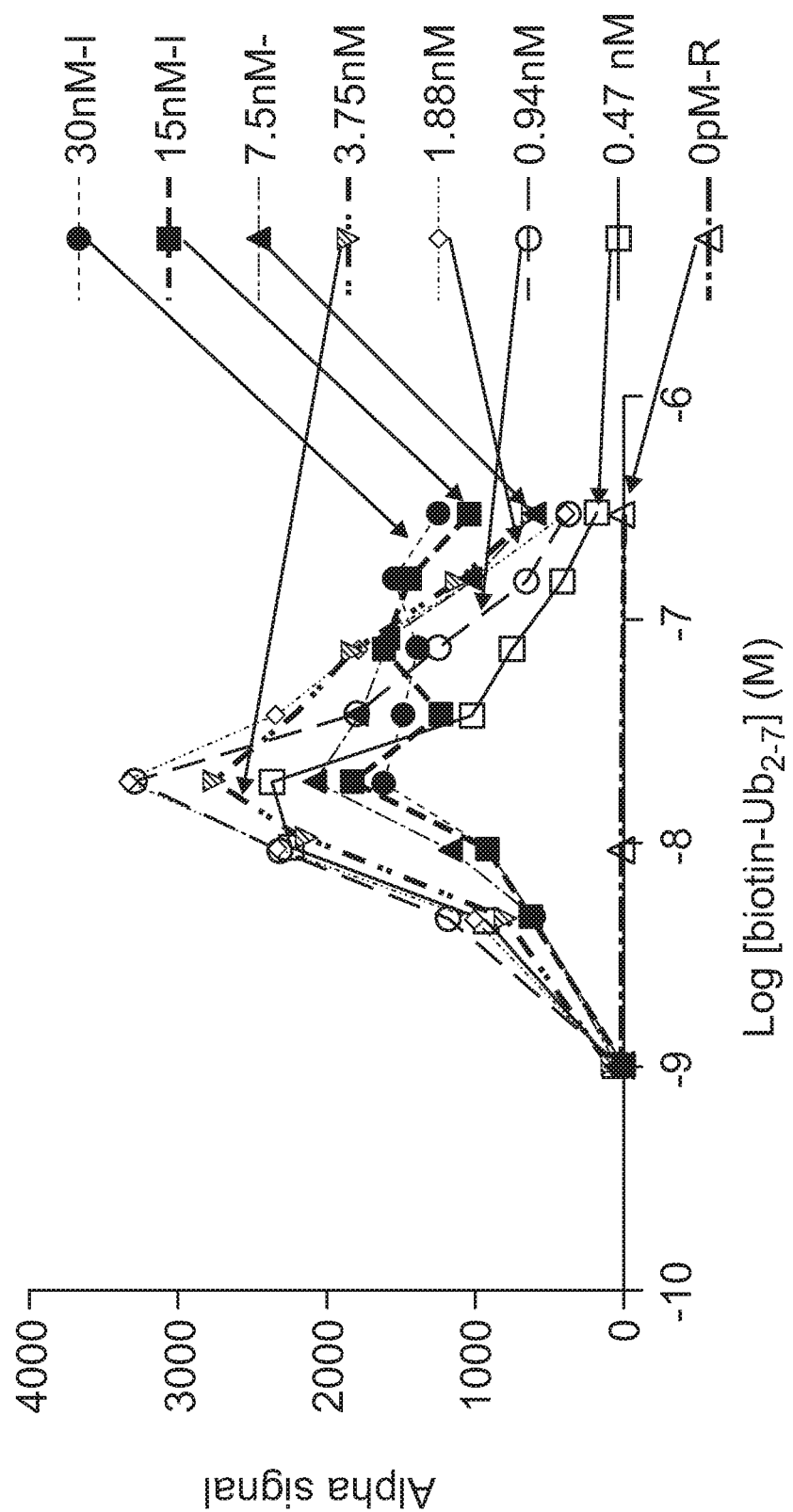
Figure 10C:
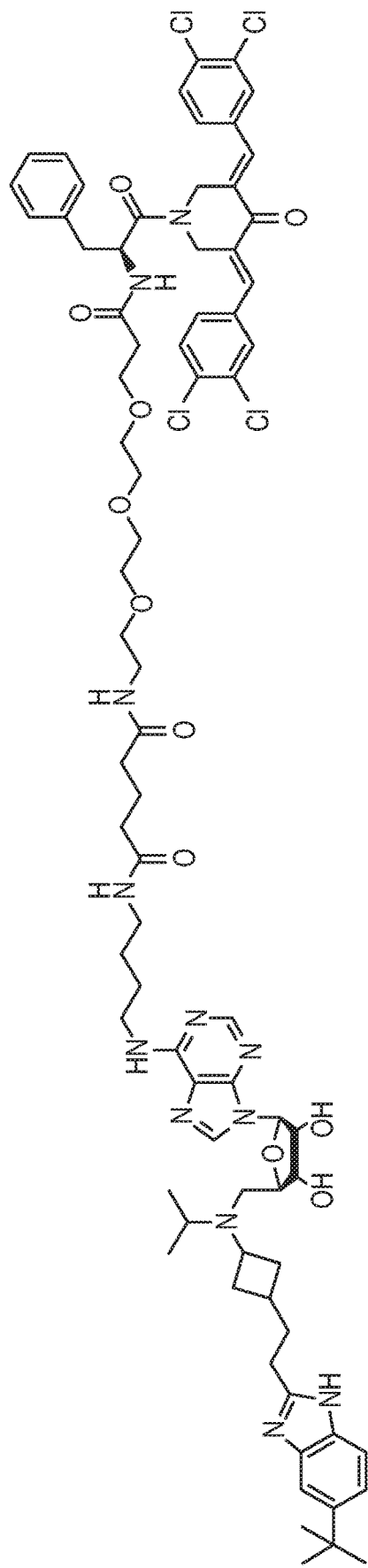

A biochemical assay was run to identify target inhibitors that can disrupt the binding of RPN13 with poly-ubiquitinylation. The assay was optimized based on concentrations of the target inhibitors, concentrations of compound RA190, and in view of the alpha signal. The conditions for the biochemical assay are recognized by those of ordinary skill in the art. See FIGS. 9A-9C.

Degradation by dDOT1L-6 in Molm13 PA Cell Line

Figure 11A:
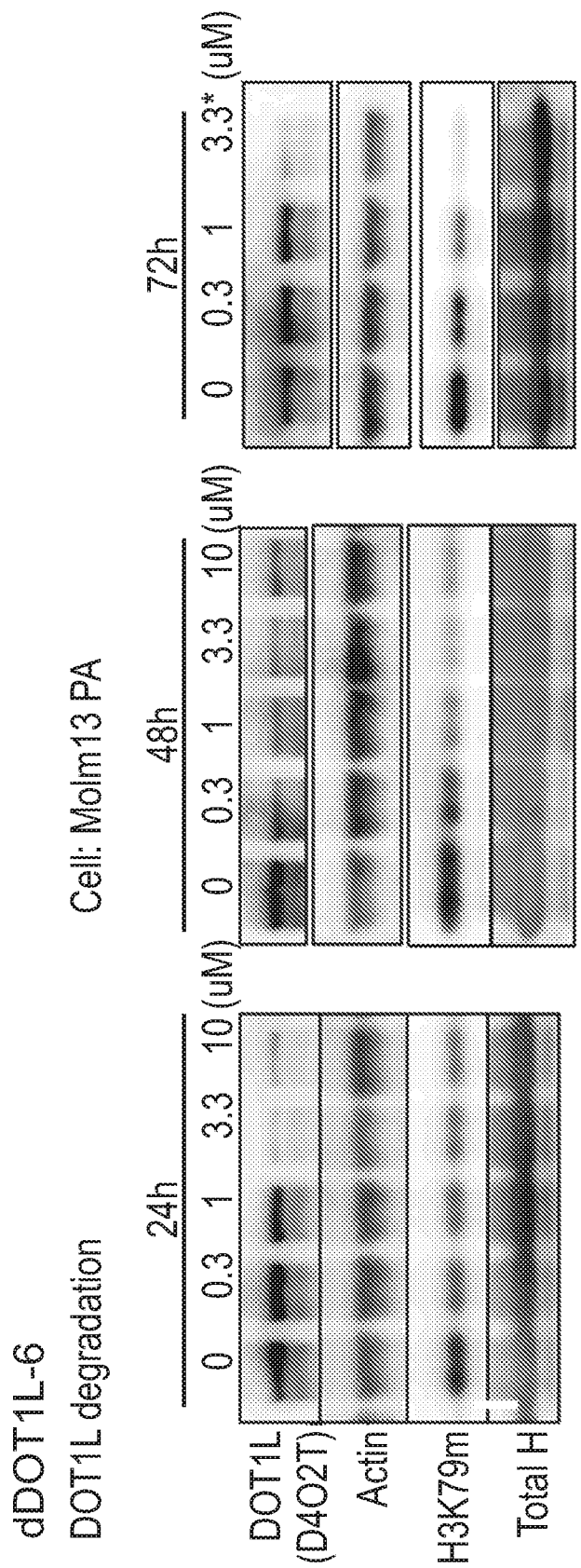
FIGS. 11A-11B show a Western blot of an assay where the antibody D402T was used to confirm the DOT1L protein levels in acute myeloid leukemia cells (Molm13 PA) treated with DOT1L-6 (FIG. 11A) and DOT1L-7 (FIG. 11B) at the indicated concentrations (0 µM, 0.3 µM, 1 µM, 3.3 µM, and 10 µM) for the indicated amount of time (24 hours, 48 hours, and 72 hours). The cells were immunoblotted with DOT1L (D402T), actin, and H3K79me2. These cells show DOT1L degradation.

Molm13PA (acute myeloid leukemia) cells were treated with dDOT1L-6 at 0 µM, 0.3 µM, 1 µM, 3.3 µM, and 10 µM for 24 hours, 48 hours, and 72 hours. Cell lysates were loaded on SDS-PAGE, then immunoblotted with DOT1L (D402T), actin, and H3K79me2. The antibody D402T was used to confirm the DOT1L protein level. The Western blots show that dDOT1L-6 inhibits acute myeloid leukemia cells (Molm13 PA). (see FIG. 11A). These cells show DOT1L degradation. (see FIG. 11A).

Degradation by dDOT1L-7 in Molm13 PA Cell Line

Figure 11B:
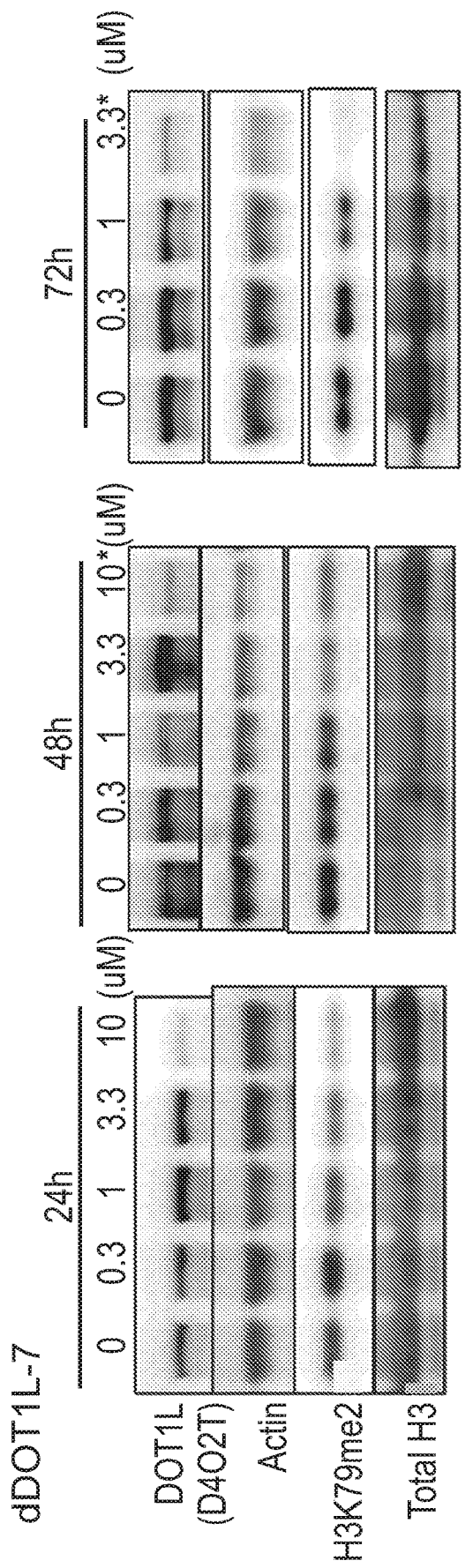
Figure 12A:
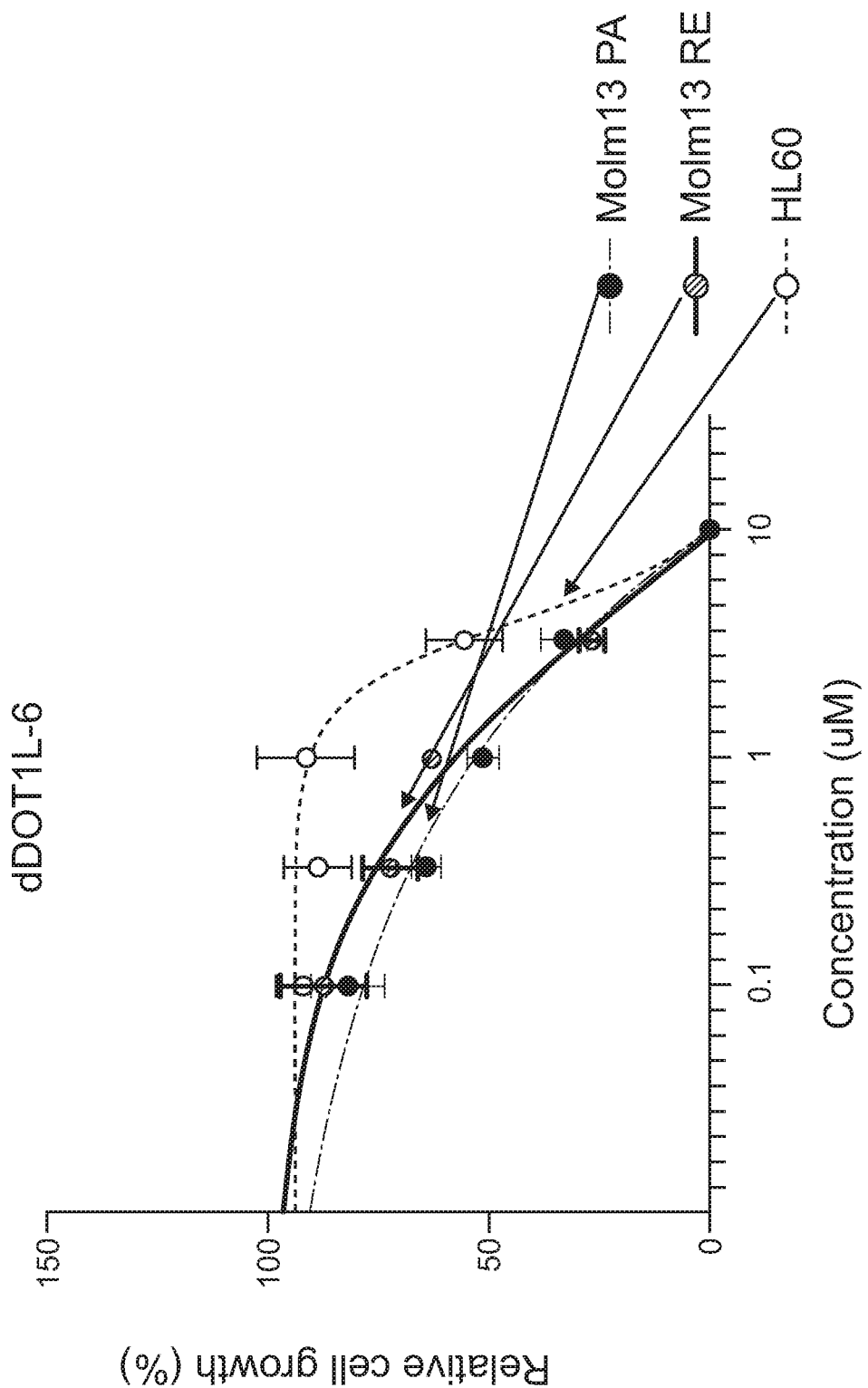
FIGS. 12A-12D show a Western blot of an assay where MOLM 13 cells were treated with exemplary DOT1L degraders and then the cell numbers were counted over time to confirm the cellular activity of the cells.
Figure 12B:
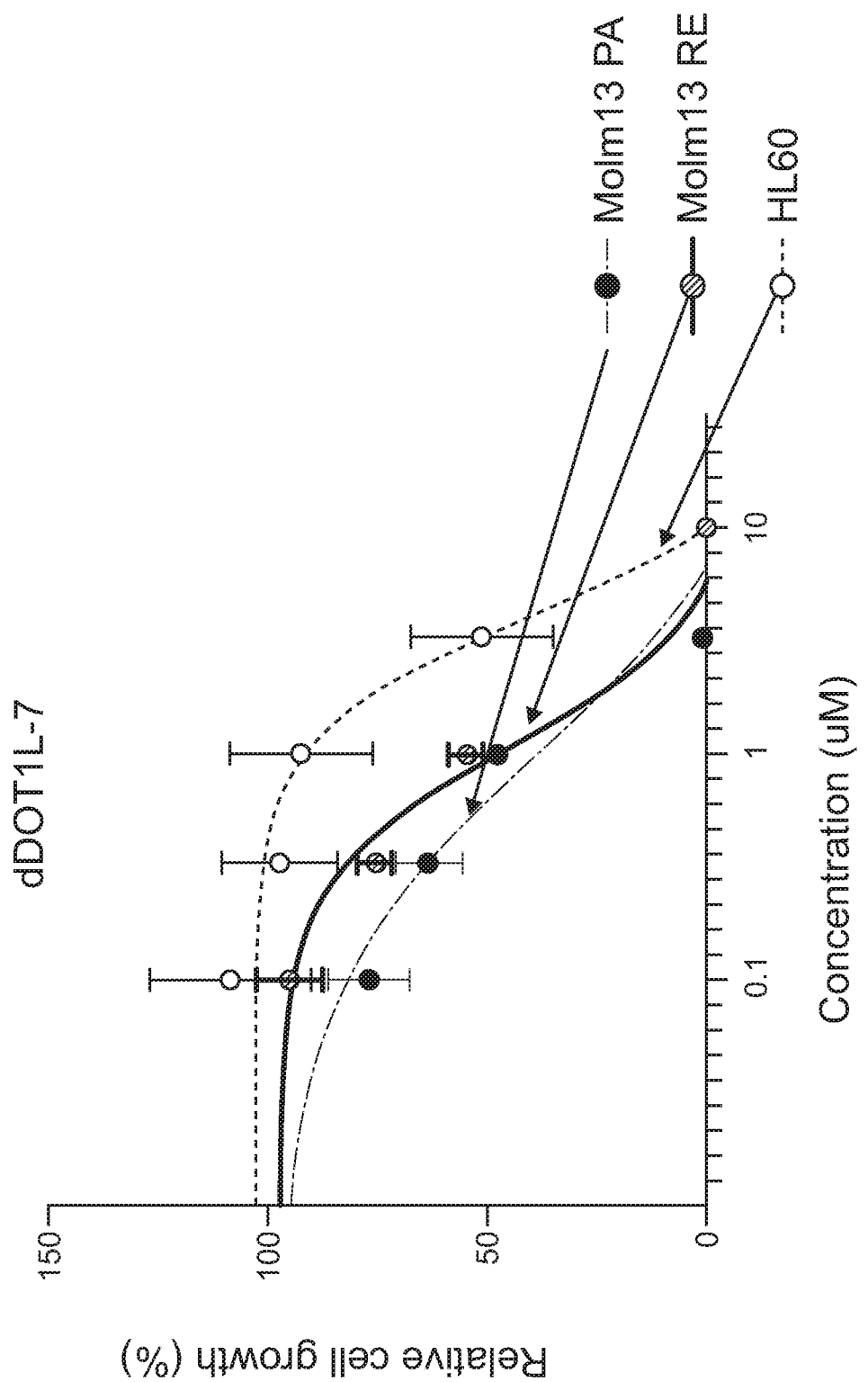
Figure 12C:
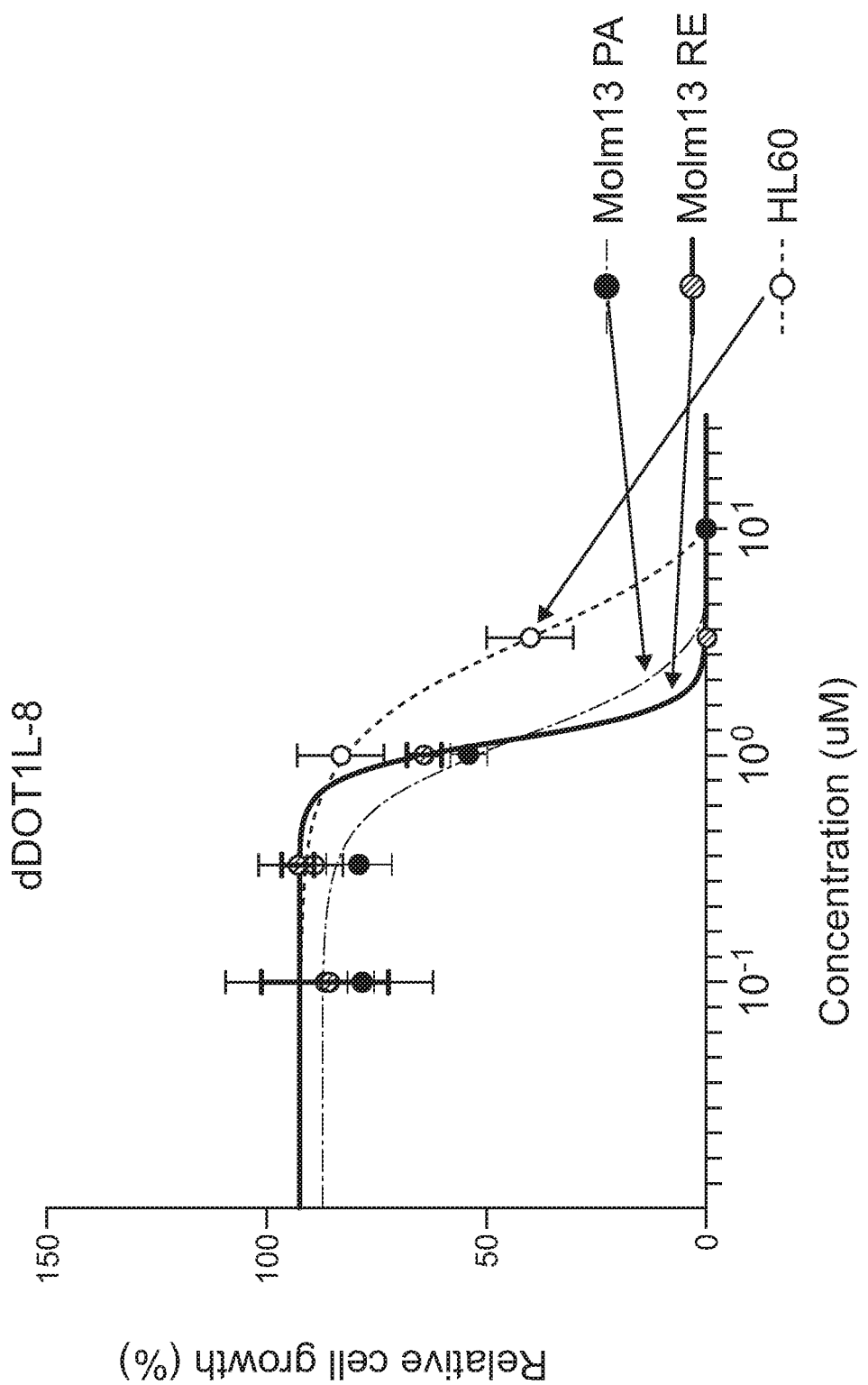
Figure 12D:
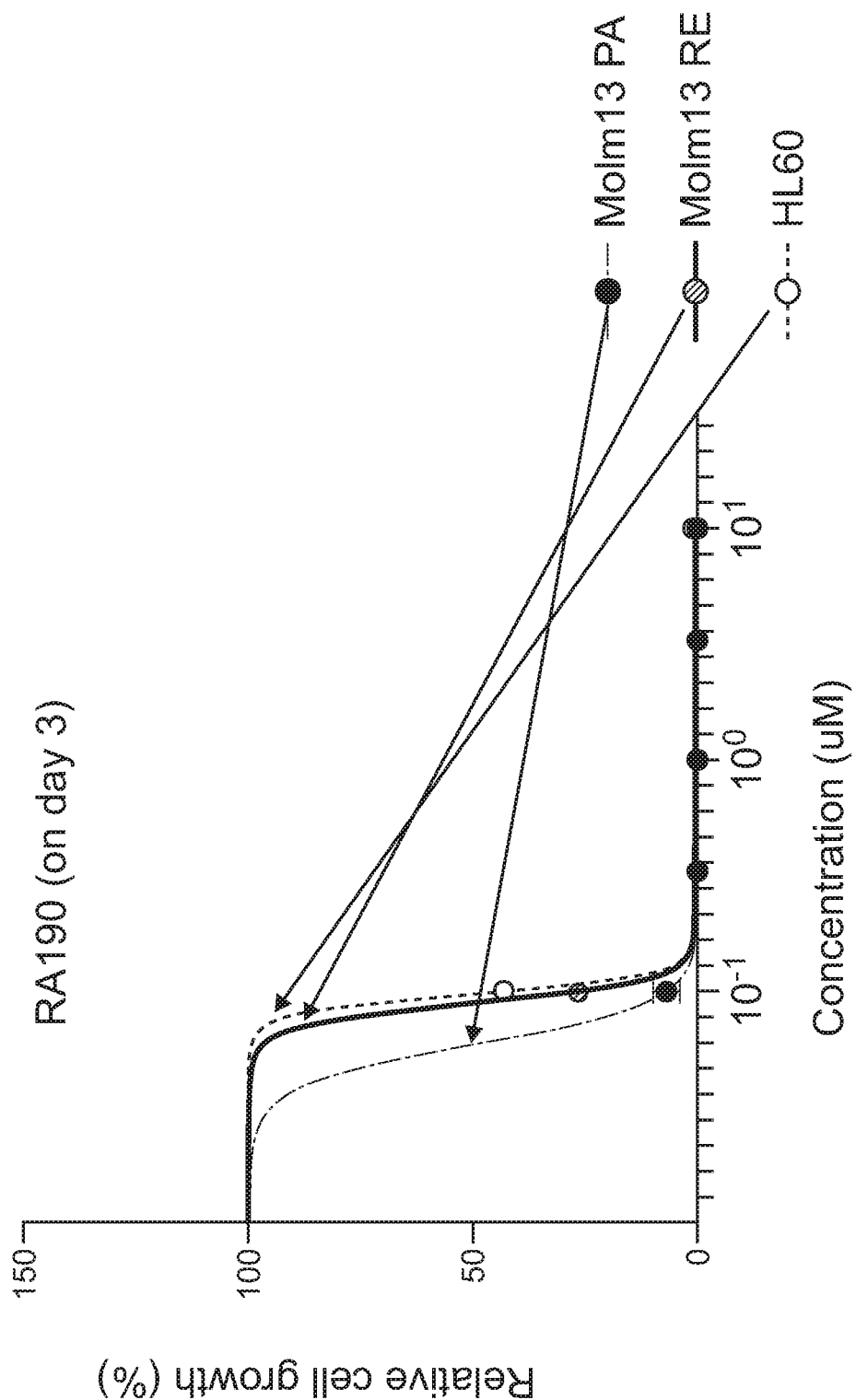

Molm13PA (acute myeloid leukemia) cells were treated with dDOT1L-7 at 0 µM, 0.3 µM, 1 µM, 3.3 µM, and 10 µM for 24 hours, 48 hours, and 72 hours. Cell lysates were loaded on SDS-PAGE, then immunoblotted with DOT1L (D402T), actin, and H3K79me2. The blots show that dDOT1L-7 inhibits acute myeloid leukemia cells (Molm13 PA). (see FIG. 11B). These cells show DOT1L degradation. (see FIG. 11B).

Relative Cell Growth in the Presence of Exemplary Thalidomide-Based, DOT1L Degrader Compounds Molm13 PA (acute myeloid leukemia), Molm13 RE (acute myeloid leukemia), and HL60 (human leukemia) cells were treated with exemplary thalidomide-based, DOT1L degrader compounds DOT1L-6, DOT1L-7, DOT1L-8, and RA190 at various concentrations between 0 and 10 µM. The relative cell growth of the Molm13 PA, Molm13 RE, and HL60 cells was measured to analyze cellular activity after 10 days. The results show that there was reduced cell growth (based on cell count) for the Molm13 leukemia cells and HL60 (human leukemia) cells that were treated with exemplary DOT1L degrader compounds, with increased concentration of the exemplary DOT1L degrader compounds (see FIGS. 12A-12D).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects described herein, is/are referred to as comprising particular elements and/or features, certain embodiments described herein or aspects described herein consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included.

Furthermore, unless otherwise indicated or otherwise evident from the context and understanding of one of ordinary skill in the art, values that are expressed as ranges can assume any specific value or sub-range within the stated ranges in different embodiments described herein, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present disclosure that falls within the prior art may be explicitly excluded from any one or more of the claims.

Because such embodiments are deemed to be known to one of ordinary skill in the art, they may be excluded even if the exclusion is not set forth explicitly herein. Any particular embodiment described herein can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present disclosure, as defined in the following claims.

What is claimed is:

1. A compound of Formula (I):

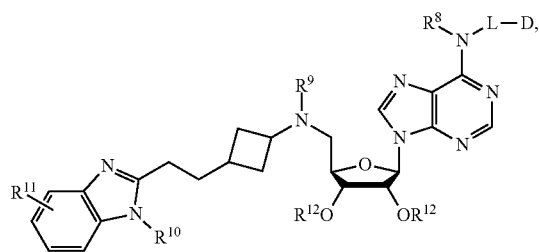

or a pharmaceutically acceptable salt, solvate, hydrate, tautomer, or stereoisomer thereof, wherein:

$R^8$ is hydrogen, optionally substituted acyl, optionally substituted alkyl, or a nitrogen protecting group;

$R^9$ is hydrogen, optionally substituted acyl, optionally substituted alkyl, or a nitrogen protecting group;

$R^{10}$ is hydrogen, optionally substituted acyl, optionally substituted alkyl, or a nitrogen protecting group;

$R^{11}$ is halogen, optionally substituted acyl, or optionally substituted alkyl;

each instance of $R^{12}$ is independently hydrogen, optionally substituted acyl, or an oxygen protecting group;

L is

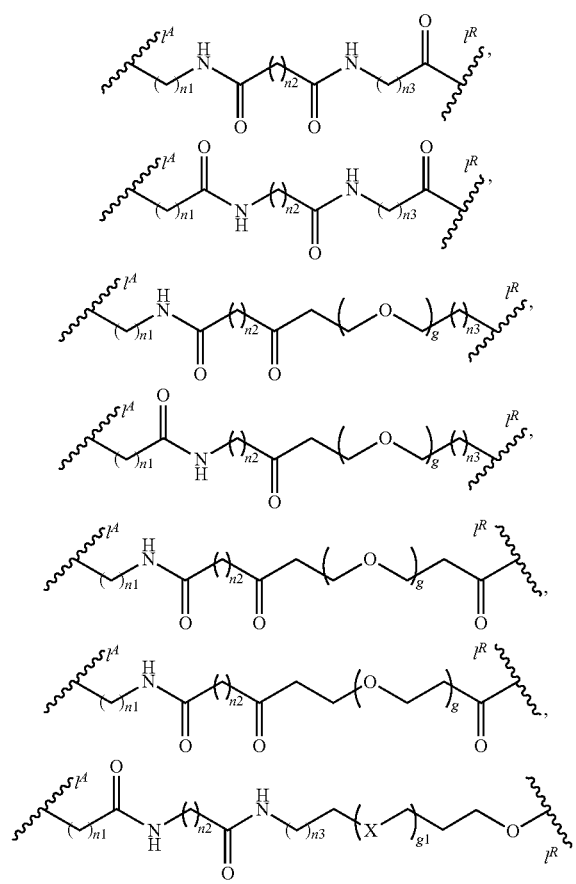

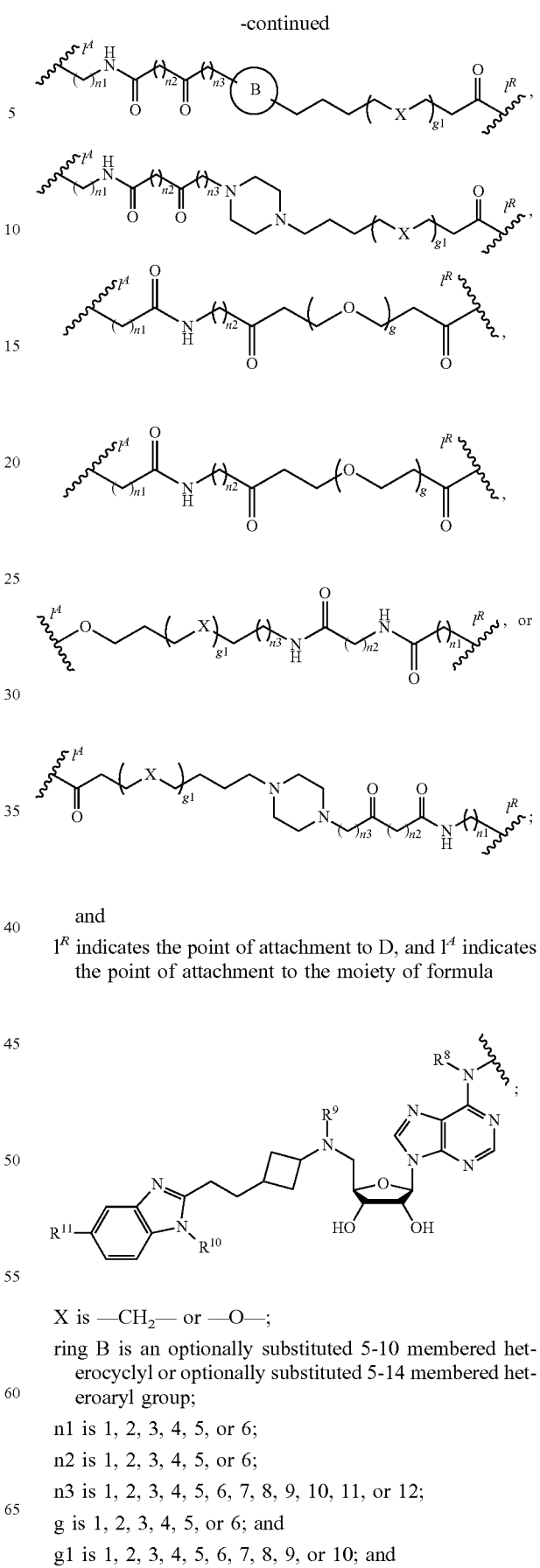

and $1^R$ indicates the point of attachment to D, and $1^A$ indicates the point of attachment to the moiety of formula X is —CH$_2$— or —O—;

ring B is an optionally substituted 5-10 membered heterocyclyl or optionally substituted 5-14 membered heteroaryl group;

n1 is 1, 2, 3, 4, 5, or 6;

n2 is 1, 2, 3, 4, 5, or 6;

n3 is 1, 2, 3, 4, 5, 6, 7, 8, 9, 10, 11, or 12;

g is 1, 2, 3, 4, 5, or 6; and g1 is 1, 2, 3, 4, 5, 6, 7, 8, 9, or 10; and

D is of the formula IA or IB:

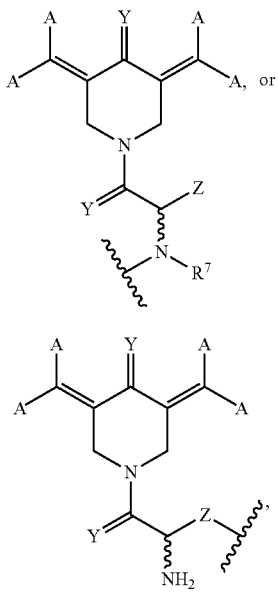

wherein:
for each set of two moieties A bound to the same carbon atom, one A is hydrogen, and the other A is one of:
(i) phenyl, optionally substituted with 1-5 substituents selected from the group consisting of —$R^1$, —$OR^1$, —$NR^1R^2$, —$S(O)_qR^1$, —$SO_2R^1R^2$, —$NR^1SO_2R^2$, —$C(O)R^1$, —$C(O)OR^1$, —$C(O)NR^1R^2$, —$NR^1C(O)R^2$, —$NR^1C(O)OR^2$, —$CHF_2$, —$CH_2F$, —$CF_3$, and —$OCF_3$;
(ii) naphthyl, optionally substituted with 1-5 substituents selected from the group consisting of —$R^1$, —$OR^1$, —$NR^1R^2$, —$S(O)_qR^1$, —$SO_2R^1R^2$, —$NR^1SO_2R^2$, —$C(O) R^1$, —$C(O)OR^1$, —$C(O)NR^1R^2$, —$NR^1C(O)R^2$, —$NR^1C(O)OR^2$, —$CHF_2$, —$CH_2F$, —$CF_3$, and —$OCF_3$;
(iii) a 5- or 6-membered monocyclic heteroaryl group, having 1-3 heteroatoms selected from the group consisting of O, N, and S, optionally substituted with 1-3 substituents selected from the group consisting of —$R^1$, —$OR^1$, —$NR^1R^2$, —$S(O)_qR^1$, —$SO_2R^1R^2$, —$NR^1SO_2R^2$, —$C(O) R^1$, —$C(O)OR^1$, —$C(O)NR^1R^2$, —$NR^1C(O) R^2$, —$NR^1C(O)OR^2$, —$CHF_2$, —$CH_2F$, —$CF_3$, and —$OCF_3$; and
(iv) an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with 1-3 substituents selected from the group consisting of —$R^1$, —$OR^1$, —$NR^1R^2$, —$S(O)_qR^1$, —$SO_2R^1R^2$, —$NR^1SO_2R^2$, —$C(O) R^1$, —$C(O)OR^1$, —$C(O)NR^1R^2$, —$NR^1C(O) R^2$, —$NR^1C(O)OR^2$, —$CHF_2$, —$CH_2F$, —$CF_3$, and —$OCF_3$;
Y is =O, =S, =$NR^1$, or =$CR^1R^2$, $R^1$ and $R^2$ are each independently selected from the group consisting of hydrogen, nitro, hydroxyl, —COOH, —$NH_2$, halogen, cyano, and $C_1$-$C_{14}$ alkyl optionally substituted with 1-3 substituents selected from the group consisting of $C_1$-$C_{14}$ alkyl, $C_1$-$C_{14}$ haloalkyl, $C_1$-$C_{14}$ alkoxy, nitro, hydroxyl, —COOH, —$NH_2$, $C_1$-$C_{14}$ alkylamino, $C_1$-$C_{14}$ dialkylamino, halogen, and cyano;
$R^7$ is hydrogen, optionally substituted $C_{1-6}$ alkyl, or a nitrogen protecting group;
Z is selected from the group consisting of hydrogen, optionally substituted $C_1$-$C_{14}$ alkyl, optionally substituted $C_3$-$C_{10}$ cycloalkyl, optionally substituted aryl, optionally substituted aralkyl, optionally substituted alkyl-aryl, and —$(CH_2)_p$—K;
K is a 5- or 6-membered monocyclic heterocyclic or heteroaryl group containing 1-4 heteroatoms selected from the group consisting of O, N, and S, or an 8- to 10-membered bicyclic heteroaryl group containing 1-4 heteroatoms selected from the group consisting of O, N, and S;
p is an integer selected from the group consisting of 0, 1, 2, 3, and 4; and
q is an integer selected from the group consisting of 0, 1, 2, 3, and 4.

2. The compound of claim 1, or a pharmaceutically acceptable salt, solvate, hydrate, tautomer, or stereoisomer thereof, wherein D is of the formula:

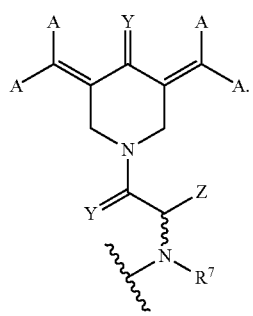

3. The compound of claim 2, wherein:
for each set of two moieties A bound to the same carbon atom, one A is hydrogen and the other A is phenyl optionally substituted with $R^1$;
for each set of two moieties A bound to the same carbon atom, one A is hydrogen and the other A is phenyl substituted with halogen;
for each set of two moieties A bound to the same carbon atom, one A is hydrogen and the other A is phenyl substituted with two instances of halogen;
for each set of two moieties A bound to the same carbon atom, one A is hydrogen and the other A is phenyl substituted with at least one Cl;
for each set of two moieties A bound to the same carbon atom, one A is hydrogen and the other A is naphthyl optionally substituted with $R^1$;
for each set of two moieties A bound to the same carbon atom, one A is hydrogen and the other A is a 5- or 6-membered monocyclic heteroaryl group, having 1-3 heteroatoms selected from the group consisting of O, N, and S, optionally substituted with $R^1$; or
for each set of two moieties A bound to the same carbon atom, one A is hydrogen and the other A is an 8- to 10-membered bicyclic heteroaryl group containing 1-3 heteroatoms selected from the group consisting of O, N, and S, and having a first ring fused to a second ring through 3 to 4 carbon atoms, wherein the bicyclic heteroaryl group is optionally substituted with $R^1$.

4. The compound of claim 2, wherein:
Y is =O;
Z is ($C_{1-3}$alkyl) phenyl, ($C_{1-3}$haloalkyl) phenyl, or phenyl; or
$R^7$ is hydrogen.

5. The compound of claim 4, wherein Z is benzyl.

6. The compound of claim 1, or a pharmaceutically acceptable salt, solvate, hydrate, tautomer, or stereoisomer thereof, wherein D is of formula:

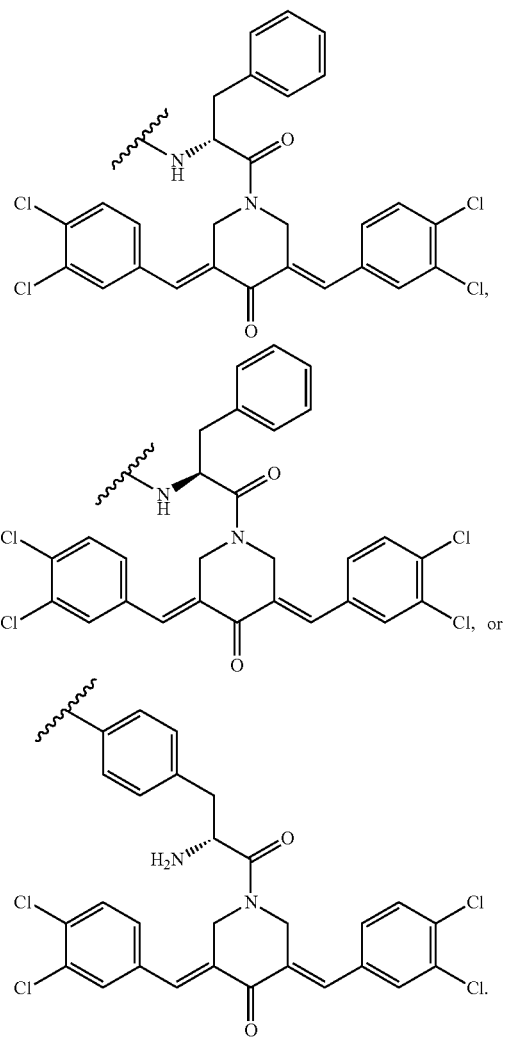

7. The compound of claim 1, wherein the compound is of

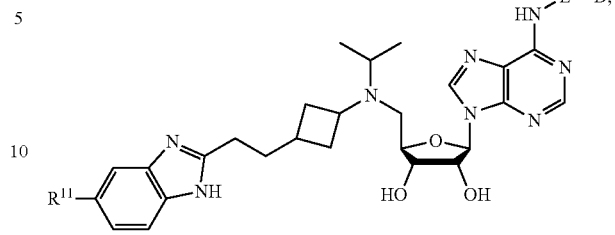

or a pharmaceutically acceptable salt, solvate, hydrate, tautomer, or stereoisomer thereof.

8. The compound of claim 7, wherein $R^{11}$ is optionally substituted $C_{1-6}$ alkyl.

9. The compound of claim 1, or a pharmaceutically acceptable salt thereof, wherein:

L is

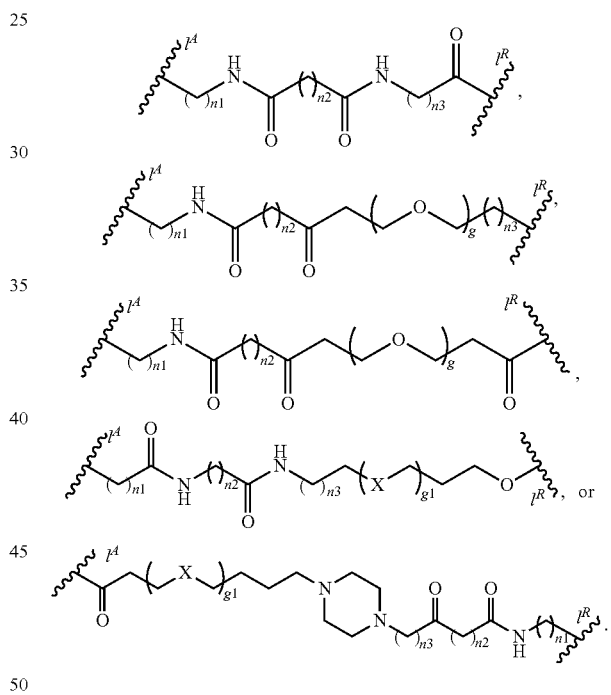

10. The compound of claim 1, wherein L is of the formula:

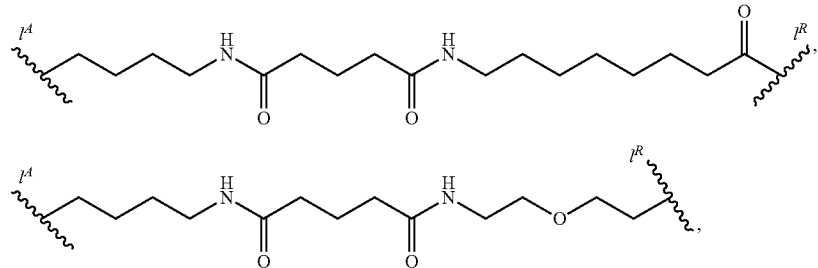

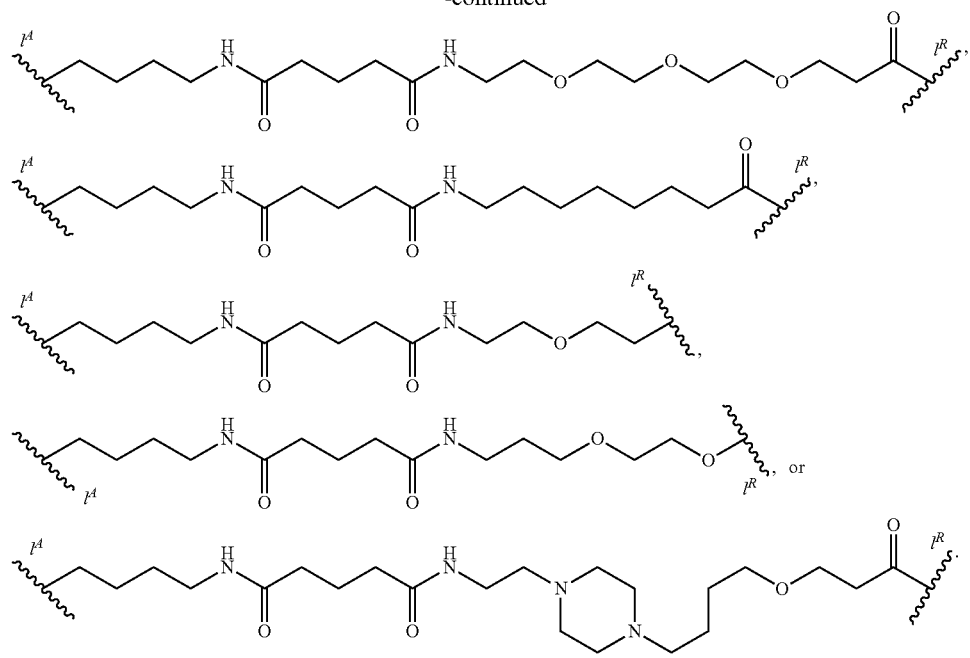
11. The compound of claim 1, wherein the compound is of the formula:
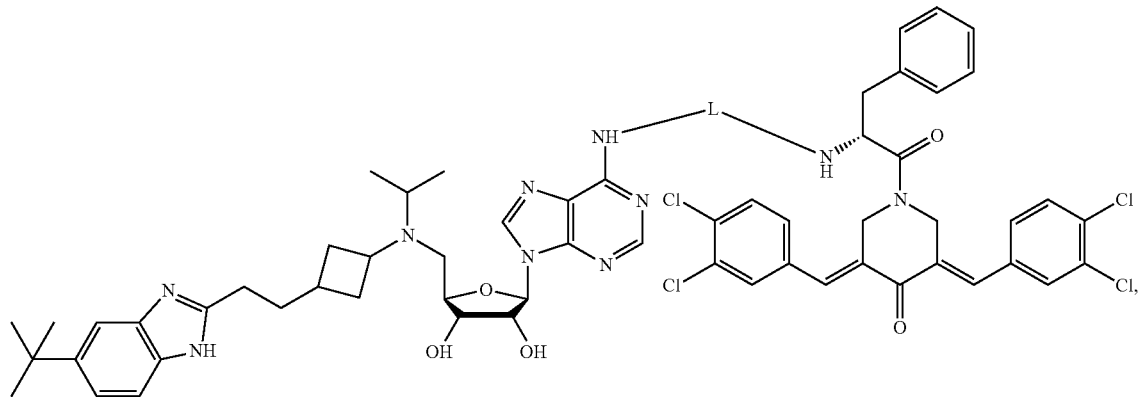
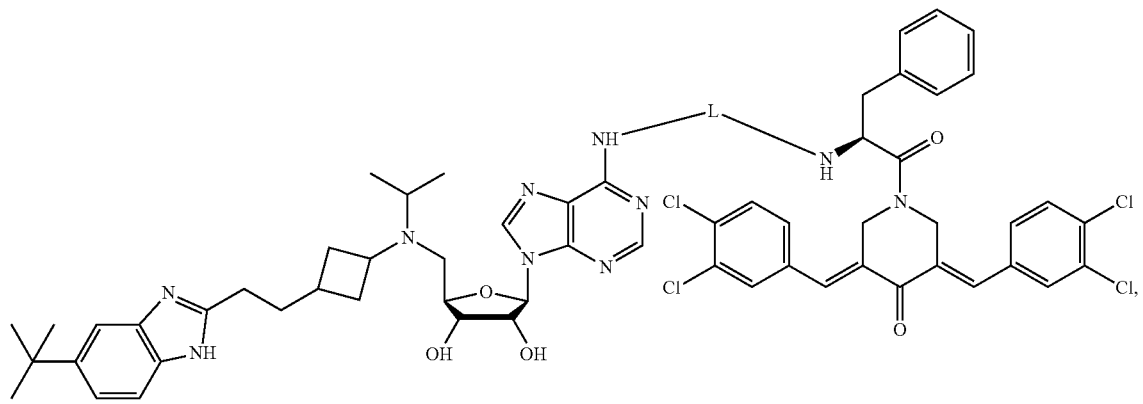

-continued
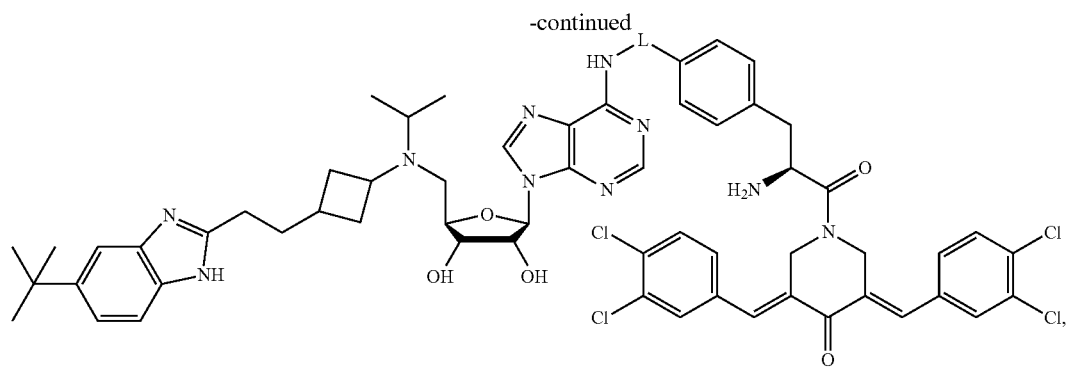
or a pharmaceutically acceptable salt, tautomer, stereoisomer, solvate, or hydrate, thereof.
12. The compound of claim 1, wherein the compound is of the formula:
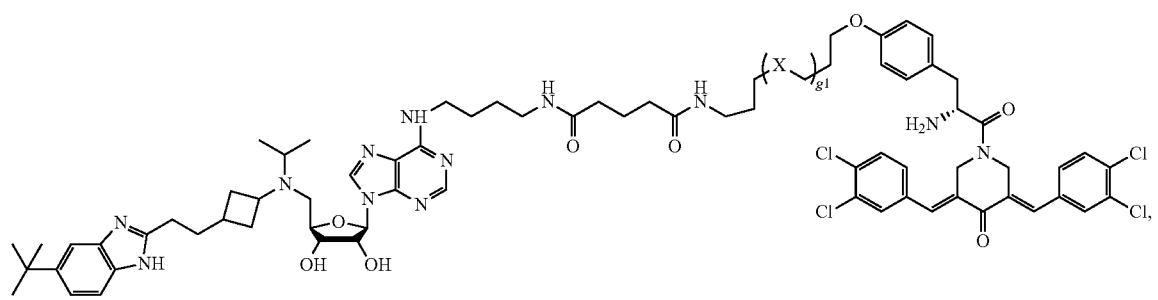
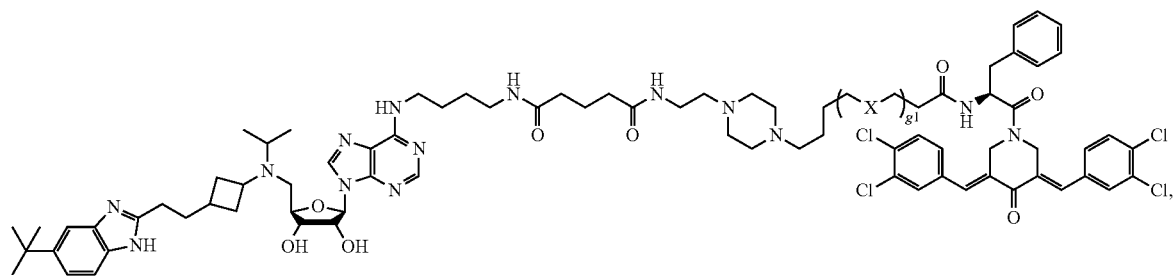
or a pharmaceutically acceptable salt, tautomer, stereoisomer, solvate, or hydrate, thereof, wherein X is $CH_2$ or O; and
g1 is 1, 2, 3, 4, 5, 6, 7, 8, 9, or 10.

13. The compound of claim 1, wherein the compound is of the formula:

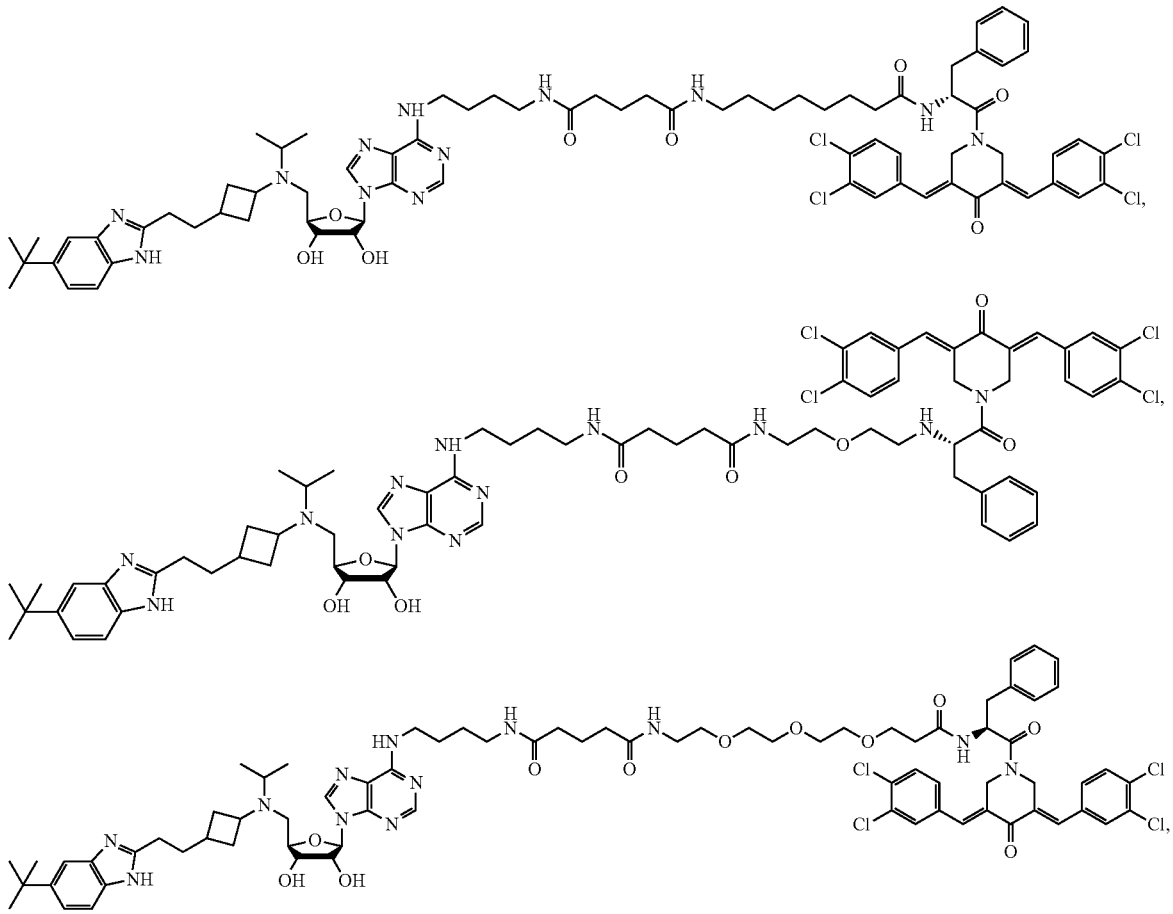

or a pharmaceutically acceptable salt, solvate, hydrate, tautomer, or stereoisomer thereof.

14. A pharmaceutical composition comprising a compound of claim 1, or a pharmaceutically acceptable salt, solvate, hydrate, tautomer, or stereoisomer thereof, and optionally a pharmaceutically acceptable excipient.

15. A method of inducing the degradation of DOT1L in a subject, comprising:
administering to the subject a therapeutically effective amount of a compound of claim 1, or a pharmaceutically acceptable salt, solvate, hydrate, tautomer, or stereoisomer thereof.

16. A method of inducing degradation of DOT1L in a cell, tissue, or biological sample comprising:
contacting the cell, tissue, or biological sample with a therapeutically effective amount of a compound of claim 1, or a pharmaceutically acceptable salt, solvate, hydrate, tautomer, or stereoisomer thereof.

17. The compound of claim 7, wherein the compound is of formula:

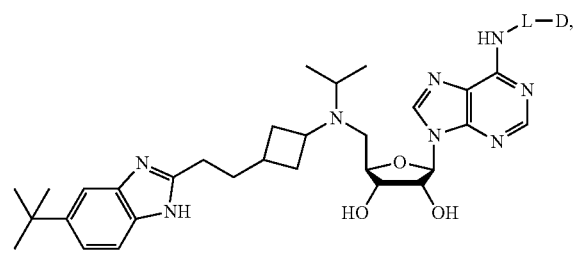

or a pharmaceutically acceptable salt, solvate, hydrate, tautomer, or stereoisomer thereof.